(12) United States Patent
Molino et al.

(10) Patent No.: US 7,511,013 B2
(45) Date of Patent: Mar. 31, 2009

(54) CYCLOSPORIN ANALOGUES AND THEIR PHARMACEUTICAL USES

(75) Inventors: Bruce F. Molino, Slingerlands, NY (US); Zhicai Yang, Schenectady, NY (US)

(73) Assignee: AMR Technology, Inc., Manchester Center, VT (US)

( * ) Notice: Subject to any disclaimer, the term of this patent is extended or adjusted under 35 U.S.C. 154(b) by 0 days.

(21) Appl. No.: 11/232,292

(22) Filed: Sep. 21, 2005

(65) Prior Publication Data

US 2006/0069015 A1    Mar. 30, 2006

Related U.S. Application Data

(60) Provisional application No. 60/614,266, filed on Sep. 29, 2004.

(51) Int. Cl.
*A61K 38/13* (2006.01)
(52) U.S. Cl. .............................. 514/9; 514/10; 530/317
(58) Field of Classification Search ........................ None
See application file for complete search history.

(56) References Cited

U.S. PATENT DOCUMENTS

| | | | |
|---|---|---|---|
| 4,210,581 A | 7/1980 | Rüegger et al. | |
| 4,288,431 A | 9/1981 | Traber et al. | |
| 4,384,996 A | 5/1983 | Bollinger et al. | |
| 4,396,542 A | 8/1983 | Wenger | |
| 4,554,351 A | 11/1985 | Wenger | |
| 4,639,434 A | 1/1987 | Wenger et al. | |
| 4,649,047 A | 3/1987 | Kaswan | |
| 4,703,033 A | 10/1987 | Seebach | |
| 4,727,035 A | 2/1988 | Mahoney | |
| 4,764,503 A | 8/1988 | Wenger | |
| 4,771,122 A | 9/1988 | Seebach | |
| 4,814,323 A | 3/1989 | Andrieu et al. | |
| 4,839,342 A | 6/1989 | Kaswan | |
| 4,885,276 A | 12/1989 | Witzel | |
| 5,030,739 A | 7/1991 | Foricher et al. | |
| 5,116,816 A | 5/1992 | Dreyfuss et al. | |
| 5,169,773 A | 12/1992 | Rosenthaler et al. | |
| 5,284,826 A | 2/1994 | Eberle | |
| 5,318,901 A | 6/1994 | Patchett et al. | |
| 5,411,952 A | 5/1995 | Kaswan | |
| 5,525,590 A | 6/1996 | Bollinger et al. | |
| 5,643,870 A | 7/1997 | Boelsterli et al. | |
| 5,767,069 A | 6/1998 | Ko et al. | |
| 5,834,266 A | 11/1998 | Crabtree et al. | |
| 5,840,900 A | 11/1998 | Greenwald et al. | |
| 5,846,514 A | 12/1998 | Foster et al. | |
| 5,869,337 A | 2/1999 | Crabtree et al. | |
| 5,869,709 A | 2/1999 | Marwah et al. | |
| 5,948,693 A | 9/1999 | Rich et al. | |
| 5,948,884 A | 9/1999 | Luchinger | |
| 5,981,479 A | 11/1999 | Ko et al. | |
| 5,994,299 A | 11/1999 | Barriere et al. | |

| | | |
|---|---|---|
| 6,255,100 B1 | 7/2001 | Ko et al. |
| 6,605,593 B1 | 8/2003 | Naicker et al. |

(Continued)

FOREIGN PATENT DOCUMENTS

BR        9603738-5 A       5/1998

(Continued)

OTHER PUBLICATIONS

File HCAPLUS on STN, AN No. 2003:319927. Abstract of WO2003033527, published Apr. 24, 2003. Abstract entered into STN Apr. 25, 2003.*

(Continued)

*Primary Examiner*—Anish Gupta
(74) *Attorney, Agent, or Firm*—Nixon Peabody LLP

(57) ABSTRACT

The compounds of the present invention are represented by Formula I, as shown below:

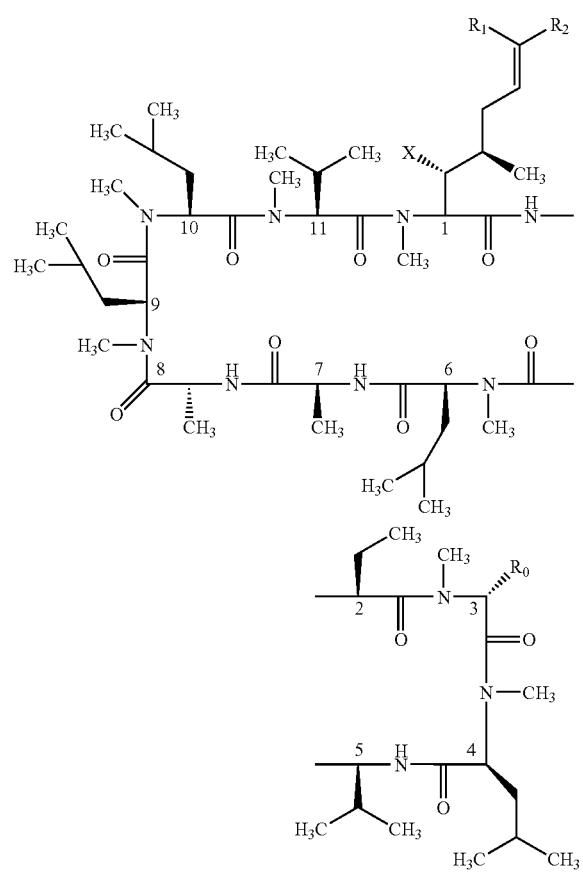

Formula I or a pharmaceutically acceptable salt thereof, with X, $R_0$, $R_1$, and $R_2$ defined herein.

9 Claims, 1 Drawing Sheet

U.S. PATENT DOCUMENTS

| | | |
|---|---|---|
| 6,613,739 B1 | 9/2003 | Naicker et al. |
| 6,686,454 B1 | 2/2004 | Yatscoff et al. |
| 6,723,339 B2 | 4/2004 | Meinzer et al. |
| 6,767,555 B2 | 7/2004 | Ambuhl et al. |
| 6,784,156 B2 | 8/2004 | Or et al. |
| 6,809,077 B2 | 10/2004 | Or et al. |
| 6,844,459 B2 | 1/2005 | Hauer et al. |
| 6,927,208 B1 | 8/2005 | Wenger et al. |
| 6,979,671 B2 | 12/2005 | Or et al. |
| 6,998,385 B2 | 2/2006 | Naicker et al. |
| 7,012,064 B2 | 3/2006 | Or et al. |
| 7,012,065 B2 | 3/2006 | Or et al. |
| 7,060,672 B2 | 6/2006 | Naicker et al. |
| 2002/0127198 A1 | 9/2002 | Rothbard et al. |
| 2002/0128470 A1 | 9/2002 | Fuenfschilling et al. |
| 2002/0132763 A1 | 9/2002 | Naicker et al. |
| 2002/0142946 A1 | 10/2002 | Or et al. |
| 2003/0022831 A1 | 1/2003 | Rothbard et al. |
| 2003/0087813 A1 | 5/2003 | Or et al. |
| 2003/0104992 A1 | 6/2003 | Or et al. |
| 2003/0109425 A1 | 6/2003 | Or et al. |
| 2003/0109426 A1 | 6/2003 | Or et al. |
| 2003/0139326 A1 | 7/2003 | Naicker et al. |
| 2003/0166515 A1 | 9/2003 | Or et al. |
| 2003/0171264 A1 | 9/2003 | Naicker et al. |
| 2003/0186855 A1 | 10/2003 | Or et al. |
| 2003/0212249 A1 | 11/2003 | Naicker et al. |
| 2003/0220234 A1 | 11/2003 | Naicker et al. |
| 2004/0087496 A1 | 5/2004 | Kim et al. |
| 2004/0110666 A1 | 6/2004 | Or et al. |
| 2004/0157768 A1 | 8/2004 | Or et al. |
| 2004/0220091 A1 | 11/2004 | Adam et al. |
| 2004/0235716 A1 | 11/2004 | Molino et al. |
| 2004/0266669 A1 | 12/2004 | Wu et al. |
| 2005/0176628 A1 | 8/2005 | Naicker et al. |
| 2005/0192214 A1 | 9/2005 | Naicker et al. |
| 2006/0035821 A1 | 2/2006 | Hunt et al. |
| 2006/0035822 A1 | 2/2006 | Hunt et al. |
| 2006/0052290 A1 | 3/2006 | Naicker et al. |
| 2006/0069015 A1 | 3/2006 | Molino et al. |
| 2006/0069016 A1 | 3/2006 | Molino et al. |
| 2006/0074015 A1 | 4/2006 | Molino et al. |
| 2006/0135414 A1 | 6/2006 | Naicker et al. |
| 2006/0217309 A1 | 9/2006 | Naicker et al. |

FOREIGN PATENT DOCUMENTS

| | | |
|---|---|---|
| CA | 1106303 A2 | 8/1981 |
| CA | 1292962 C | 12/1991 |
| CA | 2076291 AA | 2/1993 |
| CA | 2096892 A | 11/1993 |
| CA | 2086267 AA | 6/1994 |
| CH | 628872 A | 3/1982 |
| CH | 630061 A | 5/1982 |
| CH | 630062 A | 5/1982 |
| CH | 637123 A | 7/1983 |
| CH | 640520 A | 1/1984 |
| CZ | 277471 B6 | 3/1993 |
| CZ | 277472 B6 | 3/1993 |
| CZ | 280552 B6 | 2/1996 |
| CZ | 280553 B6 | 2/1996 |
| DE | 2455859 A1 | 6/1975 |
| DE | 2648121 A1 | 5/1977 |
| DE | 2819094 A1 | 11/1978 |
| DE | 285793 A5 | 1/1991 |
| DE | 295245 A5 | 10/1991 |
| DE | 295870 A | 11/1991 |
| DE | 295871 A | 11/1991 |
| DE | 4032268 A1 | 4/1992 |
| DE | 4236237 A1 | 4/1994 |
| DE | 19933173 A1 | 1/2001 |
| DE | 102004011988 A1 | 9/2005 |
| EP | 0 034 567 | 11/1984 |
| EP | 283801 A2 | 9/1988 |
| EP | 300785 A2 | 1/1989 |
| EP | 375454 A1 | 6/1990 |
| EP | 444897 A1 | 9/1991 |
| EP | 471295 A1 | 2/1992 |
| EP | 473961 A2 | 3/1992 |
| EP | 487289 A2 | 5/1992 |
| EP | 642799 A1 | 3/1995 |
| EP | 0 484 281 B2 | 11/2000 |
| FR | 2640641 A1 | 6/1990 |
| FR | 2757520 A1 | 6/1998 |
| FR | 2757521 A1 | 6/1998 |
| FR | 2757522 A1 | 6/1998 |
| FR | 2851471 A1 | 8/2004 |
| GB | 2205317 A1 | 12/1988 |
| GB | 2206119 A1 | 12/1988 |
| GB | 2207678 A1 | 2/1989 |
| GB | 2212499 A1 | 7/1989 |
| GB | 2227244 A1 | 7/1990 |
| JP | 57063093 A2 | 4/1982 |
| JP | 05271267 A2 | 10/1993 |
| JP | 07278187 A2 | 10/1995 |
| JP | 10279596 A2 | 10/1998 |
| JP | 2002080394 A2 | 3/2002 |
| JP | 2005198543 A2 | 7/2005 |
| JP | 2005325061 A2 | 11/2005 |
| KR | 161664 B1 | 11/1998 |
| KR | 2002089300 A | 11/2002 |
| RU | 2144017 C1 | 1/2000 |
| WO | WO 90/06763 | 6/1990 |
| WO | WO 92/06998 | 4/1992 |
| WO | WO 92/13094 | 8/1992 |
| WO | WO 92/13569 | 8/1992 |
| WO | WO 93/07150 | 4/1993 |
| WO | WO 94/18317 | 8/1994 |
| WO | WO 94/25606 | 11/1994 |
| WO | WO 95/02684 | 1/1995 |
| WO | WO 96/06111 | 2/1996 |
| WO | WO 96/06857 | 3/1996 |
| WO | WO 96/27607 | 9/1996 |
| WO | WO 96/40758 | 12/1996 |
| WO | WO 97/04005 | 2/1997 |
| WO | WO 97/11092 | 3/1997 |
| WO | WO 97/45675 | 12/1997 |
| WO | WO 98/03192 | 1/1998 |
| WO | WO 98/07713 | 2/1998 |
| WO | WO 98/08956 | 3/1998 |
| WO | WO 98/46247 | 10/1998 |
| WO | WO 98/49193 | 11/1998 |
| WO | WO 98/58927 | 12/1998 |
| WO | WO 99/02659 | 1/1999 |
| WO | WO 99/10373 | 3/1999 |
| WO | WO 99/10374 | 3/1999 |
| WO | WO 99/18120 | 4/1999 |
| WO | WO 99/21879 | 5/1999 |
| WO | WO 99/32512 | 7/1999 |
| WO | WO 99/62540 | 12/1999 |
| WO | WO 99/65933 | 12/1999 |
| WO | WO 99/67280 | 12/1999 |
| WO | WO 00/01715 | 1/2000 |
| WO | WO 00/08033 | 2/2000 |
| WO | WO 00/51558 | 9/2000 |
| WO | WO 00/67801 | 11/2000 |
| WO | WO 01/05819 A1 | 1/2001 |
| WO | WO 01/13957 A2 | 3/2001 |
| WO | WO 01/35913 A1 | 5/2001 |
| WO | WO 01/35914 A1 | 5/2001 |
| WO | WO 02/24865 A2 | 3/2002 |
| WO | WO 02/41858 A1 | 5/2002 |
| WO | WO 02/41859 A1 | 5/2002 |
| WO | WO 02/064106 A1 | 8/2002 |

| | | |
|---|---|---|
| WO | WO 02/065986 A2 | 8/2002 |
| WO | WO 02/067917 A1 | 9/2002 |
| WO | WO 02/069902 A2 | 9/2002 |
| WO | WO 02/076927 A2 | 10/2002 |
| WO | WO 02/085928 A2 | 10/2002 |
| WO | WO 02/092032 A1 | 11/2002 |
| WO | WO 02/092033 A1 | 11/2002 |
| WO | WO 03/030834 A2 | 4/2003 |
| WO | WO 03/032949 A1 | 4/2003 |
| WO | WO 03/033010 A1 | 4/2003 |
| WO | WO 03/033526 A2 | 4/2003 |
| WO | WO 03/033527 A2 | 4/2003 |
| WO | WO 03/034980 A2 | 5/2003 |
| WO | WO 03/049772 A2 | 6/2003 |
| WO | WO 03/070755 A2 | 8/2003 |
| WO | WO 2004/050687 A2 | 6/2004 |
| WO | WO 2004/072108 A1 | 8/2004 |
| WO | WO 2004/082629 A2 | 9/2004 |
| WO | WO 2004/089960 A2 | 10/2004 |
| WO | WO 2004/096236 A2 | 11/2004 |
| WO | WO 2004/100960 A2 | 11/2004 |
| WO | WO 2005/000879 A1 | 1/2005 |
| WO | WO 2005/021028 A1 | 3/2005 |
| WO | WO 2005/046575 A2 | 5/2005 |
| WO | WO 2005/097164 A2 | 10/2005 |
| WO | WO 2006/005580 A1 | 1/2006 |
| WO | WO 2006/005610 A1 | 1/2006 |
| WO | WO 2006/014872 A2 | 2/2006 |
| WO | WO 2006/063470 A1 | 6/2006 |
| WO | WO 2006/066416 A1 | 6/2006 |
| WO | WO 2006/071618 A1 | 7/2006 |

OTHER PUBLICATIONS

Abel et al., "ISATX247: A Novel Calcineurin Inhibitor," *J. Heart Lung Transplant.* 20(2):161 (2001) (Abstract 36).
Aspeslet et al., "ISA$_{TX}$247: A Novel Calcineurin Inhibitor," *Transplant Proc.* 33:1048-1051 (2001).
Buetler et al., "Does Cyclosporin A Generate Free Radicals?" *TIPS* 21:288-290 (2000).
Christians & Sewing, "Cyclosporin Metabolism in Transplant Patients," *Pharmac. Ther.* 57:291-345 (1993).
Clark & Yorio, "Ophthalmic Drug Discovery," *Nat. Rev. Drug Discov.* 2(6):448-459 (2003).
Dumont, "ISAtx-247 Isotechnika/Roche," *Curr. Opin. Investig. Drugs* 5(5):542-550 (2004).
Eberle et al., "Preparation of Sulfhydryl Cyclosporin A," *J. Org. Chem.* 60:2610-2612 (1995).
Eckstein & Fung, "A New Class of Cyclosporin Analogues for the Treatment of Asthma," *Expert Opin. Investig. Drugs* 12(4):647-653 (2003).
Foster, "Deuterium Isotope Effects in Studies of Drug Metabolism," *TIPS* 5:524-527 (1984).
Fritz-Langhals & Kunath, "Synthesis of Aromatic Aldehydes by Laccase-Mediator Assisted Oxidation," *Tetrahedron Lett.* 39:5955-5956 (1998).
Henke et al., "Cyclosporine A Inhibits ATP Net Uptake of Rat Kidney Mitochondria," *Biochem. Pharmacol.* 43(5):1021-1024 (1992).
Kallen et al., "12 Cyclosporins: Recent Developments in Biosynthesis, Pharmacology and Biology, and Clinical Applications," *Biotechnology*, Second Edition, Rehm et al, eds., pp. 535-591 (1997).
Khanna et al., "TGF-β: A Link Between Immunosuppression, Nephrotoxicity, and CsA," *Transplant. Proc.* 30:944-945 (1998).
Ko & Wenger, "53. Solid-Phase Total Synthesis of Cyclosporine Analogues," *Helvetica Chimica Acta* 80:695-705 (1997).
Lazarova et al., "Synthesis and Biological Evaluation of Novel Cyclosporin A Analogues: Potential Soft Drugs for the Treatment of Autoimmune Diseases," *J. Med. Chem.* 46:674-676 (2003).
Loor, "Cyclosporins and Related Fungal Products in the Reversal of P-Glycoprotein-Mediated Multidrug Resistance," in *Multidrug Resistance in Cancer Cells* Gupta et al, eds., John Wiley and Sons Ltd: Chichester, pp. 385-412 (1996).

Loor, "Valspodar: Current Status and Perspectives," *Exp. Opin. Invest. Drugs* 8(6):807-835 (1999).
Mlynar et al., "The Non-Immunosuppressive Cyclosporin A Analogue SDZ NIM 811 Inhibits Cyclophilin A Incorporation Into Virions and Virus Replication in Human Immunodeficiency Virus Type 1-Infected Primary and Growth-Arrested T Cells," *J. Gen. Virol.* 78(4):825-835 (1997).
Offenzeller et al., "Biosynthesis of the Unusual Amino Acid (4R)-4-[(E)-2-Butenyl]-4-methyl-L-threonine of Cyclosporin A: Enzymatic Analysis of the Reaction Sequence Including Identification of the Methylation Precursor in a Polyketide Pathway," *Biochem.* 35:8401-8412 (1996).
Paolini, "Cyclosporin A and Free Radical Generation," *TIPS* 22(1):14-15 (2001).
Park & Meier, "A Semi-Synthetic Approach to Olefinic Analogs of Amino Acid One (MeBMT) in Cyclosporin A," *Tetrahedron Lett.* 30(32):4215-4218 (1989).
Potthast et al., "A Novel Method for the Conversion of Benzyl Alcohols to Benzaldehydes by Laccase-Catalyzed Oxidation," *J. Mol. Catalysis A* 108:5-9 (1996).
Punniyamurthy & Iqbal, "Cobalt Catalysed Allylic and Benzylic Oxidations with Dioxygen in the Presence of Ethyl 2-Oxocyclopentanecarboxylate," *Tetrahedron Lett.* 35(23):4003-4006 (1994).
Seebach et al., "Modification of Cyclosporin A (CS): Generation of an Enolate at the Sarcosine Residue and Reactions with Electrophiles," *Helvetica Chimica Acta* 76:1564-1590 (1993).
Seebach & Ko, "Thiocyclosporins: Preparation, Solution and Crystal Structure, and Immunosuppressive Activity," *Helvetica Chimica Acta* 74:1953-1990 (1991).
Serino et al., "Oxygen Radical Formation by the Cytochrome P450 System as a Cellular Mechanism for Cyclosporine Toxicity," *Transplant. Proc.* 26:2916-2917 (1994).
Serkova et al., "The Novel Immunosuppressant SDZ-RAD Protects Rat Brain Slices from Cyclosporine-Induced Reduction of High-Energy Phosphates," *Br. J. Pharmacol.* 129:485-492 (2000).
Snyder & Sabatini, "Immunophilins and the Nervous System," *Nat. Med.* 1(1):32-37 (1995).
Snyder et al., "Neural Actions of Immunophilin Ligands," *TIPS* 19:21-26 (1998).
Steiner et al., "Neurotrophic Actions of Nonimmunosuppressive Analogues of Immunosuppressive Drugs FK506, Rapamycin and Cyclosporin A," *Nat. Med.*3(4):421-428 (1997).
Traber et al., "Cyclosporins-New Analogues by Precursor Directed Biosynthesis," *J. Antibiotics* 42(4):591-597 (1989).
Traber et al., "122. Die Struktur von Cyclosporin C," *Helvetica Chimica Acta* 60(4):1247-1255 (1977) (English Abstract Only).
Traber et al., "162. Isolierung und Strukturermittlung der neuen Cyclosporine E, F, G, H und I," *Helvetica Chimica Acta* 65(5):1655-1677 (1982) (English Abstract Only).
Traber et al., "2. Neue Cyclosporine aus *Tolypocladium inflatum* Die Cyclosporine K-Z," *Helvetica Chimica Acta* 70:13-36 (1987) (English Abstract Only).
Wenger, "60. Synthesis of Cyclosporine: Total Syntheses of 'Cyclosporin A' and 'Cyclosporin H', Two Fungal Metabolites Isolated from the Species *Tolypocladium inflatum* G$_{AMS}$," *Helvetica Chimica Acta* 67(2):502-525 (1984).
Wenger, "Structures of Cyclosporine and Its Metabolites," *Transplant. Proc.* 22(3):1104-1108 (1990).
Xu et al., "Redox Chemistry in Laccase-Catalyzed Oxidation of N-Hydroxy Compounds," *Appl. Environ. Microbiol.* 66(5):2052-2056 (2000).
Aebi et al., "Synthesis, Conformation, and Immunosuppressive Activities of Three Analogs of Cyclosporin A Modified in the 1-Position," *Journal of Medicinal Chemistry* 33(3):999-1009 (1990).
Agathos et al., "Enhancement of Cyclosporin Production in a Tolypocladium inflatum Strain After Epichlorohydrin Treatment," *Journal of Biotechnology* 13(1):73-81 (1990).
Agathos et al., "The Fungal Production of Cyclosporins," *Annals of the New York Academy of Sciences*, 506(Biochem. Eng. 5):657-662 (1987).

Alberg et al., "Structure-Based Design of a Cyclophilin-Calcineurin Bridging Ligand," *Science* (Washington, DC, United States) 262(5131):248-250 (1993).

Andres et al., "Interaction of Lead(II) With Highly-Dentate Linear and Cyclic Polyamines," *Journal of the Chemical Society, Dalton Transactions: Inorganic Chemistry* (23):3507-3513 (1972-1999) (1993).

Angell et al. "Innovation and Perspectives in Solid Phase Synthesis & Combinatorial Libraries: Peptides, Proteins and Nucleic Acids—Small Molecule Organic Chemical Diversity, Collected Papers," in Epton, ed. *International Symposium*, 5th, London, Sep. 2-6, 1997 (1999), Meeting Date 1997, Mayflower Scientific Ltd.: Kingswinford, pp. 135-138.

Angell et al., "Solid-Phase Synthesis of Cyclosporin Peptides," *Journal of the American Chemical Society* 117(27):7279-7280 (1995).

Angell, "The Solid-Phase Synthesis Of Cyclosporin A Analogs," Diss. Abstr. Int., B 1997, 57(9):5657(1996).

Belshaw et al. "Cell-Specific Calcineurin Inhibition by a Modified Cyclosporin," *Journal of the American Chemical Society* 119(7):1805-1806 (1997).

Belshaw et al., "Controlling Protein Association and Subcellular Localization With a Synthetic Ligand That Induces Heterodimerization of Proteins," *Proceedings of the National Academy of Sciences of the United States of America*, 93(10):4604-4607 (1996).

Belshaw et al., "Rational Design of Orthogonal Receptor-Ligand Combinations," *Angewandte Chemie, International Edition In English*, 34(19):2129-2132 (1995).

Bencini et al., "Anaerobic Complexation of Cobalt(II) by [3k]aneNk (k=7-12) Polyazacycloalkanes," *Inorganic Chemistry* 28(12):2480-2482 (1989).

Bencini et al., "Synthesis and Ligational Properties of the Two Very Large Polyazacycloalkanes [33]aneN11 and [36]aneN12 Forming Trinuclear Copper(II) Complexes," *Inorganic Chemistry* 27(1):176-180 (1988).

Bencini et al., "Thermodynamic and Structural Aspects of the Interaction Between Macrocyclic Polyammonium Catoins and Complexed Anions," *Inorganic Chemistry* 31(10):1902-1908 (1992).

Billich et al., Enzymic Synthesis of Cyclosporin A,: *Journal of Biological Chemistry* 262(36):17258-17259 (1987).

Billich et al., "Novel Cyclosporin Derivatives Featuring Enhanced Skin Penetration Despite Increased Molecular Weight," *Bioorganic and Medicinal Chemistry* 13(9):3157-3167 (2005).

Bohnstedt, "The Synthesis And Biological Activities Of Novel Backbone-Modified Analogs Of Cyclosporin A," Diss. Abstr. Int. B 1995, 55(11), 4848 (1994).

Brooks et al., "Preparative Chromatographic Purification of Cyclosporine Metabolites," *Clinical Chemistry* (Washington, DC, United States) 39(3):457-466 (1993).

Brugghe et al., "Simultaneous Multiple Synthesis and Selective Conjugation of Cyclized Peptides Derived from a Surface Loop of a Meningococcal Class 1 Outer Membrane Protein," *International Journal of Peptide & Protein Research* 43(2), 166-172 (1994).

Buchta et al., "A Cyclosporin From Mycelium Sterilae," *Phytochemistry* 48(7):1195-1198 (1998).

Burtscher et al., "Synthesis of [S-[1-14C]val7]Valspodar: Application of (+)/(−)-[13,14Cn]BABS and (+)/(−)-[13,14Cn]DPMGBS," *Journal of Labelled Compounds & Radiopharmaceuticals* 43(3):205-216 (2000).

Cacalano et al., "Antibodies to Cyclosporine A (CsA) by a Novel Route and Their Use to Monitor Cyclosporine Levels by Radioimmunoassay (RIA)," *Journal of Immunological Methods* 118(2):257-263 (1989).

Carry et al., "Semisynthetic Di- and Tri-Functionalized Non-Immunosuppressive Cyclosporin A Derivatives as Potential Anti-HIV 1 Drugs," *Synlett* (2):316-320 (2004).

Cerny et al., "Synthesis of [ω-3H-MeBmt1]-Cyclosporin A," *Journal of Labelled Compounds & Radiopharmaceuticals* 41(4):267-272 (1998).

Chen et al., "A Sensitive Enzyme Immunoassay for Cyclosporin A Using Antibodies Generated Agains A Novel Hapten," *Research Communications in Molecular Pathology and Pharmacology* 88(3):317-326 (1995).

Cho et al., "Water Soluble Cyclosporine Monomethyoxy Poly(Ethyleneglycol) Conjugates as Potential Prodrugs," *Archives of Pharmacal Research* 27(6):662-669 (2004).

Chu et al., "A New Producer of Cyclosporin C," *Zhongguo Kangshengsu Zazhi* 23(1):1-5, 16 (1998).

Chu et al., "Production of Cyclosporin C by *Gliomastix luzulae* Isolated From Different Areas of China," *Zhongguo Kangshengsu Zazhi* 23(3):116-120 (1998).

Chu et al., "Screening of Antifungal Substances with Immunosuppressive Activity by Special Morphological Abnormalities of *Azpergillus clavatus*," *Zhongguo Kangshengsu Zazhi* 23(3):193-196 (1998).

Coates et al., "Radioimmunoassay of Salivary Cyclosporine With Use of Iodine-125-Labeled Cyclosporine," *Clinical Chemistry* (Washington, DC, United States), 34(8):1545-1551 (1988).

Colucci et al., "Synthesis of D-Lysine8-Cyclosporine A. Further Characterization of BOP-Cl in the 2-7 Hexapeptide Fragment Synthesis," *Journal of Organic Chemistry* 55(9): 2895-2903 (1990).

Dai et al., "Study of the Reaction Between Cyclosporine A and 4-Benzoylbenzoic Acid," *Jingxi Huagong* 18(3):135-137 (2001).

Donatsch et al., "A Radioimmunoassay to Measure Cyclosporin A in Plasma and Serum Samples," *Journal of Immunoassay* 2(1):19-32 (1981).

Dreyfuss et al., "Cyclosporin A and C. New Metabolites From *Trichoderma polysporum* (Link ex Pers.) Rifai," *European Journal of Applied Microbiology* 3(2):125-133 (1976).

Dugave, "Study of the cis-trans Isomerization of the Amino-Acyl Prolyl Peptide Bond: Application to the Design of Novel Inhibitors of Immunophilins," *Current Organic Chemistry* 6(15):1397-1431 (2002).

Durette et al., "A study of the Correlation Between Cyclophilin Binding and in Vitro Immunosuppressive Activity of Cyclosporine A and Analogs," *Transplantation Proceedings* 20(2, Suppl. 2):51-57 (1988).

Eberle et al., "Bridged Cyclosporins," *Journal of Organic Chemistry* 60(15):4868-4872 (1995).

Eberle et al., "Cyclosporin A: Regioselective Ring Opening and Fragmentation Reactions via Thioamides. A Route to Semisynthetic Cyclosporins," *Journal of Organic Chemistry* 59(24):7249-7258 (1994).

Eberle et al., "Modifications of the MeBmt Side Chain of Cyclosporin A," *Bioorganic & Medicinal Chemistry Letters* 5(15):1725-1728 (1995).

Eberle et al., "Preparation and in Vitro Activities of Ethers of [D-Serine]8-cyclosporin," *Journal of Medicinal Chemistry* 38(11):1853-1864 (1995).

Eberle et al., "Preparation of [D-cysteine]8-Cyclosporin Via Intramolecular Sulfur Transfer Reaction," *Journal of Organic Chemistry* 58(3):673-677 (1993).

Eberle et al., "Preparation of Functionalized Ethers of Cyclosporin A," *Tetrahedron Letters* 35(35):6477-6480 (1994).

Eberle et al., "Synthesis of the Main Metabolite (OL-17) of Cyclosporin A," *Journal of Organic Chemistry*, 57(9):2689-2691 (1992).

Endo et al., "Solution-Phase Synthesis and Structural Analysis of N-Desmethylated Cyclosporin O Analogs," *Peptide Science* 39:383-386 Volume Date 2002, (2003).

Evers et al., "Synthesis of Non-Immunosuppressive Cyclophilin-Binding Cyclosporin A Derivates as Potential Anti-HIV-1 Drugs," *Bioorganic & Medicinal Chemistry Letters* 13(24):4415-4419 (2003).

Fang et al., "Separation of Cyclosporins by High Speed Counter Current Chromatography," *Zhongguo Kangshengsu Zazhi* 30(1):48-51 (2005).

French et al., "New Fluorescent Derivatives of Cyclosporin for Use in Immunoassays," *Journal of Pharmaceutical and Biomedical Analysis* 10(1):23-30 (1992).

Galpin et al., "Synthesis of Cyclosporin Analogs," *Tetrahedron Letters* 28(51):6517-6520 (1987).

Galpin et al., "Synthetic Studies of Cyclosporin Analogs," *Tetrahedron* 44(6):1783-1794 (1988).

Gfeller et al., "Improvement of Detection Sensitivity of Cyclosporin A by Derivatization With 2-Naphthylselenyl Chloride," *Helvetica Chimica Acta* 63(3):728-732 (1980).

Giger et al., "Design and Synthesis of a Transition State Analog of a Metalloporphyrin-Catalysed Oxidation Reaction," *Journal of Porphyrins and Phthalocyanines* 6(5):362-365 (2002).

Grote et al. "A Practical Method for the Synthesis of a Cyclosporine-Fluorescein Conjugate," *Organic Process Research & Development*, 9(6):822-824 (2005).

Guichou et al., "Pseudo-Prolines (ΨPro): Direct Insertion of ΨPro Systems Into Cysteine Containing Peptides," *Tetrahedron Letters* 43(24):4389-4390 (2002).

Hamel et al., "Cyclosporin A Prodrugs: Design, Synthesis and Biophysical Properties," *Journal of Peptide Research* 63(2):147-154 (2004).

Hamel et al., "Water-Soluble Prodrugs of Cyclosporine A With Tailored Conversion Rates," *Journal of Peptide Research* 65(3):364-374 (2005).

Hensens et al., "The Preparation of [2-deutero-3-fluoro-D-Ala8]Cyclosporin A by Directed Biosynthesis," *Journal of Antibiotics* 45(1):133-135 (1992).

Hornich et al., "Variation of Amino Acids Within the Cyclosporin-Cyclophilin Binding Domain. Synthesis of a 21-Membered Cyclopeptolide," *Scientia Pharmaceutica* 64(3/4):463-470 (1996).

Hu et al., "Cyclosporin Analogs Modified in the 3,7,8-Positions: Substituent Effects on Peptidylprolyl Isomerase Inhibition and Immunosuppressive Activity Are Nonadditive," *Journal of Medicinal Chemistry* 38(21):4164-4170 (1995).

Hu, "Synthesis And Biological Properties Of Novel Cyclosporine Analogs," Diss. Abstr. Int. B 1995, 55(7), 2743 (1994).

Hubler et al., "Synthetic Routes to NEtXaa4-Cyclosporin A Derivatives as Potential Anti-HIV I Drugs," *Tetrahedron Letters* 41(37):7193-7196 (2000).

Husi et al., "Prediction of Substrate-Specific Pockets in Cyclosporin Synthetase," *FEBS Letters* 414(3):532-536 (1997).

Jegorov et al., "An Unusual Side Chain C-C Cleavage at the MeBmt Amino Acid in Cyclosporin A," *Amino Acids* 10(2):145-151 (1996).

Jegorov et al., "Cyclosporins from *Tolypocladium terricola*," *Phytochemistry* 38(2):403-407 (1995).

Jegorov et al., "Cyclosporins of Symmetry P21—a Series of Clathrates," *Journal of Inclusion Phenomena and Macrocyclic Chemistry* 37(1-4):137-153 (2000).

Jegorov et al., "Synthesis and Crystal Structure Determination of Cyclosporin H," *Collection of Czechoslovak Chemical Communications* 65(8):1317-1329 (2000).

Jiang et al., "Synthesis of Biotinylated Cyclosporin A and Studies on its Interaction With Human Cyclophilin A," *Huaxue Xuebao* 59(10):1745-1750 (2001).

Kanoh et al., Photo-Cross-Linked Small-Molecule Affinity Matrix for Facilitating Forward and Reverse Chemical Genetics *Angewandte Chemie, International Edition* 44(28):4282 (2005) [Erratum].

Kanoh et al., Photo-Cross-Linked Small-Molecule Affinity Matrix for Facilitating Forward and Reverse Chemical Genetics, *Angewandte Chemie, International Edition* 44(23):3559-3562 (2005).

Keller et al., "Pseudoprolines (ΨPro) in Drug Design: Direct Insertion of ΨPro Systems Into Cyclosporin C," *Chemistry—A European Journal* 6(23):4358-4363 (2000).

Kobel et al., "Directed Biosynthesis of Cyclosporins," *European Journal of Applied Microbiology and Biotechnology* 14(4):237-240 (1982).

Koeck et al., "Novel Backbone Conformation of Cyclosporin A: The Complex With Lithium Chloride," *Journal of the American Chemical Society* 114(7):2676-2686 (1992).

Kratochvil et al., "Crystal Structures of Cyclosporin Derivatives: O-acetyl-(4R)-4-(E-2-butyl)-4,N-Dimethyl-L-Threonyl-Cyclosporin A and O-Acetyl-(4R)-4-[E-2-(4-Bromobutyl)]-4,N-Dimethyl-L-Threonyl-Cyclosporin A," *Collection of Czechoslovak Chemical Communications* 64(1):89-98 (1999).

Kuhnt et al., "Microbial Biotransformation Products of Cyclosporin A," *Journal of Antibiotics* 49(8):781-787 (1996).

Lee et al., "Synthesis and Immunosuppressive Activities of Conformationally Restricted Cyclosporin Lactam Analogs," *International Journal of Peptide & Protein Research* 35(5):481-494 (1990).

Levitsky et al., "Exo-Mechanism Proximity-Accelerated Alkylations: Investigations of Linkers, Electrophiles and Surface Mutations in Engineered Cyclophilin-Cyclosporin Systems," *ChemBioChem* 6(5):890-899 (2005).

Levitsky et al., "Selective Inhibition of Engineered Receptors Via Proximity-Accelerated Alkylation," *Organic Letters* 5(5):693-696 (2003).

Lhoest et al., "Isolation, Identification and Immunosuppressive Activity of a New IMM-125 Metabolite From Human Liver Microsomes. Identification of its Cyclphilin A-IMM-125 Metabolite Complex by Nanospray Tandem Mass Spectrometry," *Journal of Mass Spectrometry* 33(10):936-942 (1998).

Li et al., "The Development of Highly Efficient Onium-Type Peptide Coupling Reagents Based Upon Rational Molecular Design," *Journal of Peptide Research* 58(2):129-139 (2001).

Li et al., "Total Synthesis of Cyclosporin O Both in Solution and in the Solid Phase Using Novel Thiazolium-, Inmmonium-, and Pyridinium-Type Coupling Reagents: BEMT, BDMP, and BEP," *Journal of Organic Chemistry* 65(10):2951-2958 (2000).

Liu et al., "Preparation of Cyclosporine A Immunogen," *Sichuan Daxue Xuebao, Ziran Kexueban* 38(3):407-411 (2001).

Liu et al., "Semipreparative Chromatographic Separation Of Cyclosporin G Metabolites Generated by Microsomes from Rabbits Treated With Rifampicin," *Journal of Pharmacological and Toxicological Methdos* 35(3):121-129 (1996).

Liu et al., "Structural Characterization of two Novel Oxidative Derivatives of Cyclosporine Generated by a Chemical Method," *Clinical Biochemistry* 31(3):173-180 (1998).

Lu et al., "Modification of Cyclosporin A and Conjugation of Its Derivative to HPMA Copolymers," *Bioconjugate Chemistry* 12(1):129-133 (2001).

Lu et al., "Synthesis of Bioadhesive Lectin-HPMA Copolymer-Cyclosporin Conjugates," *Bioconjugate Chemistry* 11(1):3-7 (2000).

Lynch, "The Search For Cyclophilin Inhibitors: The Design And Synthesis Of Conformationally Constrained Scaffolds," Diss. Abstr. Int., B 1995, 56(2)828 (1995).

Magni et al., "Hydrolytic Conditions for the Formation of Open-Chain Oligopeptides from Cyclosporin A," *Journal of Peptide Research* 49(3):191-194 (1997).

Mahoney et al., "Derivatives of Cyclosporin Compatible With Antibody-Based Assays: I. The Generation of [125I]-Labeled Cyclosporin," *Clinical Chemistry* (Washington, DC, United States), 31(3):459-462 (1985).

McIntyre et al., "ISA-247," *Drugs of the Future* 29(7):680-686 (2004).

Mikol et al., "The Role of Water Molecules in the Structure-Based Design of (5-Hydroxynorvaline)-2-cyclosporin: Synthesis, Biological Activity, and Crystallographic Analysis with Cyclophilin A," *Journal of Medicinal Chemistry* 38(17):3361-3367 (1995).

Muamba et al. "Peptides: The Wave of the Future," in Lebl eds., *Proceedings of the Second International and the Seventeenth American Peptide Symposium*, San Diego, CA, Jun. 9-14, 2001, 130-131 (2001).

Ohta et al., "Production of Human Metabolites of Cyclosporin A, AM1, AM4N and AM9, by Microbial Conversion," *Journal of Bioscience and Bioengineering* 99(4):390-395 (2005).

Okada et al., "Properties and the Inclusion Behavior of 6-O-α-D-Galactosyl- and 6-O-α-D-Mannosyl- Cyclodextrins," *Chemical & Pharmaceutical Bulletin* 47(11):1564-1568 (1999).

Papageorgiou et al., "Anti HIV-1 Activity of a Hydrophilic Cyclosporine Derivative With Improved Affinity to Cyclophilin," *Bioorganic & Medicinal Chemistry Letters* 6(4):497 (1996) [Erratum].

Papageorgiou et al., "Anti HIV-1 Activity of a Hydrophilic Cyclosporine Derivative With Improved Binding Affinity to Cyclophilin A," *Bioorganic & Medicinal Chemistry Letters* 6(1):23-26 (1996).

Papageorgiou et al., "Calcineurin has a Very Tight-Binding Pocket for the Side Chain of Residue 4 of Cyclosporin," *Bioorganic & Medicinal Chemistry Letters* 4(2):267-272 (1994).

Papageorgiou et al., "Conformational Control of Cyclosporin Through Substitution of the N-5 position. A new class of cyclosporin antagonists," *Bioorganic & Medicinal Chemistry* 5(1):187-192 (1997).

Papageorgiou et al., "Derivatives of Cyclosporin at Position 2 as Probes for Cyclophilin," *Bioorganic & Medicinal Chemistry Letters* 3(12):2559-64 (1993).

Papageorgiou et al., "Improved Binding Affinity for Cyclophilin A by a Cyclosporin Derivative Singly Modified at Its Effector Domain," *Journal of Medicinal Chemistry* 37(22):3674-3676 (1994).

Paprica et al., "Preparation of Novel Cyclosporin A Derivatives," *Bioconjugate Chemistry* 3(1):32-36 (1992).

Patchett et al., "Analogs of Cyclosporin A Modified at the D-Ala8 Position," *Journal of Antibiotics* 45(1):94-102 (1992).

Patiny et al., "Structure-Activity Studies of Novel D-Ser8-Cyclosporin A Derivatives As Potential Anti-HIV Drugs," *Peptides 2002, Proceedings of the European Peptide Symposium, 27th*, Benedetti et al. (eds) 1020-1021 (2002).

Patiny et al., "Synthesis and Characterization of Constrained Cyclosporin A Derivatives Containing a Pseudo-Proline Group," *Tetrahedron* 59(28):5241-5249 (2003).

Pflanz et al., "Induction and Rapid Screening of Monoclonal Antibodies Against Cyclosporin A," *Immunology Letters*, 18(4):241-245 (1988).

Pohl et al., "Crystal Structures of Two Modifications of [3,O-Didehydro-MeBmt1,Val2]Cyclosporin and Comparison of Three Different X-Ray Data Sets," *Helvetica Chimica Acta* 78(2):355-366 (1995).

Radeke et al., "Additive and Synergistic Effects of Cyclosporine Metabolites on Glomerular Mesangial Cells," *Kidney International* 39(6):1255-1266 (1991).

Raman Dissertation, 338 pp. Avail.: UMI, Order No. DA9809876 From: Diss. Abstr. Int., B 1998, 59(3), 1117 (1997).

Raman et al., "Methods to Circumvent a Difficult Coupling in the Solid-Phase Synthesis of Cyclosporine Analogs," *Journal of Organic Chemistry* 63(17):5734-5735 (1998).

Rich et al., "Synthesis and Antimitogenic Activities of Four Analogs of Cyclosporin A Modified in the 1-Position," *Journal of Medicinal Chemistry* 29(6):978-984 (1986).

Rich et al., "Synthesis, Biological Activity, and Conformational Analysis of (2S,3R,4S)-MeBmt-Cyclosporin, A Novel 1-Position Epimer of Cyclosporin A," *Journal of Medicinal Chemistry* 32(8):1982-1987 (1989).

Rihova et al., "Cytotoxic and Cytostatic Effects of Anti-Thy 1.2 Targeted Doxorubicin and Cyclosporin A," *Journal of Controlled Release* 40(3):303-319 (1996).

Roedl et al., "Lipoprotein-Induced Modulation of Cyclosporine A-Mediated Immunosuppression," *European Journal of Clinical Investigation* 20(3):248-252 (1990).

Romanova et al., "Synthesis of Cyclosporin A Fragment 8-11," *Ukrainskii Khimicheskii Zhurnal* (Russion Edition) 55(5):527-530 (1989).

Rothbard et al., "Conjugation of Arginine Oligomers to Cyclosporin A Facilitates Topical Delivery and Inhibition of Inflammation," *Nature Medicine* New York 6(11):1253-1257 (2000).

Rothe et al., in Brunfeldt, ed., *Pept., Proc. Eur. Pept. Symp.*, 16th Meeting Date 1980, Scriptor: Copenhagen, Den pp. 258-263 (1981).

Rozycki et al., "New Cyclosporin A Analog: Synthesis and Immunosuppressive Activity," *Molecular Immunology* 29(9):1043-1047 (1992).

Ruegger et al., "Cyclosporin A, A Peptide Metabolite From *Trichoderma polysporum* (Link ex Pers.) Rifai, With Immunosuppressive Activity," *Helvetica Chimica Acta* 59(4):1075-1092 (1976).

Sakamoto et al., "FR901459, a Novel Immunosuppressant Isolated From *Stachybotrys chartarum* No. 19392. Taxonomy of the Producing Organism, Fermentation, Isolation, Physico-Chemical Properties and Biological Activities," *Journal of Antibiotics* 46(12):1788-1798 (1993).

Shevchenko et al., "Synthesis of Tritiated Cyclosporin A and FK-506 by Metal-Catalyzed Hydrogen Isotope Exchange," *Journal of Labelled Compounds & Radiopharmaceuticals* 47(7):407-414 (2004).

Shevchenko et al., Synthesis of Tritium-Labeled Immunodepressants Containing Double Bonds by Isotope Exchange with Tritium Water, *Radiochemistry* (Moscow) (Translation of Radiokhimiya) 41(1):85-88 (1999).

Smulik et al., "Synthesis of Cyclosporin A-Derived Affinity Reagents by Olefin Metathesis," *Organic Letters* 4(12):2051-2054 (2002).

Stabler et al., "Chemiluminescence Immunoassay of Cyclosporine in Whole Blood," *Clinical Chemistry* (Washington, DC, United States), 36(6):906-908 (1990).

Sun et al., "Synthesis, Conformation, and Immunosuppressive Activity of Cyclosporins That Contain ε-Oxygen (4R)-4-[(E)-butenyl]-4,N-Dimethyl-L-Threonine Analogs in the 1-Position," *Journal of Medicinal Chemsitry* 33(5):1443-1452 (1990).

Sun, "Synthesis Of Cyclosporin Analogs Modified in the 1-Position," Diss. Abstr. Int. B 1990, 50(12, Pt. 1), 5637 (1989).

Tamolang et al., "A Rifampicin-Induced Hepatic Microsomal Enzyme System for the Generation of Cyclosporine Metabolites," *Pharmacological Research* 32(3):141-148 (1995).

Thern et al., "Peptides: The Wave of the Future," in Lebl, eds., *Proceedings of the Second International and the Seventeenth American Peptide Symposium*, San Diego, CA, Jun. 9-14, 2001, 244-245 (2001).

Thern et al., "Triphosgene as Highly Efficient Reagent for the Solid-Phase Coupling of N-Alkylated Amino Acids-Total Synthesis of Cyclosporin O," *Tetrahedron Letters* 43(28):5013-5016 (2002).

Traber et al., "[Melle4]Cyclosporin, a Novel Natural Cyclosporin With Anti-HIV Activity: Structural Elucidation, Biosynthesis and Biological Properties," *Antiviral Chemistry & Chemotherapy* 5(5):331-339 (1994).

Traber et al., "New Cyclopeptides From *Trichoderma polysporum* (Link ex Pers.) Rifai: Cyclosporins B, D and E," *Helvetica Chimica Acta* 60(5):1568-1578 (1977).

Traber et al., "Novel Cyclosporins from *Tolypocladium inflatum*. Cyclosporins K-Z," *Helvetica Chimica Acta* 70(1):13-36 (1987).

Traber et al., "Occurrence of Cyclosporins and Cyclosporin-Like Peptolides in Fungi," *Journal of Industrial Microbiology & Biotechnology* 17(5/6):397-401 (1996).

Traber et al., "The Structure of Cyclosporin C," *Helvetica Chimica Acta* 60(4):1247-1255 (1977).

Tung et al., "Synthesis and Biological Properties of a High Specific Activity Radioiodinated, Photolabile Cyclosporin," *UCLA Symposia on Molecular and Cellular Biology, New Series*, 86(Synth. Pept.), pp. 321-335 (1989).

Tuominen et al., "Separation of Cyclosporins by High-Performance Liquid Chromatography and Mass Spectrometric Study of Cyclosporin Metabolites," *Rapid Communication in Mass Spectrometry* 12(16):1085-1091 (1998).

Vedejs et al., "Solution-Phase Synthesis of a Hindered N-Methylated Tetrapeptide Using Bts-Protected Amino Acid Chlorides: Efficient Coupling and Methylation Steps Allow Purification by Extraction," *Journal of Organic Chemistry* 65(8):2309-2318 (2000).

Wei et al., "Synthesis of Neurotrophic Activity of Nonimmunosuppressant Cyclosporin A Derivatives," *Bioorganic & Medicinal Chemistry Letters* 14(17):4549-4551 (2004).

Wenger et al., "Cyclosporine: Chemistry, Structure-Activity Relationships and Mode of Action," *Progress in Clinical Biochemistry and Medicine* 3:157-191 (1986).

Wenger et al., "Structure of Cyclosporine and its Metabolites: Total Synthesis of Cyclosporine Metabolites Formed by Oxidation at Positions 4 and 9 of Cyclosporine. Preparation of Leucine-4-Cyclosporine, (γ-hydroxy)-N-Methylleucine-9-Cyclosporine and Leucine-4-(γ-hydroxy)-N-Methylleucine-9-Cyclosporine," *Chimia* 46(7-8):314-322 C (1992).

Wenger, "Synthesis of Ciclosporin and Analogs: Structural and Conformational Requirements for Immunosuppressive Activity," *Progress in Allergy* 38(Ciclosporin):46-64 (1986).

Wenger, "Synthesis of Cyclosporin and Analogs: Structure, Activity, Relationships of New Cyclosporin Derivatives," *Transplantation Proceedings* 15(4, Suppl. 1-2)2230-2241 (1983).

Wu et al., "Preparation of Cyclosporin A Immunogen," *Journal of Chinese Pharmaceutical Sciences* 11(3):78-82 (2002).

Yamada et al., "Single-Step N-Methylation of Hindered Peptides: Total Synthesis of Cyclosporin O," *Peptide Science* 41:591-594 Volume Date 2004, (2005).

Paeshuyse et al., "Potent and Selective Inhibition of Hepatitis C Virus Replication by the Non-Immunosuppressive Cyclosporin Analogue DEBIO-025," *Antiviral Research* 65(3):A41 (2005).

Nakagawa et al., "Specific Inhibition of Hepatitis C Virus Replication by Cyclosporin A," *Biochem. Biophys. Res. Commun.* 313:42-47 (2004).

Inoue et al., "Combined Interferon α2b and Cyclosporin A in the Treatment of Chronic Hepatitis C: Controlled Trial," *J. Gastroenterol.* 38:567-572 (2003).

Bandera et al., "Immunomodulants in HIV Infection," *Expert Opin. Ther. Patents* 15(9):1115-1131 (2005).

Bartz et al., "Inhibition of Human Immunodeficiency Virus Replication by Non-Immunosuppressive Analogs of Cyclosporin A," *Proc. Natl. Acad. Sci. USA* 92:5381-5385 (1995).

Prelog et al., "Treatment of Psoriatic Arthritis with Cyclosporin A," *Acta Dermatovenerologica, Alpina, Pannonica et Adriatica*, 9(3):1-5 (2000).

The Merck Manual online version, www.merck.com/mmhe, Common Cold, pp. 1-3 (Oct. 27, 2004).

The Merck Manual online version, www.merck.com/mmhe, Viral Infections, pp. 1-4 (Mar. 20, 2005).

Rosenwirth et al., "Debio-025, A Novel Non-Immunosuppressive Cyclosporine Analog with Potent Anti-Human Immunodeficiency Virus Type 1 Activity: Pharmacological Properties and Mode of Action," *Research*, 64(3):42-43 (2005).

DEB 025, ADIS Database, pp. 1-2 (Oct. 12, 2005).

\* cited by examiner

CYCLOSPORIN ANALOGUES AND THEIR PHARMACEUTICAL USES

This application claims the benefit of U.S. Provisional Patent Application Ser. No. 60/614,266, filed Sep. 29, 2004, which is hereby incorporated by reference in its entirety.

FIELD OF THE INVENTION

The present invention discloses novel cyclosporin analogues and their utilities as immunosuppressive agents and as pharmaceutical agents for treatment of other diseases. Methods for preparation of such analogues are also disclosed.

BACKGROUND OF THE INVENTION

Cyclosporin A (CsA), a neutral cyclic undecapeptide isolated from the fungus *Tolypocladium inflatum* and currently marketed as Neoral® and Sandimmune® (Novartis, Basel, Switzerland), has been widely used for the prevention of organ transplant rejection. Cyclosporin A exerts its immunosuppressive effect at the molecular level by binding to the cyclophilin peptidyprolyl cis/trans isomerase. The resulting complex of cyclosporin A and cyclophilin binds to calcineurin, a $Ca^{2+}$/calmodulin-dependent phosphatase, and inhibits its phosphatase activity. Calcineurin regulates the translocation of the transcription factor nuclear factor of activated T-cell (NFAT) and the subsequent expression of early genes necessary for T-cell proliferation. Inhibition of the phosphatase activity of calcineurin by the cyclosporin A-cyclophilin complex prevents NFAT nuclear localization and suppresses the expression of genes like IL-2, ultimately leading to immunosuppression (Matsuda et al., "Mechanisms of Action of Cyclosporin," *Immunopharmacology*, 47:119-125 (2000)).

Cyclosporin A also has potential therapeutic application in the treatment of autoimmune diseases such as rheumatoid arthritis, Crohn's disease, psoriasis, and chronic inflammatory diseases, such as asthma. Unfortunately, clinical utility for these indications has not been realized because of the side effects such as nephrotoxicity, hypertension, hepatotoxicity, anaemia, and gastrointestinal intolerance that occur with clinically effective doses of cyclosporin A. The toxicity associated with cyclosporin A is believed by many experts working in the immunosuppression therapeutic area to be mechanism based (Lazarova et al., "Cyclosporin A Analogues: Recent Advances," *Expert Opin. Ther. Patents*, 13:1327-1332 (2003)). Indeed, the goal of discovering novel cyclosporin analogues with improved therapeutic index has yet to be achieved despite the significant efforts in this drug discovery area over the last three decades (U.S. Pat. No. 5,525,590 to Bollinger et al.; U.S. Pat. No. 5,643,870 to Boelsterli et al.; U.S. Pat. No. 5,639,852 to Rich et al.; U.S. Pat. No. 5,236,899 to Durette; U.S. Pat. No. 5,122,511 to Patchett et al.; U.S. Pat. No. 4,914,188 to Dumont et al.; U.S. Pat. No. 4,771,122 to Seebach; U.S. Pat. No. 4,764,503 to Wenger; U.S. Pat. No. 4,396,542 to Wenger; U.S. Pat. No. 4,210,581 to Ruegger et al.).

More recent efforts to find novel cyclosporin analogues with potent immunosuppressive activity and decreased toxicity are underway and have led to compounds such as $ISA_{TX}247$. Preclinical observations indicate that $ISA_{TX}247$ has the potential to be significantly more potent and less toxic than other immunosuppressants in its class already available on the market for the prevention of transplant rejection. $ISA_{TX}247$ is in phase II clinical trials for the prevention of organ rejection after transplantation and for the treatment of psoriasis (Abel et al., "$ISA_{TX}247$: A Novel Calcineurin Inhibitor," *J. Heart Lung Transplant*, 20:161 (2001); Aspeslet et al., "$ISA_{TX}247$: A Novel Calcineurin Inhibitor," *Transplantation Proceedings*, 33:1048-1051 (2001); U.S. Pat. Nos. 6,605,593 and 6,613,739 to Naicker et al.).

A "soft" drug approach (Lazarova et al., "Synthesis and Biological Evaluation of Cyclosporin A Analogues: Potential Soft Drugs for the Treatment of Autoimmune Diseases," *J. Med. Chem.*, 46:674-676 (2003)) has also recently been described that seeks to minimize the toxicity of immunosuppressive cyclosporin A derivatives used for the treatment of autoimmune diseases (International Patent Publication No. WO 03/033010 to Or et al.) and respiratory diseases, such as asthma (International Patent Publication No. WO 02/069902 to Or et al.).

There is still a large need for novel cyclosporin analogues with improved therapeutic index.

The present invention is directed to achieving these objectives.

SUMMARY OF THE INVENTION

The compounds of the present invention are represented by Formula Ia, as shown below:

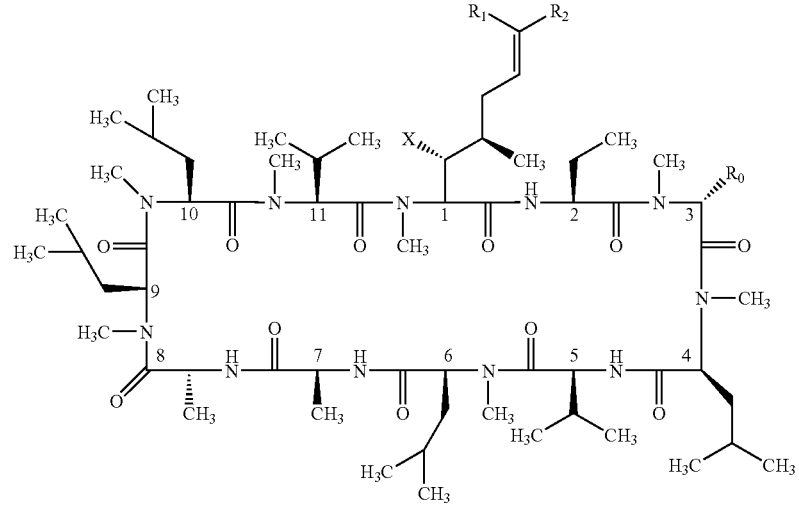

Formula Ia where:
X is OH or OAc;
$R_0$ is H or $CH_2OR_3$;
$R_1$ is H or D;
$R_2$ is selected from the group consisting of:
   halogen,
   $C_1$-$C_6$ halogenated saturated straight or branched carbon chain,
   $C_2$-$C_6$ halogenated unsaturated straight or branched carbon chain,
   $C_3$-$C_6$ substituted and unsubstituted cycloalkyl,
   $C_1$-$C_6$ saturated straight or branched carbon chain containing amino group,
   —CH=N—$OR_4$, and
   —CH=N—$NR_4R_5$;
$R_3$ is selected from the group consisting of:
   hydrogen,
   alkanoyl,
   alkenoyl,
   alkynoyl,
   aryloyl,
   arylalkanoyl,
   alkylaminocarbonyl,
   arylaminocarbonyl,
   arylalkylaminocarbonyl,
   alkyloxycarbonyl,
   aryloxycarbonyl,
   arylalkyloxycarbonyl,
   alkylsulfonyl, and
   arylsulfonyl; and
$R_4$ together with $R_5$ results in the formation of a cyclic moiety of $C_2$-$C_6$ optionally containing heteroatom or heteroatoms, wherein the compound is a cis geometric isomer, a trans geometric isomer, or a mixture of the cis and the trans geometric isomers or a pharmaceutically acceptable salt thereof.

The compounds of the present invention are also represented by Formula Ib, as shown below:

Formula Ib where:
X is OH or OAc;
$R_0$ is H or $CH_2OR_3$;
$R_1$ is halogen;
$R_2$ is selected from the group consisting of:
   hydrogen,
   deuterium,
   halogen,
   $C_1$-$C_6$ saturated straight or branched carbon chain, optionally containing halogen,
   $C_2$-$C_6$ unsaturated straight or branched carbon chain, optionally containing halogen,
   $C_3$-$C_6$ substituted and unsubstituted cycloalkyl,
   substituted and unsubstituted aryl, and
   substituted and unsubstituted heteroaryl; and
$R_3$ is selected from the group consisting of:
   hydrogen,
   alkanoyl,
   alkenoyl,
   alkynoyl,
   aryloyl,
   arylalkanoyl,
   alkylaminocarbonyl, $R_4$ and $R_5$ are the same or different and independently selected from the group consisting of:
   hydrogen,
   $C_1$-$C_6$ saturated straight or branched carbon chain,
   $C_3$-$C_6$ unsaturated straight or branched carbon chain,
   $C_3$-$C_6$-substituted and unsubstituted cycloalkyl,
   $C_1$-$C_4$ carbon chain containing an aryl or heteroaryl,
   substituted and unsubstituted aryl,
   substituted and unsubstituted heteroaryl,
   alkanoyl,
   alkenoyl,
   alkynoyl,
   aryloyl, arylaminocarbonyl,
arylalkylaminocarbonyl,
alkyloxycarbonyl,
aryloxycarbonyl, and
arylalkyloxycarbonyl, wherein the compound is a cis geometric isomer, a trans geometric isomer, or a mixture of the cis and the trans geometric isomers or a pharmaceutically acceptable salt thereof.

The present invention discloses novel cyclosporin derivatives that are chemically modified from cyclosporin A. In particular, the present invention discloses cyclosporin analogues containing a chemically modified side chain at the position one amino acid and optionally a substitution at the position three amino acid of cyclosporin A.

The present invention discloses novel cyclosporin analogues which are effective as immunosuppressive agents. The compounds of the present invention possess immunosuppressive activity similar to or more potent than cyclosporin A. These compounds also possess utility in the treatment of ocular allergy and dry eye, as well as autoimmune and chronic inflammatory diseases, such as asthma, rheumatoid arthritis, multiple sclerosis, psoriasis, and ulcerative colitis.

DETAILED DESCRIPTION OF THE INVENTION

Figure 1:
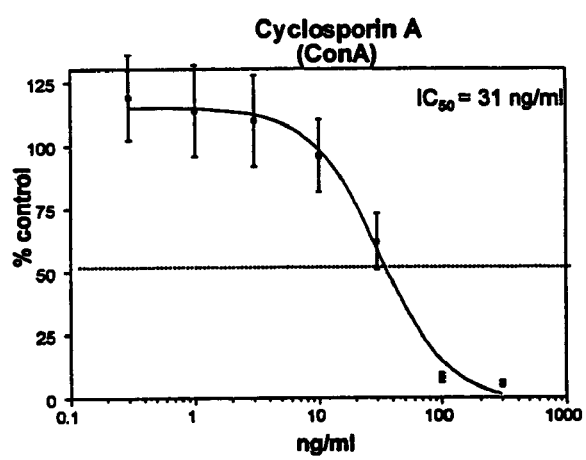
FIG. 1 depicts the results from a concanavalin A (ConA)-stimulated splenocyte assay, where the novel cyclosporin analogue compounds of the present invention (disclosed in Examples 9 and 11) are shown to possess enhanced potency in immunosuppression, compared to cyclosporin A.
Figure 1:
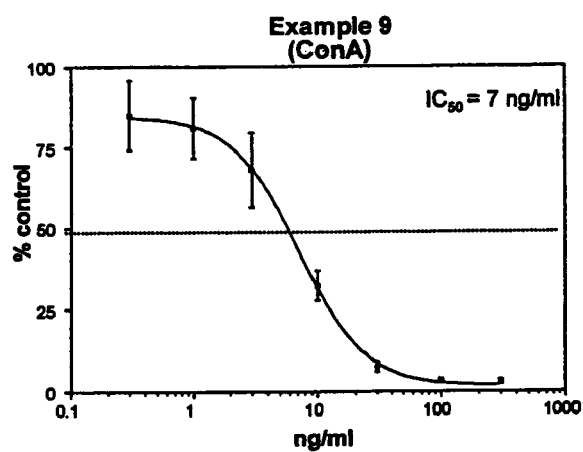
Figure 1:
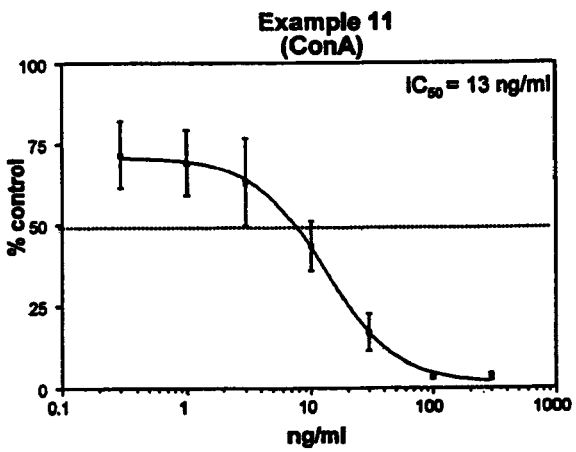

The present invention provides novel cyclosporin analogue compounds represented by Formula Ia, as shown below:

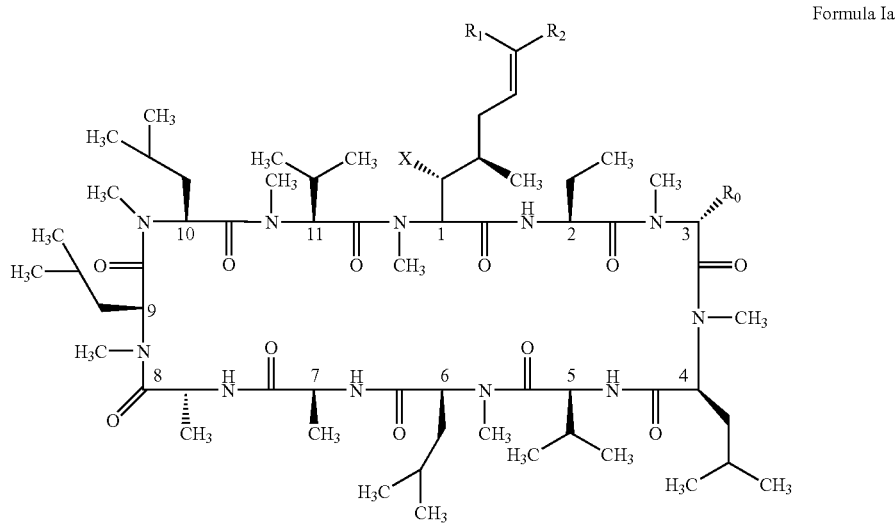

Formula Ia where:
X is OH or OAc;
$R_0$ is H or $CH_2OR_3$;
$R_1$ is H or D;
$R_2$ is selected from the group consisting of:
  halogen,
  $C_1$-$C_6$ halogenated saturated straight or branched carbon chain,
  $C_2$-$C_6$ halogenated unsaturated straight or branched carbon chain,
  $C_3$-$C_6$ substituted and unsubstituted cycloalkyl,
  $C_1$-$C_6$ saturated straight or branched carbon chain containing amino group,
  —CH=N—$OR_4$, and
  —CH=N—$NR_4R_5$;
$R_3$ is selected from the group consisting of:
  hydrogen,
  alkanoyl,
  alkenoyl,
  alkynoyl,
  aryloyl,
  arylalkanoyl,
  alkylaminocarbonyl,
  arylaminocarbonyl,
  arylalkylaminocarbonyl,
  alkyloxycarbonyl,
  aryloxycarbonyl, and
  arylalkyloxycarbonyl;
$R_4$ and $R_5$ are the same or different and independently selected from the group consisting of:
  hydrogen,
  $C_1$-$C_6$ saturated straight or branched carbon chain,
  $C_3$-$C_6$ unsaturated straight or branched carbon chain,
  $C_3$-$C_6$-substituted and unsubstituted cycloalkyl,
  $C_1$-$C_4$ carbon chain containing an aryl or heteroaryl,
  substituted and unsubstituted aryl,
  substituted and unsubstituted heteroaryl,
  alkanoyl,
  alkenoyl,
  alkynoyl,
  aryloyl,
  arylalkanoyl,
  alkylaminocarbonyl,
  arylaminocarbonyl,
  arylalkylaminocarbonyl,
  alkyloxycarbonyl,
  aryloxycarbonyl,
  arylalkyloxycarbonyl,
  alkylsulfonyl, and
  arylsulfonyl; and
$R_4$ together with $R_5$ results in the formation of a cyclic moiety of $C_2$-$C_6$ optionally containing heteroatom or heteroatoms, wherein the compound is a cis geometric isomer, a trans geometric isomer, or a mixture of the cis and the trans geometric isomers or a pharmaceutically acceptable salt thereof.

One embodiment of the present invention relates to the above compound of Formula Ia, where: X=OH or OAc; $R_0$=H, $CH_2OH$, or $CH_2OAc$; $R_1$=H or D; and $R_2$=F, Cl, Br, or I.

Another embodiment of the present invention relates to the above compound of Formula Ia, where: X=OH or OAc; $R_0$=H, $CH_2OH$, or $CH_2OAc$; $R_1$=H or D; and $R_2$=$CF_3$, $CH_2F$, or $CH_2Cl$.

Another embodiment of the present invention relates to the above compound of Formula Ia, where: X=OH or OAc; $R_0$=H, $CH_2OH$, or $CH_2OAc$; $R_1$=H or D; and $R_2$=—CH═CHF, —CH═CHCl, —CH═CHBr, or —CH═CHI.

Another embodiment of the present invention relates to the above compound of Formula Ia, where: X=OH or OAc; $R_0$=H, $CH_2OH$, or $CH_2OAc$; $R_1$=H or D; and $R_2$=—CH═CH—C≡CH, —CH═CH—C≡C—$CH_3$, or —CH═CH—C≡C—CH═$CH_2$.

Another embodiment of the present invention relates to the above compound of Formula Ia, where: X=OH or OAc; $R_0$=H, $CH_2OH$, or $CH_2OAc$; $R_1$=H or D; and $R_2$ is cyclopropyl.

Another embodiment of the present invention relates to the above compound of Formula Ia, where: X=OH or OAc; $R_0$=H, $CH_2OH$, or $CH_2OAc$; $R_1$=H or D; and $R_2$=—CH═N—OH, —CH═N—$OCH_3$, —CH═N—$OCH_2CH_3$, —CH═N—$NHCH_3$, or —CH═N—N($CH_3$)$_2$.

Another embodiment of the present invention relates to the above compound of Formula Ia, where:
X=OH or OAc,
$R_0$=H,
$R_1$=H or D, and
$R_2$=Cl, Br, I, $CF_3$, $C_3F_7$, $C_4F_9$, $CH_2F$, $CH_2Cl$, -cyclopropyl, —CH═CHCl, —CH═CHBr, —CH═CHI, —CH═$CHCF_3$, —C($CF_3$)═$CH_2$, —C≡$CC_4H_9$, —CH═CH—C≡CH, —CH═CH—C≡$CCH_3$, —CH═CH—C≡CSi($CH_3$)$_3$, —CH═CH—C≡C—CH═$CH_2$, —CH═CH—C≡C—CH(OH)$CH_3$, —$CH_2NHCH_3$, —$CH_2N(CH_3)_2$, —$CH_2N(CH_3)$(Ac), —$CH_2$-pyrrolidine, —$CH_2$-piperidine, —$CH_2$-morpholine, —$CH_2$-thiomopholine, —$CH_2$-methylpiperizine, —CH═N—OH, —CH═N—$OCH_3$, —CH═N—$OCH_2CH_3$, —CH═N—$OCH_2CH$═$CH_2$, —CH═N—$OCH_2Ph$, —CH═N—N($CH_3$)$_2$, —CH═N—$NHCH_3$, or —CH═N—$NHSO_2C_6H_4CH_3$.

Another embodiment of the present invention relates to the above compound of Formula Ia, where:
X=OH or OAc,
$R_0$=$CH_2OH$ or $CH_2OAc$,
$R_1$=H, and
$R_2$=Cl, Br, I, $CF_3$, $CH_2F$, Ph, —CH═CHCl, —CH═CHBr, —CH═CHI, —CH═$CH_2$, or —CH═$CD_2$.

In addition, the compounds of the present invention are represented by Formula Ib, as shown below:

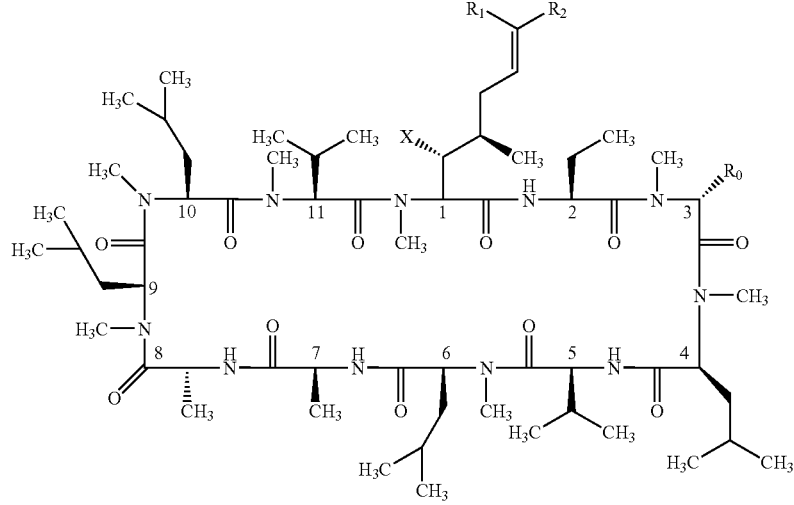

Formula Ib where:
X is OH or OAc;
$R_0$ is H or $CH_2OR_3$;
$R_1$ is halogen;
$R_2$ is selected from the group consisting of:
  hydrogen,
  deuterium,
  halogen,
  $C_1$-$C_6$ saturated straight or branched carbon chain, optionally containing halogen,
  $C_2$-$C_6$ unsaturated straight or branched carbon chain, optionally containing halogen,
  $C_3$-$C_6$ substituted and unsubstituted cycloalkyl,
  substituted and unsubstituted aryl, and
  substituted and unsubstituted heteroaryl; and
$R_3$ is selected from the group consisting of:
  hydrogen,
  alkanoyl,
  alkenoyl,
  alkynoyl,
  aryloyl,
  arylalkanoyl,
  alkylaminocarbonyl,
  arylaminocarbonyl,
  arylalkylaminocarbonyl,
  alkyloxycarbonyl,
  aryloxycarbonyl, and
  arylalkyloxycarbonyl, wherein the compound is a cis geometric isomer, a trans geometric isomer, or a mixture of the cis and the trans geometric isomers or a pharmaceutically acceptable salt thereof.

Another embodiment of the present invention relates to the compound of Formula Ib, where:
X=OH or OAc,
$R_0$=H,
$R_1$=Cl, and
$R_2$=H, D, Cl, $CF_3$, or Ph.

Another embodiment of the present invention relates to the compound of Formula Ib, where:
X=OH or OAc,
$R_0$=H,
$R_1$=Br or I, and
$R_2$=H, D, or $CH_3$.

In particular, the present invention relates to novel halogenated cyclosporin analogues, including cyclosporin vinyl halides and allylic halides.

The present invention also discloses methods for preparation of novel cyclosporin analogue compounds represented by Formula Ia and Formula Ib and their utility as pharmaceutical agents for treatment of various diseases. The present invention also describes the utility of halogenated cyclosporin analogues (vinyl halides and allylic halides) as synthetic intermediates that can be transformed into additional novel cyclosporin derivatives.

The starting material for the preparation of the compounds of the present invention is cyclosporin A. The structure of cyclosporin A, a cycloundecapeptide, and the position numbering for each amino acid in the ring is shown below:

The novel cyclosporin analogues of the present invention are derived from cyclosporin A or a key intermediate prepared by modification at the position three amino acid of cyclosporin A. As shown in Scheme 1, such a key intermediate (Formula IIb) can be prepared by deprotonation of cyclosporin A with lithium diisopropylamide (LDA), followed by treatment with formaldehyde (Seebach et al, "Modification of Cyclosporin A: Generation of an Enolate at the Sarcosine Residue and Reaction With Electrophiles," *Helv. Chim. Acta*, 76:1564-1590 (1993), which is hereby incorporated by reference in its entirety).

Scheme 1

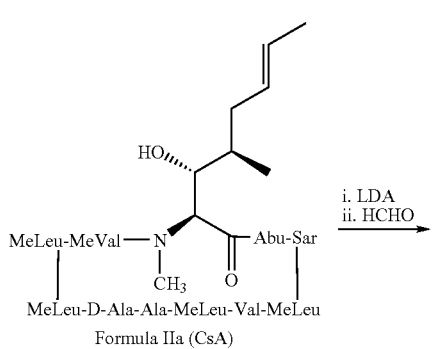

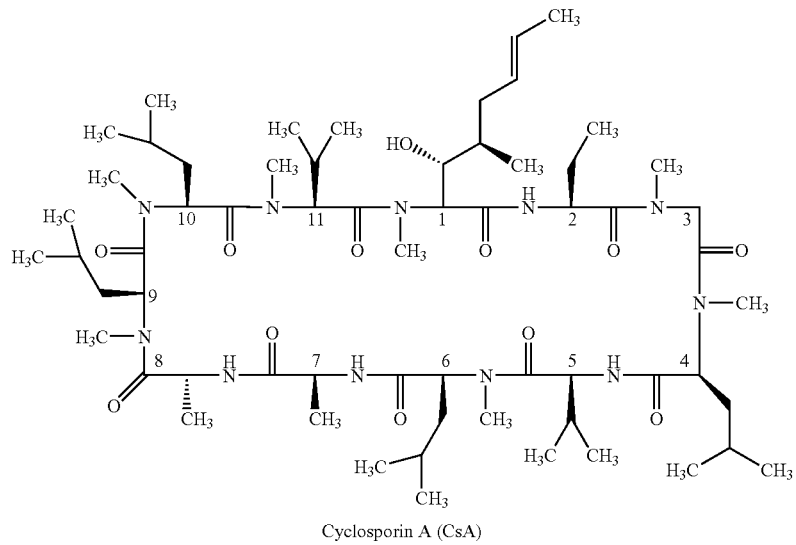

Cyclosporin A (CsA)

Cyclosporin A can also be represented by Formula IIa, as shown below:

Formula IIa

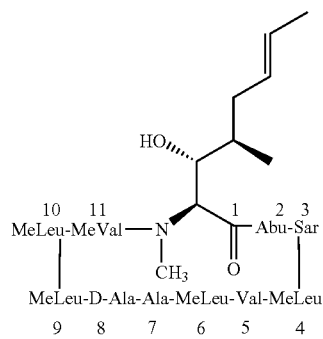

-continued

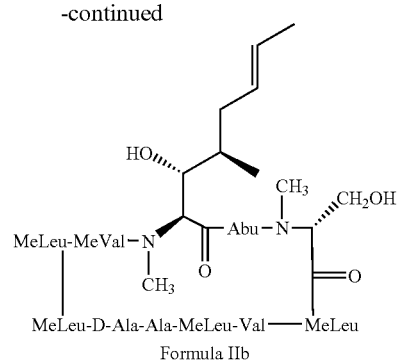

Formula IIb

According to one embodiment of the present invention, novel cyclosporin vinyl halides can be prepared by employing Takai reaction as a key step, as outlined in Scheme 2. Acetylation of cyclosporin A (Formula IIa) or cyclosporin diol intermediate of Formula IIb with acetic anhydride, followed by oxidative cleavage of the double bond with ozone, generates cyclosporin aldehyde of Formula III smoothly. Treatment of the cyclosporin aldehyde with haloform-$CrCl_2$ complex affords novel cyclosporin vinyl halides of Formula Ia (Takai et al, "Simple and Selective Method for RCHO→(E)-RCH=CHX Conversion by Means of a $CHX_3$—$CrCl_2$ System," *J. Am. Chem. Soc.*, 108:7408-7410 (1986), which is hereby incorporated by reference in its entirety). Various haloforms, such as chloroform, bromoform, and iodoform can be applied. Usage of excess haloform and $CrCl_2$ seems to be necessary to obtain the desired vinyl halide in good to excellent yield (50-80%). This stereoselective chemistry provided a halogenated olefin of Formula Ia in exclusively the trans-configuration ($R_1$=H or D; $R_2$=halogen). The acetyl protection group(s) can be removed by treatment with potassium carbonate in methanol (see Scheme 2).

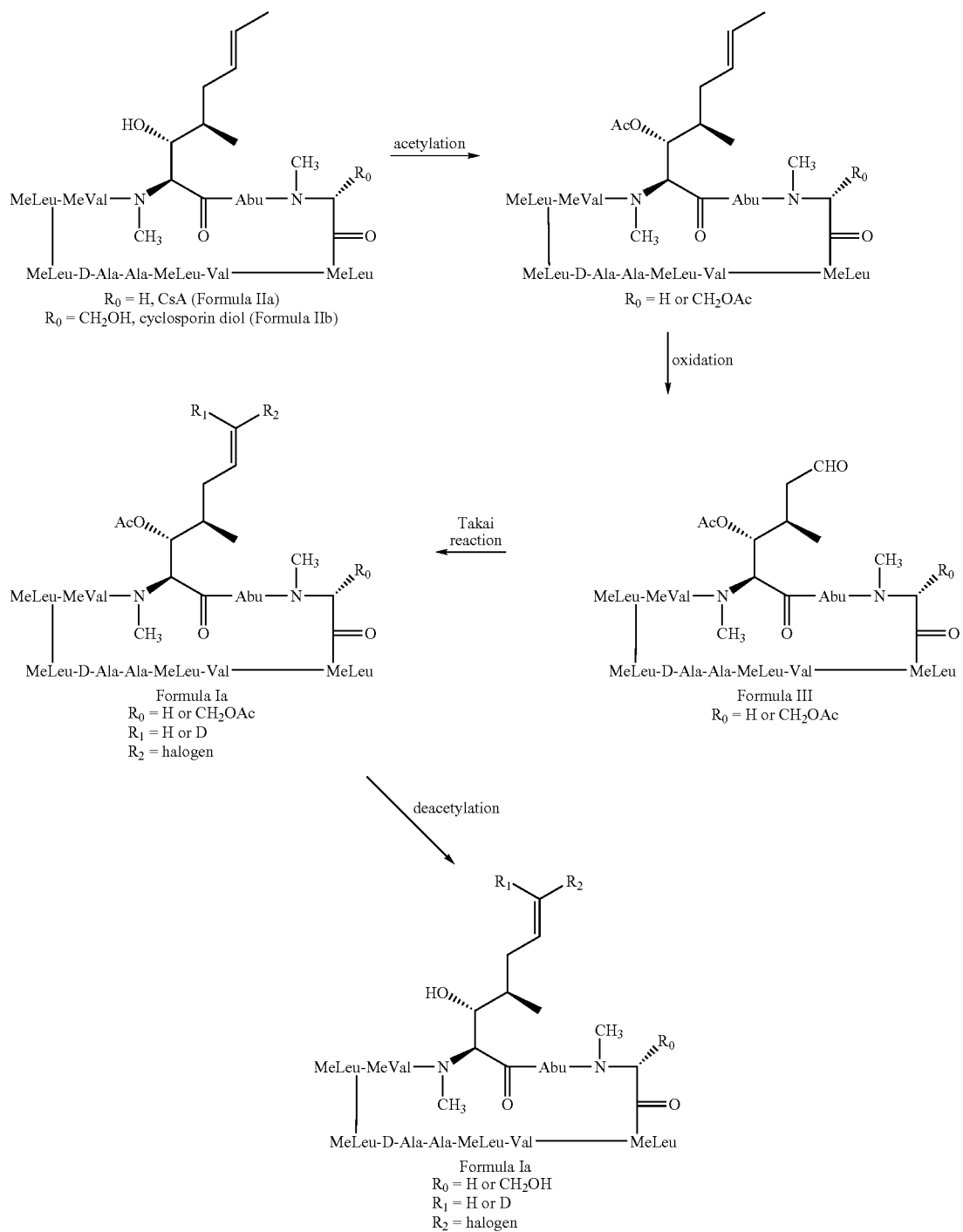

Scheme 2

The novel cyclosporin vinyl halides of Formula Ib in the present invention can be prepared via an alternative approach by application of phosphorous ylide chemistry (Wittig reaction, Horner-Emmons reaction, or other modified Wittig conditions), as shown in Scheme 3. This chemistry converts the cyclosporin aldehyde of Formula III to the halogenated olefin of Formula Ib effectively. The reaction generates either the cis-isomer of the olefin or a separable mixture of cis- and trans-isomers. Typically, the phosphorous ylide species under Wittig, Horner-Emmons, or other modified Wittig conditions are generated by treatment of various phosphonium salts or phosphonates with a strong base, such as n-butyllithium or sodium bis(trimethylsilyl)amide. The deacetylation is conducted under the same conditions as described in Scheme 2.

Scheme 3

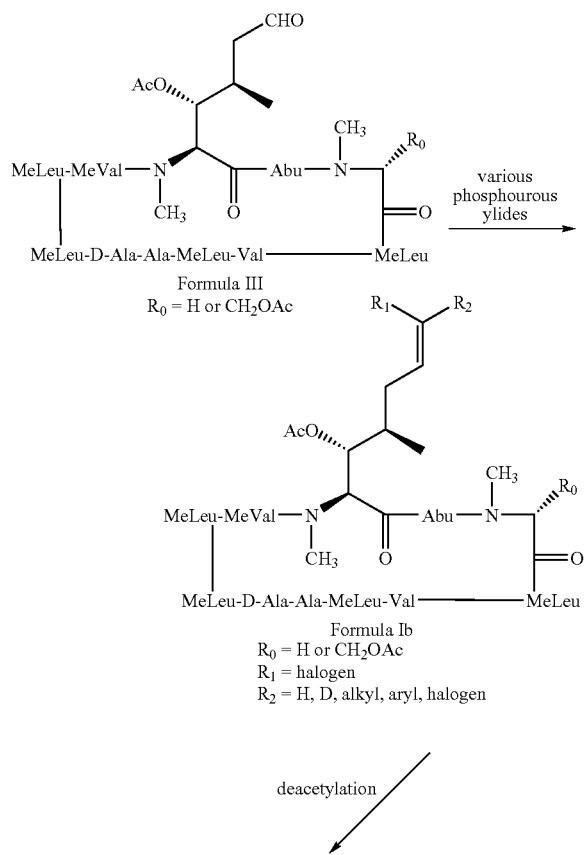

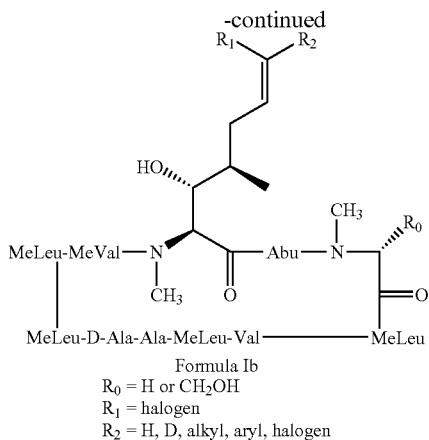

Formula Ib
R₀ = H or CH₂OH
R₁ = halogen
R₂ = H, D, alkyl, aryl, halogen

Utilizing the same strategy described in Scheme 2, halogenated cyclosporin diene can be prepared via a Takai reaction with α,β-unsaturated aldehyde of Formula IV, which is generated by application of olefin cross metathesis on cyclosporin (Scheme 4). In the last decade, ruthenium catalyzed olefin metathesis has emerged as a powerful synthetic tool for the formation of carbon-carbon bonds (Chatterjee et al, "A General Model for Selectivity in Olefin Cross Metathesis," *J. Am. Chem. Soc.*, 125:11360-11370 (2003); Connon et al, "Recent Development in Olefin Cross Metathesis," *Angew. Chem. Int. Ed.*, 42:1900-1923 (2003), which are hereby incorporated by reference in their entirety). There are three main variations on olefin metathesis: (a) cross metathesis; (b) ring opening/close metathesis; and (c) intermolecular enyne metathesis. As an acyclic carbon-carbon bond-forming method, olefin cross metathesis has numerous advantages: (1) the process is catalytic (typically 1-5 mol % of catalyst required); (2) high yield can be obtained under mild conditions in a relatively short reaction time; (3) a wide range of functional groups are tolerated, with minimal substrate protection necessary; and (4) the reaction is relatively atom-economic, and gaseous ethylene is usually the only byproduct, which is an important consideration in industrial applications (Connon et al, "Recent Development in Olefin Cross Metathesis," *Angew. Chem. Int. Ed.*, 42:1900-1923 (2003), which is hereby incorporated by reference in its entirety).

Scheme 4

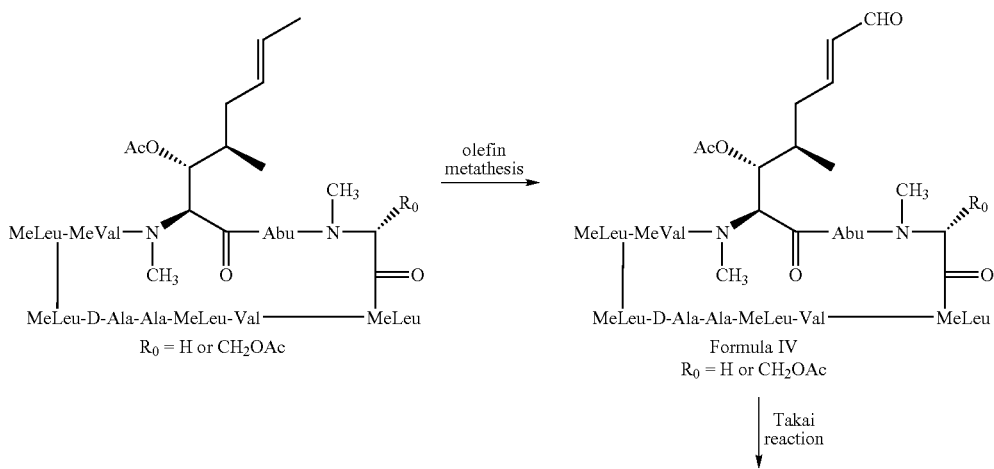

-continued

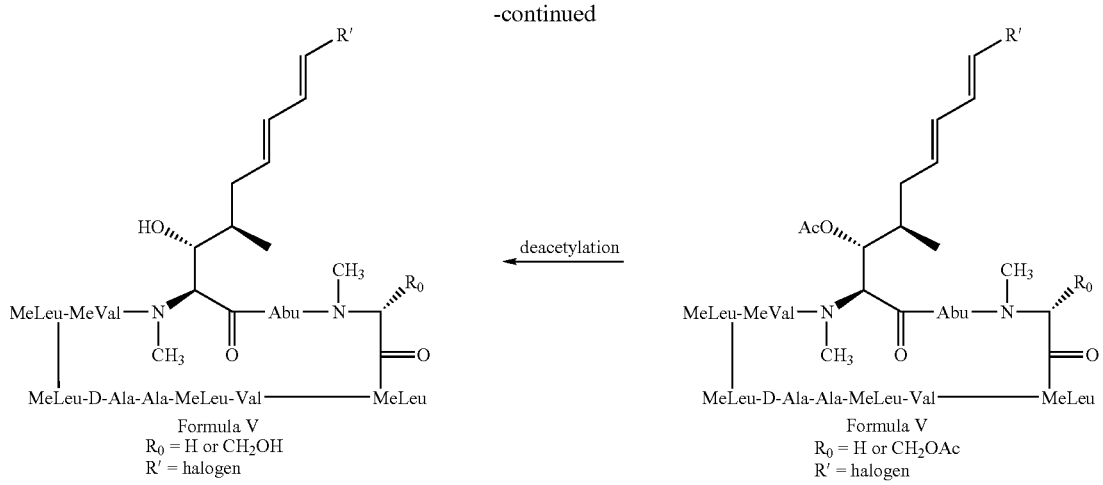

Formula V
$R_0 = H$ or $CH_2OH$
$R' =$ halogen

Formula V
$R_0 = H$ or $CH_2OAc$
$R' =$ halogen

As shown in Scheme 4, olefin cross metathesis of acetyl-protected cyclosporin A or cyclosporin diol is carried out with acrolein acetals (such as acrolein dimethyl acetal and 2-vinyl-1,3-dioxolane) in the presence of Grubbs' catalyst in methylene chloride or toluene. The reaction provides an acetal intermediate which is hydrolyzed during purification by high pressure liquid chromatography, using acetonitrile-water-trifluoroacetic acid as a solvent system to afford trans-α,β-unsaturated aldehyde of Formula IV directly in good to excellent yield (60-80%). The catalyst can be either Grubbs' catalyst $2^{nd}$ generation (Schwab et al, "A Series of Well-Defined Metathesis Catalysts-Synthesis of [RuCl$_2$(=CHR') (PR$_3$)$_2$] and Its Reactions," *Angew. Chem. Int. Ed.*, 34:2039-2041 (1995), which is hereby incorporated by reference in its entirety) or Hoveyda-Grubbs catalyst (Scholl et al, "Synthesis and Activity of a New Generation of Ruthenium-Based Olefin Metathesis Catalysts Coordinated with 1,3-Dimesityl-4,5-dihydroimidazol-2-ylidene Ligands," *Org. Lett.*, 1:953 (1999); Sanford et al, "Mechanism and Activity of Ruthenium Olefin Metathesis Catalysts," *J. Am. Chem. Soc.*, 123: 6543-6554 (2001), which are hereby incorporated by reference in their entirety). This stereoselective chemistry provides an α,β-unsaturated aldehyde of Formula IV exclusively in the trans-geometric isomer.

Treatment of α,β-unsaturated aldehyde of Formula IV with haloform and CrCl$_2$ in tetrahydrofuran provides a halogenated cyclosporin diene of Formula V as a trans-isomer. Only a small amount of cis-isomer is observed under these conditions. Finally, acetyl protection group(s) can be removed with potassium carbonate in methanol (Scheme 4).

According to another embodiment of the present invention, cyclosporin vinyl halides can be used as powerful synthetic intermediates for palladium or nickel-catalyzed couplings (such as Stille coupling, Suzuki coupling, Negishi coupling, and Sonogashira coupling) to build a new carbon-carbon bond. As shown in Scheme 5, Stille coupling of the cyclosporin vinyl iodide of Formula VI with organotin reagents, in the presence of Pd(CH$_3$CN)$_2$Cl$_2$, affords a novel cyclosporin cyclopropyl derivative and a diene analogue respectively, while Sonogashira coupling with alkyne provides enyne analogue. Similar reactions can be performed on the halogenated diene of Formula V with organotin reagents, organozinc reagents, boronic acids, or alkynes to prepare novel cyclosporin analogues.

Scheme 5

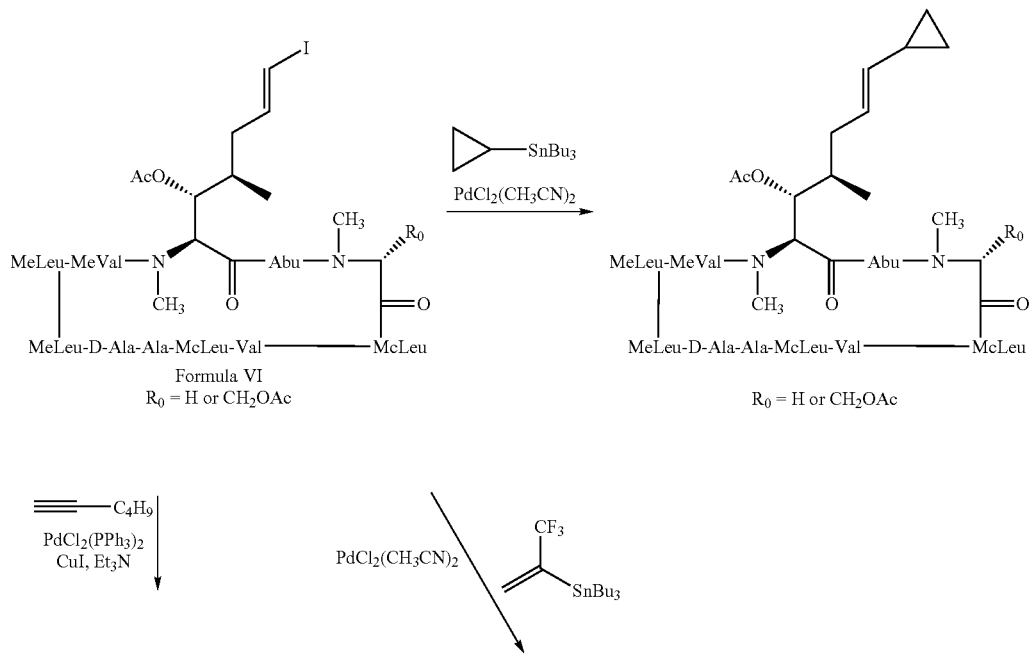

-continued

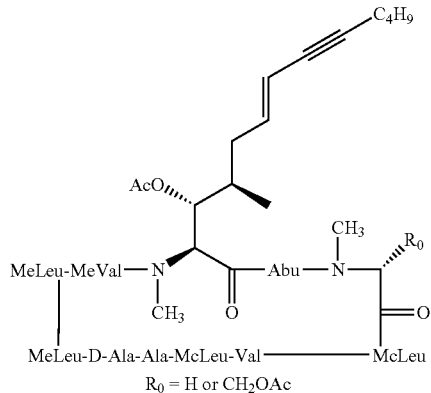

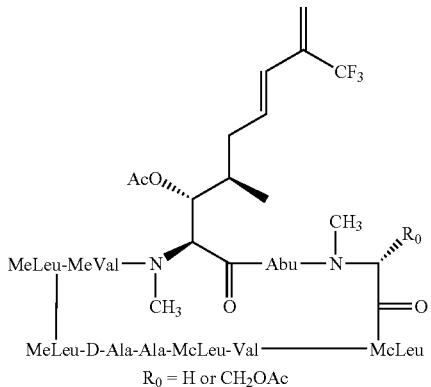

According to another embodiment of the present invention, cyclosporin allylic halides can be prepared via olefin cross metathesis with a Grubbs catalyst, as shown in Scheme 6. Utilizing an allylic chloride of Formula VII as a key intermediate, various cyclosporin amine derivatives can be obtained.

Another embodiment of the present invention relates to a so-called "soft drug" strategy (Lazarova et al., "Synthesis and Biological Evaluation of Novel Cyclosporin A Analogues: Potential Soft Drugs for the Treatment of Autoimmune Diseases," *Journal of Medicinal Chemistry*, 46:674-676 (2003);

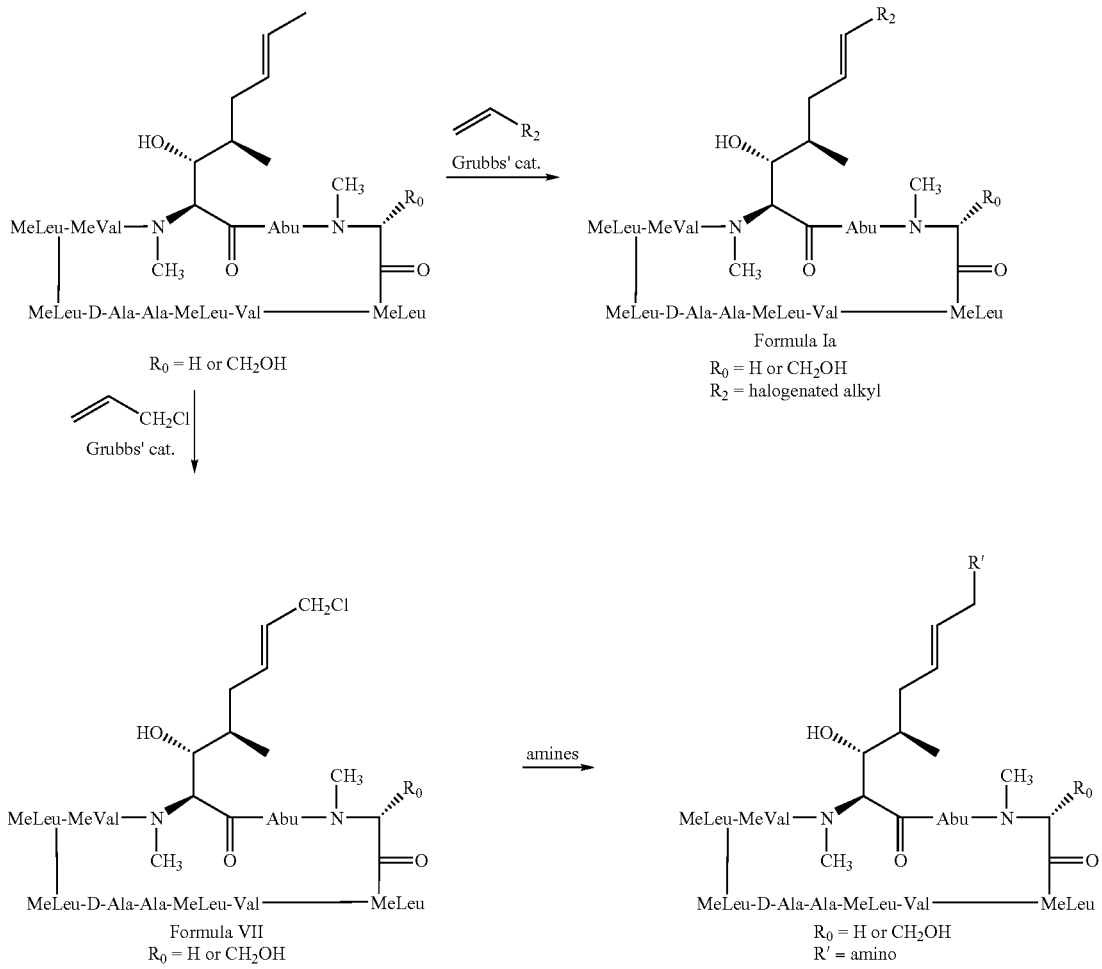

Little et al., "Soft Drugs Based on Hydrocortisone: The Inactive Metabolite Approach and Its Application to Steroidal Anti-inflammatory Agents," *Pharm. Res.*, 16:961-967 (1999), which are hereby incorporated by reference in their entirety). Incorporation of a C=N bond leads to the preparation of α,β-unsaturated oximes (C=N—OR) and hydrazones (C=N—NR$_2$) of Formula VIII. The active α,β-unsaturated oximes (C=N—OR) and hydrazones (C=N—NR$_2$) of the present invention can be hydrolyzed and inactivated under physiological conditions. Therefore, the C=N moiety of the novel cyclosporin analogues of Formula VIII provides a simple means to control the hydrolytic half-life of the soft drug, thus minimizing system exposure and toxicity. As shown in Scheme 7, the treatment of α,β-unsaturated aldehyde of Formula IV with hydroxylamines or alkyloxyamines (RONH$_2$) and hydrazines (R$_2$NNH$_2$) affords the corresponding α,β-unsaturated oximes (C=N—OR) and hydrazones (C=N—NR$_2$) of Formula VIII, respectively.

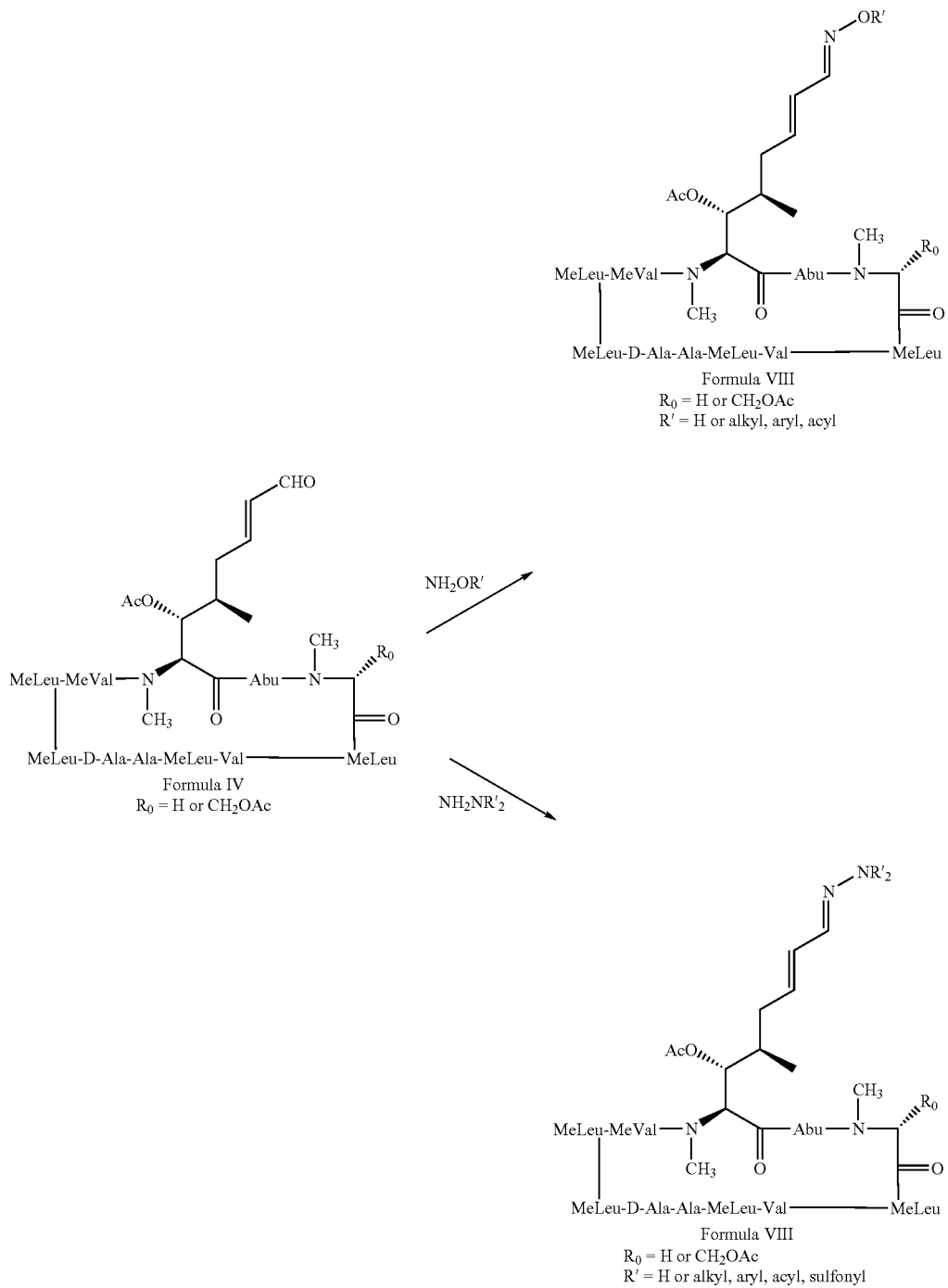

The compounds disclosed in the present invention are particularly useful as immunosuppressive agents. Administration of these compounds suppresses the immune response in organ transplant patients and, thus, prevents allograft rejection. The compounds of the present invention possess immunosuppressive activity similar to or more potent than cyclosporin A. For example, as shown in FIG. 1, the novel cyclosporin analogue compounds disclosed in Examples 9 and 11 possess enhanced potency in immunosupresion in the concanavalin A stimulated splenocyte assay, compared to cyclosporin A. Table 1 shows the immunosuppressive activities of several novel cyclosporin analogue compounds disclosed in the present application. (The third column in Table 1 contains cyclosporin A positive control values included for comparison.)

TABLE 1

Immunosuppressive Activities of Novel Cyclosporin Analogue Compounds of the Present Invention

| Example where the Novel Cyclosporin Analogue Compound is Disclosed | $IC_{50}$ (ng/mL) | $IC_{50}$ (ng/mL) of CsA |
|---|---|---|
| Example 5 | 22 | 25 |
| Example 6 | 11 | 25 |
| Example 9 | 7 | 31 |
| Example 11 | 13 | 31 |
| Example 19 | 9 | 6 |
| Example 26 | 5 | 9 |
| Example 31 | 38 | 8 |
| Example 34 | 12 | 5 |
| Example 56 | 15 | 31 |
| Example 58 | 42 | 31 |
| Example 67 | 7 | 6 |
| Example 69 | 4 | 9 |
| Example 71 | 8 | 6 |
| Example 72 | 5 | 6 |

The compounds disclosed in the present invention also possess utility in the treatment of autoimmune and chronic inflammatory diseases such as asthma, rheumatoid arthritis, multiple sclerosis, psoriasis, and ulcerative colitis, to name only a few.

In addition, the compounds disclosed in the present invention are useful for the treatment of ocular allergy and dry eye. Allergan is currently marketing a topical formulation of cyclosporin A called Restasis™ (cyclosporin ophthalmic emulsion) for the treatment of keratoconjunctivitis sicca or chronic dry eye syndrome in patients whose tear production is presumed to be suppressed due to ocular inflammation. While the exact mechanism of Restasis™ is unknown, it is thought to act as an immunomodulator with anti-inflammatory effects ("Annual Update 2003: Ophthalmic Drugs" *Drugs of the Future*, 28(3): 287-307 (2003); Clark et al., "Ophthalmic Drug Discovery," *Nature Reviews in Drug Discovery*, 2:448-459 (2003), which are hereby incorporated by reference in their entirety).

For treatment of the above-mentioned diseases, therapeutically effective doses of the compounds of the present invention may be administered orally, topically, parenterally, by inhalation spray, or rectally in dosage unit formulations containing conventional non-toxic pharmaceutically acceptable carriers, adjuvants, and vehicles. The term parenteral, as used herein, includes subcutaneous injections, intravenous, intramuscular, intrasternal injection, or infusion techniques.

The pharmaceutical compositions containing the active ingredient may be in the form suitable for oral use, for example, as tablets, troches, lozenges, aqueous or oily suspensions, dispersible powders or granules, emulsions, hard or soft capsules, or syrups or elixirs. The pharmaceutical compositions of the present invention contain the active ingredient formulated with one or more pharmaceutically acceptable carriers. As used herein, the term "pharmaceutical acceptable carrier" means a non-toxic, inert solid, semi-solid or liquid filler, diluent, encapsulating material, or formulation auxiliary of any type. Some examples of pharmaceutically acceptable carriers are sugars such as lactose, glucose, and sucrose; starches such as corn starch or potato starch; cellulose and its derivatives such as sodium carboxymethyl cellulose, ethyl cellulose, and cellulose acetate; powdered tragacanth; malt; gelatin; talc; excipients such as cocoa butter and suppository waxes; oils such as peanut oil, cottonseed oil, safflower oil, sesame oil, olive oil, corn oil, and soybean oil; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol; phosphate buffer solutions; non-toxic, compatible lubricants such as sodium lauryl sulfate and magnesium stearate; as well as coloring agents, releasing agents, sweetening, and flavoring and perfuming agents. Preservatives and antioxidants, such as ethyl or n-propyl p-hydroxybenzoate, can also be included in the pharmaceutical compositions.

Dosage forms for topical or transdermal administration of the compounds disclosed in the present invention include ointments, pastes, creams, lotions, gels, plasters, cataplasms, powders, solutions, sprays, inhalants, or patches. The active component is admixed under sterile conditions with a pharmaceutically acceptable carrier and any needed preservatives or buffers, as may be required. The ointments, pastes, creams and gels may contain, in addition to an active compound of the present invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

For nasal administration, the compounds disclosed in the present invention can be administered, as suitable, in liquid or powdered form from a nasal applicator. Forms suitable for ophthalmic use will include lotions, tinctures, gels, ointment and ophthalmic inserts, as known in the art. For rectal administration (topical therapy of the colon), compounds of the present invention may be administered in suppository or enema form, in solution in particular, for example in vegetable oil or in an oily system for use as a retention enema.

The compounds disclosed in the present invention may be delivered to the lungs by the inhaled route either in nebulizer form or as a dry powder. The advantage of the inhaled route, over the systemic route, in the treatment of asthma and other diseases of airflow obstruction and/or chronic sinusitis, is that patients are exposed to very small quantities of the drug and the compound is delivered directly to the site of action.

Dosages of the compounds of the present invention employed for the treatment of the maladies identified in the present invention will vary depending on the site of treatment, the particular condition to be treated, the severity of the condition, the subject to be treated (who may vary in body weight, age, general health, sex, and other factors), as well as the effect desired.

Dosage levels ranging from about 0.05 mg to about 50 mg per kilogram of body weight per day are useful for the treatment of the conditions or diseases identified in the present invention. This means the amount of the compound disclosed in the present invention that is administered will range from 2.5 mg to about 2.5 gm per patient per day.

The amount of active ingredient that may be combined with the pharmaceutical carrier materials to produce a single dosage form will vary depending upon the host treated and the particular mode of administration. For example, a formulation intended for the oral administration of humans may contain from 2.5 mg to 2.5 gm of active compound of the present invention compounded with an appropriate and convenient amount of carrier material which may vary from about 5 to 95 percent of the total composition. Dosage unit forms will generally contain between from about 5 mg to about 500 mg of active compound of the present invention. Dosage for topical preparation will, in general be less (one tenth to one hundredth) of the dose required for an oral preparation.

EXAMPLES

The following examples are provided to illustrate embodiments of the present invention but are by no means intended to limit its scope.

Example 1

Preparation of Cyclosporin Acetate

A solution of cyclosporin A (5.0 g, 4.16 mmol), acetic anhydride (7.80 mL, 83.2 mmol), and DMAP (760 mg, 6.2 mmol) in methylene chloride (40 mL) was stirred overnight at room temperature under a $N_2$ atmosphere. Saturated sodium bicarbonate solution (200 mL) was added to the solution and stirred for an additional 2 h. The mixture was extracted with ether, washed with 1 N HCl, neutralized with saturated sodium bicarbonate solution, washed with brine, dried over sodium sulfate, and concentrated in vacuo to afford cyclosporin acetate (4.92 g, 95%) as a white solid: $^1$H NMR (300 MHz, $CDCl_3$) δ 8.57 (d, J=9.6 Hz, 1H), 8.04 (d, J=6.9 Hz, 1H), 7.51 (d, J=9.4 Hz, 1H), 7.47 (d, J=7.8 Hz, 1H), 5.67 (dd, J=11.0, 4.0 Hz, 1H), 5.60-5.44 (m, 2H), 5.39 (dd, J=11.7, 3.7 Hz, 1H), 5.32-5.13 (m, 4H), 5.06-4.93 (m, 2H), 4.85 (t, J=7.2 Hz, 1H), 4.77 (t, J=9.6 Hz, 1H), 4.65 (d, J=13.7 Hz, 1H), 4.41 (t, J=7.0 Hz, 1H), 3.46 (s, 3H), 3.26 (s, 3H), 3.24 (s, 3H), 3.21 (s, 3H), 3.10 (s, 3H), 2.68 (s, 3H), 2.66 (s, 3H), 2.50-2.35 (m, 1H), 2.25-1.80 (m, 6H), 2.08 (s, 3H), 2.01 (s, 3H), 1.75-1.55 (m, 6H), 1.45-0.75 (m, 55H); ESI MS m/z 1245 $[C_{64}H_{113}N_{11}O_{13}+H]^+$.

Example 2

Preparation of Acetyl Cyclosporin Aldehyde

Ozone was bubbled into a solution of cyclosporin acetate from Example 1 (3.0 g, 2.4 mmol) in methylene chloride (70 mL) at −78° C. until a blue color was developed. The mixture was degassed with nitrogen for a few minutes and dimethylsulfide (3 mL) was added at −78° C. The reaction mixture was allowed to warm to room temperature and stirred for 3 h. The reaction mixture was concentrated in vacuo and the residue was dissolved in ethyl acetate (300 mL), washed with water (2×70 mL) and brine (70 mL), dried over sodium sulfate, filtered, and concentrated in vacuo to afford acetyl cyclosporin aldehyde (2.79 g, 94%) as a white solid. The crude was carried to the next step without further purification: $^1$H NMR (300 MHz, $CDCl_3$) δ 9.60 (d, J=3.5 Hz, 1H), 8.55 (d, J=9.7 Hz, 1H), 7.96 (d, J=6.8 Hz, 1H), 7.52 (d, J=7.7 Hz, 1H), 7.46 (d, J=9.0 Hz, 1H), 5.67 (dd, J=11.0, 3.8 Hz, 1H), 5.60-5.45 (m, 2H), 5.32 (dd, J=12.1, 3.3 Hz, 1H), 5.24-5.10 (m, 2H), 5.08-4.90 (m, 2H), 4.84 (t, J=7.1 Hz, 1H), 4.73 (t, J=9.6 Hz, 1H), 4.64 (d, J=13.8 Hz, 1H), 4.41 (t, J=7.0 Hz, 1H), 3.46 (s, 3H), 3.29 (s, 6H), 3.21 (s, 3H), 3.08 (s, 3H), 2.67 (s, 3H), 2.65 (s, 3H), 2.50-2.35 (m, 2H), 2.25-1.80 (m, 6H), 1.99 (s, 3H), 1.75-1.55 (m, 3H), 1.50-0.75 (m, 57H); ESI MS m/z 1233 $[C_{62}H_{109}N_{11}O_{14}+H]^+$.

Example 3

Preparation of Acetyl Cyclosporin Vinyl Chloride

Anhydrous $CrCl_2$ (100 mg, 0.81 mmol) was suspended in THF (3 mL) under an argon atmosphere and, then, a solution of acetyl cyclosporin aldehyde from Example 2 (100 mg, 0.081 mmol) and $CHCl_3$ (29 mg, 0.243 mmol) in THF (1 mL) were added. The mixture was stirred at 40° C. under argon for 64 h. After cooling down to room temperature, the solvent was removed in vacuo and the residue was purified via semi-preparative HPLC to give the desired acetyl cyclosporin vinyl chloride (25 mg, 24%) as a white solid: $^1$H NMR ($CDCl_3$, 500 MHz) δ 8.46 (d, J=9.3 Hz, 1H), 8.00 (d, J=6.9 Hz, 1H), 7.64 (d, J=9.0 Hz, 1H), 7.58 (d, J=7.8 Hz, 1H), 5.83 (m, 1H), 5.68 (d, J=7.2 Hz, 1H), 5.56 (d, J=11.1 Hz, 2H), 5.44 (d, J=13.5, 3.8 Hz, 1H), 5.22 (m, 1H), 5.06-4.94 (m, 3H), 4.85 (t, J=7.2 Hz, 1H), 4.77 (d, J=10.6 Hz, 1H), 4.64 (d, J=13.5 Hz, 1H), 4.43 (t, J=6.6 Hz, 1H), 3.77 (q, J=6.9 Hz, 1H), 3.42 (s, 3H), 3.26 (s, 3H), 3.24 (s, 3H), 3.20 (s, 3H), 3.11 (s, 3H), 2.88 (m, 2H), 2.68 (s, 3H), 2.67 (s, 3H), 2.42 (m, 1H), 2.22-2.10 (m, 5H), 2.01 (s, 3H), 1.92-0.62 (m, 60H); ESI MS m/z 1265 $[C_{63}H_{110}ClN_{11}O_{13}+H]^+$.

Example 4

Preparation of Cyclosporin Vinyl Chloride

Acetyl protected cyclosporin vinyl chloride from Example 3 (20 mg, 0.016 mmol) was dissolved in 4 mL of methanol and, then, $K_2CO_3$ (100 mg, 0.725 mmol) was added. The mixture was stirred at room temperature overnight, then diluted with 100 mL of EtOAc, washed with brine (3×10 mL), and dried over $Na_2SO_4$. Solvents were removed in vacuo, and the residue was purified via semi-preparative HPLC to give cyclosporin vinyl chloride (13 mg, 67%) as a white solid: $^1$H NMR ($CDCl_3$, 500 MHz) δ 7.98 (d, J=9.7 Hz, 1H), 7.64 (d, J=7.4 Hz, 1H), 7.42 (d, J=8.4 Hz, 1H), 7.18 (d, J=7.9 Hz, 1H), 5.95 (m, 1H), 5.85 (d, J=13.3 Hz, 1H), 5.46 (d, J=4.5 Hz, 1H), 5.32 (dd, J=11.3, 3.8 Hz, 1H), 5.16-4.94 (m, 5H), 4.85 (t, J=6.9 Hz, 1H), 4.72 (d, J=14.0 Hz, 1H), 4.66 (t, J=8.8 Hz, 1H), 4.54 (t, J=7.2 Hz, 1H), 3.86 (t, J=6.5 Hz, 1H), 3.51 (s, 3H), 3.39 (s, 3H), 3.26 (s, 3H), 3.18 (m, 2H), 3.11 (s, 6H), 2.69 (s, 3H), 2.68 (s, 3H), 2.42 (m, 2H), 2.22-0.62 (m, 65H); ESI MS m/z 1223 $[C_{61}H_{108}ClN_{11}O_{12}+H]^+$; HPLC 94.6% (AUC), $t_R$=15.3 min.

Example 5

Preparation of Acetyl Cyclosporin Vinyl Iodide

To an ice-cooled suspension of chromium(II) chloride (1.0 g, 8.2 mmol) in THF (25 mL) was added a solution of acetyl cyclosporin aldehyde from Example 2 (0.50 g, 0.41 mmol) and iodoform (1.29 g, 3.28 mmol) in THF (25 mL). After 7 h at 0° C., the reaction mixture was poured into ice-water (50 mL). The water layer was extracted with ethyl acetate (3×60 mL). The combined organics were dried over anhydrous sodium sulfate and concentrated. The material was purified by semi-preparative HPLC to afford acetyl cyclosporin vinyl iodide (290 mg, 52%) as a white solid: $^1$H NMR (300 MHz, $CDCl_3$) δ 8.47 (d, J=9.8 Hz, 1H), 8.01 (d, J=6.4 Hz, 1H), 7.56

(d, J=8.8 Hz, 1H), 7.54 (d, J=7.5 Hz, 1H), 6.50-6.40 (m, 1H), 5.84 (d, J=14.3 Hz, 1H), 5.69-5.10 (m, 6H), 4.97 (d, J=11.1 Hz, 2H), 4.87-4.73 (m, 2H), 4.64 (d, J=13.8 Hz, 1H), 4.43 (t, J=7.0 Hz, 1H), 3.43 (s, 3H), 3.28 (s, 3H), 3.26 (s, 3H), 3.20 (s, 3H), 3.12 (s, 3H), 2.68 (s, 3H), 2.66 (s, 3H), 2.45-2.35 (m, 1H), 2.28-1.80 (m, 8H), 2.06 (s, 3H), 1.77-1.60 (m, 3H), 1.50-0.75 (m, 56H); ESI MS m/z 1357 $[C_{63}H_{110}IN_{11}O_{13}+H]^+$.

Example 6

Preparation of Cyclosporin Vinyl Iodide

To a stirred solution of acetyl cyclosporin vinyl iodide from Example 5 (42 mg, 0.030 mmol) in methanol (4 mL) was added potassium carbonate (104 mg, 0.750 mmol) at room temperature. After 12 h at room temperature, methanol was evaporated. Water (20 mL) was added and the mixture was extracted with ethyl acetate (3×70 mL). The organic layer was separated, dried over anhydrous sodium sulfate, and concentrated under vacuum to afford the crude product. The material was purified by semi-preparative HPLC to afford cyclosporin vinyl iodide (30 mg, 78%) as a white solid: $^1$H NMR (300 MHz, CDCl$_3$) δ 7.90 (d, J=9.3 Hz, 1H), 7.66 (d, J=6.5 Hz, 1H), 7.49 (d, J=8.5 Hz, 1H), 7.26 (overlapped with CHCl$_3$, 1H), 6.55-6.43 (m, 1H), 5.93 (d, J=14.0 Hz, 1H), 5.69 (d, J=8.1 Hz, 1H), 5.47 (d, J=5.9 Hz, 1H), 5.32 (d, J=8.0 Hz, 1H), 5.12-4.92 (m, 4H), 4.82 (t, J=6.2 Hz, 1H), 4.74 (d, J=14.8 Hz, 1H), 4.67 (t, J=9.1 Hz, 1H), 4.53 (t, J=7.2 Hz, 1H), 3.82 (t, J=6.2 Hz, 1H), 3.50 (s, 3H), 3.37 (s, 3H), 3.25 (s, 3H), 3.11 (s, 6H), 2.72 (s, 3H), 2.69 (s, 3H), 2.48-1.90 (m, 8H), 1.80-1.53 (m, 6H), 1.50-0.72 (m, 55H); ESI MS m/z 1315 $[C_{61}H_{108}IN_{11}O_{12}+H]^+$; HPLC 94.3% (AUC), $t_R$=15.82 min.

Example 7

Preparation of the Acetates of cis- and trans-Deuterated Cyclosporin Vinyl Iodide A mixture of acetyl cyclosporin aldehyde from Example 2 (500 mg, 0.40 mmol) and iodoform-d (1.35 g, 4.0 mmol) in anhydrous THF (10 mL) was cooled to −78° C. After cooling, chromium chloride (1.0 g, 8.0 mmol) was quickly added to the reaction. The mixture was allowed to warm to 0° C. and stirred under N$_2$ atmosphere for 5 h. The mixture was poured into ice-water (300 mL) and extracted with ethyl acetate (3×200 mL). Combined organic layers were washed with brine, dried over sodium sulfate, and concentrated in vacuo. The crude product was purified by semi-preparative HPLC to afford the acetate of trans-deuterated cyclosporin vinyl iodide (220 mg, 40%) as a light brown solid: $^1$H NMR (300 MHz, CDCl$_3$) δ 8.47 (d, J=9.6 Hz, 1H), 8.01 (d, J=6.8 Hz, 1H), 7.57 (t, J=8.6 Hz, 2H), 6.44 (dd, J=8.6, 6.1 Hz, 2H), 6.01-5.56 (m, 4H), 5.52 (d, J=10.3 Hz, 2H), 5.28 (d, J=3.4 Hz, 1H), 5.24 (d, J=3.4 Hz, 1H), 4.97 (d, J=10.9 Hz, 3H), 4.85-4.76 (m, 5H), 4.64 (d, J=13.9 Hz, 2H), 4.43 (t, J=7.0 Hz, 2H), 3.43 (s, 3H), 3.25 (s, 3H), 3.24 (s, 3H), 3.20 (s, 3H), 3.11 (s, 3H), 2.67 (s, 3H), 2.66 (s, 3H), 2.01 (s, 2H), 1.32 (d, J=7.1 Hz, 4H), 1.28 (d, J=6.9 Hz, 4H), 1.06-0.74 (m, 52H); ESI MS m/z 1357 $[C_{63}H_{109}DIN_{11}O_{13}+H]^+$; and the acetate of cis-deuterated cyclosporin vinyl iodide (40 mg, 7%) as a light brown solid: $^1$H NMR (300 MHz, CDCl$_3$) δ 8.57 (d, J=9.6 Hz, 1H), 8.02 (d, J=6.8 Hz, 1H), 7.66 (d, J=9.0 Hz, 1H), 7.53 (d, J=7.7 Hz, 1H), 6.02-5.92 (m, 2H), 5.69 (dd, J=11.0, 3.9 Hz, 1H), 5.54 (d, J=3.9 Hz, 3H), 5.33-5.13 (m, 5H), 4.98 (d, J=11.1 Hz, 3H), 4.82 (t, J=7.3 Hz, 2H), 4.74 (t, J=9.5 Hz, 2H), 4.64 (d, J=13.8 Hz, 2H), 4.32 (t, J=7.0 Hz, 2H), 3.44 (s, 3H), 3.28 (s, 3H), 3.25 (s, 3H), 3.20 (s, 3H), 3.11 (s, 3H), 2.67 (s, 3H), 2.66 (s, 3H), 2.05 (s, 2H), 1.29 (d, J=5.5 Hz, 4H), 1.24 (d, J=11.9 Hz, 4H), 1.05 (d, J=6.4 Hz, 2H), 1.02-0.64 (m, 50H); ESI MS m/z 1357 $[C_{63}H_{109}DIN_{11}O_{13}+H]^+$.

Example 8

Preparation of cis-Deuterated Cyclosporin Vinyl Iodide

A solution of the acetate of cis-deuterated cyclosporin vinyl iodide from Example 7 (40 mg, 0.029 mmol) in methanol (2 mL) was stirred at room temperature. Reaction mixture was treated with potassium carbonate (50 mg, 0.36 mmol) and was allowed to keep stirring under N$_2$ atmosphere overnight. Mixture was diluted with ethyl acetate, washed with saturated sodium bicarbonate solution and brine, dried over sodium sulfate, and concentrated in vacuo. The crude product was purified by semi-preparative HPLC to afford cis-deuterated cyclosporin vinyl iodide (20 mg, 53%) as a white solid: $^1$H NMR (300 MHz, CDCl$_3$) δ 8.03 (d, J=9.7 Hz, 1H), 7.65 (d, J=7.2 Hz, 1H), 7.47 (d, J=8.3 Hz, 1H), 7.26 (hidden by solvent peak, 1H), 6.17 (dd, J=7.8, 5.6 Hz, 1H), 5.69 (dd, J=10.8, 3.8 Hz, 1H), 5.43 (d, J=7.3 Hz, 2H), 5.31 (dd, J=11.4, 3.8 Hz, 1H), 5.11-4.99 (m, 7H), 4.84 (t, J=7.2 Hz, 2H), 4.83-4.62 (m, 6H), 4.49 (t, J=7.2 Hz, 2H), 3.96 (t, J=6.6 Hz, 2H), 3.51 (s, 3H), 3.40 (s, 3H), 3.24 (s, 3H), 3.12 (s, 3H), 3.11 (s, 3H), 2.69 (s, 3H), 2.68 (s, 3H), 1.35 (d, J=7.2 Hz, 4H), 1.25 (t, J=2.6 Hz, 4H), 1.07-0.81 (m, 50H); ESI MS m/z 1316 $[C_{61}H_{107}DIN_{11}O_{12}+H]^+$; HPLC>99% (AUC), $t_R$=20.40 min.

Example 9

Preparation of trans-Deuterated Cyclosporin Vinyl Iodide

A solution of the acetate of trans-deuterated cyclosporin vinyl iodide from Example 7 (50 mg, 0.037 mmol) in methanol (2 mL) was stirred at room temperature. Reaction mixture was treated with potassium carbonate (60 mg, 0.43 mmol) and was allowed to keep stirring under N$_2$ atmosphere overnight. Mixture was diluted with ethyl acetate, washed with saturated sodium bicarbonate solution and brine, dried over sodium sulfate, and concentrated in vacuo. The crude product was purified by semi-preparative HPLC to afford trans-deuterated cyclosporin vinyl iodide (29 mg, 60%) as a white solid: $^1$H NMR (300 MHz, CDCl$_3$) δ 7.95 (d, J=9.8 Hz, 1H), 7.63 (d, J=7.4 Hz, 1H), 7.43 (d, J=8.3 Hz, 1H), 7.17 (d, J=6.2 Hz, 1H), 6.50 (t, J=8.0 Hz, 1H), 5.70 (dd, J=10.9, 3.8 Hz, 1H), 5.49 (d, J=6.2 Hz, 2H), 5.31 (dd, J=10.8, 3.8 Hz, 1H), 5.10-4.62 (m, 15H), 4.50 (t, J=7.2 Hz, 2H), 3.82 (t, J=6.3 Hz, 2H), 3.51 (s, 3H), 3.39 (s, 3H), 3.26 (s, 3H), 3.11 (s, 3H), 3.10 (s, 3H), 2.69 (s, 3H), 2.68 (s, 3H), 1.34 (d, J=7.1 Hz, 4H), 1.25 (d, J=4.7 Hz, 4H), 1.08-0.81 (m, 48H), 0.74 (d, J=8.0 Hz, 2H); ESI MS m/z 1316 $[C_{61}H_{107}DIN_{11}O_{12}+H]^+$; HPLC>99% (AUC), $t_R$=20.17 min.

Example 10

Preparation of the Acetates of cis- and trans-Deuterated Cyclosporin Vinyl Chloride A mixture of acetyl cyclosporin aldehyde from Example 2 (500 mg, 0.40 mmol) and chloroform-d (0.32 mL, 4.0 mmol) in anhydrous THF (5 mL) was cooled to −78° C. After cooling, chromium chloride (1.0 g, 8.0 mmol) was quickly added to the reaction. Mixture was allowed to warm to 0° C. and stirred under $N_2$ atmosphere for 4 h. Mixture was poured into ice-water (300 mL) and extracted with ethyl acetate (3×200 mL). Combined organic layers were washed with brine, dried over sodium sulfate, and concentrated in vacuo. The crude product was purified by semi-preparative HPLC to afford the acetate of trans-deuterated cyclosporin vinyl chloride (136 mg, 27%) as a light brown solid: $^1$H NMR (300 MHz, CDCl$_3$) δ 8.48 (d, J=9.6 Hz, 1H), 8.00 (d, J=6.8 Hz, 1H), 7.65 (d, J=9.1 Hz, 1H), 7.59 (d, J=7.8 Hz, 1H), 5.84 (dd, J=9.3, 5.6 Hz, 2H), 5.68 (dd, J=11.1, 3.8 Hz, 2H), 5.57 (d, J=4.8 Hz, 1H), 5.53 (d, J=8.5 Hz, 1H), 5.48-4.97 (m, 11H), 4.87-4.76 (m, 3H), 4.64 (d, J=12.2 Hz, 2H), 4.43 (t, J=7.0 Hz, 2H), 3.43 (s, 3H), 3.26 (s, 3H), 3.24 (s, 3H), 3.20 (s, 3H), 3.11 (s, 3H), 2.67 (s, 3H), 2.66 (s, 3H), 2.01 (s, 2H), 1.42-1.27 (m, 8H), 1.06-0.74 (m, 50H); ESI MS m/z 1267 $[C_{63}H_{109}DClN_{11}O_{13}+H]^+$; and the acetate of cis-deuterated cyclosporin vinyl chloride (32 mg, 6%) as a light brown solid: $^1$H NMR (300 MHz, CDCl$_3$) δ 8.54 (d, J=9.6 Hz, 1H), 8.03 (d, J=6.8 Hz, 1H), 7.74 (d, J=9.0 Hz, 1H), 7.58 (d, J=7.7 Hz, 1H), 5.71-5.58 (m, 3H), 5.53 (d, J=7.0 Hz, 2H), 5.40-5.10 (m, 6H), 4.98 (d, J=11.0 Hz, 3H), 4.85 (t, J=7.3 Hz, 2H), 4.75 (t, J=9.5 Hz, 2H), 4.64 (d, J=13.8 Hz, 2H), 4.44 (t, J=7.0 Hz, 2H), 3.44 (s, 3H), 3.27 (s, 3H), 3.22 (s, 3H), 3.19 (s, 3H), 3.11 (s, 3H), 2.68 (s, 3H), 2.67 (s, 3H), 2.04 (s, 2H), 1.34-1.27 (m, 8H), 1.05 (d, J=6.4 Hz, 2H), 1.02-0.79 (m, 50H); ESI MS m/z 1267 $[C_{63}H_{109}DClN_{11}O_{13}+H]^+$.

Example 11

Preparation of trans-Deuterated Cyclosporin Vinyl Chloride

A solution of the acetate of trans-deuterated cyclosporin vinyl chloride from Example 10 (30 mg, 0.024 mmol) in methanol (2 mL) was stirred at room temperature. Reaction mixture was treated with potassium carbonate (35 mg, 0.25 mmol) and was allowed to keep stirring under $N_2$ atmosphere overnight. Mixture was diluted with ethyl acetate, washed with saturated sodium bicarbonate solution and brine, dried over sodium sulfate, and concentrated in vacuo. The crude product was purified by semi-preparative HPLC to afford trans-deuterated cyclosporin vinyl chloride (17 mg, 60%) as a white solid: $^1$H NMR (300 MHz, CDCl$_3$) δ 7.96 (d, J=9.6 Hz, 1H), 7.65 (d, J=7.3 Hz, 1H), 7.45 (d, J=8.2 Hz, 1H), 7.21 (d, J=7.8 Hz, 1H), 5.92 (t, J=8.4 Hz, 2H), 5.69 (dd, J=11.0, 4.1 Hz, 1H), 5.48 (d, J=6.4 Hz, 2H), 5.33 (dd, J=11.4, 3.9 Hz, 1H), 5.17-4.62 (m, 16H), 4.51 (t, J=7.2 Hz, 2H), 4.85 (t, J=6.4 Hz, 2H), 3.51 (s, 3H), 3.39 (s, 3H), 3.26 (s, 3H), 3.11 (s, 6H), 2.70 (s, 3H), 2.68 (s, 3H), 1.34 (d, J=7.2 Hz, 2H), 1.26 (d, J=6.6 Hz, 2H), 1.08-0.75 (m, 50H), 0.66 (d, J=5.2 Hz, 2H); ESI MS m/z 1224 $[C_{61}H_{107}DClN_{11}O_{12}+H]^+$; HPLC>99% (AUC), $t_R$=19.57 min.

Example 12

Preparation of cis-Deuterated Cyclosporin Vinyl Chloride

A solution of the acetate of cis-deuterated cyclosporin vinyl chloride from example 10 (32 mg, 0.025 mmol) in methanol (2 mL) was stirred at room temperature. Reaction mixture was treated with potassium carbonate (38 mg, 0.27 mmol) and was allowed to keep stirring under $N_2$ atmosphere overnight. Mixture was diluted with ethyl acetate, washed with saturated sodium bicarbonate solution and brine, dried over sodium sulfate, and concentrated in vacuo. The crude product was purified by semi-preparative HPLC to afford cis-deuterated cyclosporin vinyl chloride (17 mg, 55%) as a white solid: $^1$H NMR (300 MHz, CDCl$_3$) δ 8.05 (d, J=9.7 Hz, 1H), 7.68 (d, J=7.1 Hz, 1H), 7.50 (d, J=8.3 Hz, 1H), 7.28 (d, J=9.0 Hz, 1H), 5.83-5.77 (m, 2H), 5.69 (dd, J=10.9, 4.0 Hz, 1H), 5.42 (d, J=7.3 Hz, 2H), 5.29 (dd, J=11.3, 3.8 Hz, 1H), 5.11-4.98 (m, 7H), 4.82 (t, J=7.3 Hz, 2H), 4.78-4.62 (m, 7H), 4.49 (t, J=7.1 Hz, 2H), 3.94 (t, J=6.7 Hz, 2H), 3.51 (s, 3H), 3.40 (s, 3H), 3.24 (s, 3H), 3.12 (s, 3H), 3.11 (s, 3H), 2.69 (s, 3H), 2.68 (s, 3H), 1.34 (d, J=7.2 Hz, 2H), 1.26 (d, J=6.6 Hz, 2H), 1.07-0.76 (m, 52H); ESI MS m/z 1224 $[C_{61}H_{107}DClN_{11}O_{12}+H]^+$; HPLC>99% (AUC), $t_R$=19.82 min.

Example 13

Preparation of the Acetates of cis- and trans-Cyclosporin Vinyl Chloride

NaHMDS (1.0 M in THF, 0.4 mL, 0.4 mmol) was added to a mixture of (chloromethyl)triphenylphosphonium chloride (140 mg, 0.4 mmol) and 4 mL of THF at −78° C. under nitrogen, the mixture was stirred at −78° C. for 1 h, followed by the addition of a solution of acetyl cyclosporin aldehyde from Example 2 (100 mg, 0.08 mmol) in 3 mL of THF. The resulted mixture was stirred at −78° C. for 2 h, quenched with 4 mL of saturated aqueous NH$_4$Cl, extracted with ether (3×30 mL). Combined organic layers were washed with brine, dried over Na$_2$SO$_4$. After that, the solvent was removed in vacuo, and the residue was purified via semi-preparative HPLC to give the acetate of the cis-isomer of cyclosporin vinyl chloride (13 mg, 12%) as a white solid: $^1$H NMR (CDCl$_3$, 300 MHz) δ 8.56 (d, J=9.6 Hz, 1H), 8.03 (d, J=6.9 Hz, 1H), 7.67 (d, J=9.3 Hz, 1H), 7.54 (d, J=7.8 Hz, 1H), 5.92 (d, J=6.9 Hz, 1H), 5.67 (m, 2H), 5.53 (d, J=6.0 Hz, 2H), 5.28-5.11 (m, 10H), 4.97 (d, J=11.1 Hz, 3H), 4.85 (t, J=7.2 Hz, 1H), 4.74 (t, J=6.6 Hz, 1H), 4.63 (d, J=13.8 Hz, 1H), 4.43 (t, J=6.9 Hz, 1H), 3.44 (s, 3H), 3.27 (s, 3H), 3.24 (m, 2H), 3.23 (s, 3H), 3.20 (s, 3H), 3.09 (s, 3H), 2.67 (s, 3H), 2.65 (s, 3H), 2.42 (m, 1H), 2.23-2.10 (m, 6H), 2.00 (s, 3H), 1.98-0.62 (m, 51H); ESI MS m/z 1265 $[C_{63}H_{110}ClN_{11}O_{13}+H]^+$; and the acetate of the trans-isomer of cyclosporin vinyl chloride (10 mg, 9.7%) as a white solid: $^1$H NMR (CDCl$_3$, 500 MHz) δ 8.46 (d, J=9.3 Hz, 1H), 8.00 (d, J=6.9 Hz, 1H), 7.64 (d, J=9.0 Hz, 1H), 7.58 (d, J=7.8 Hz, 1H), 5.83 (m, 1H), 5.68 (d, J=7.2 Hz, 1H), 5.56 (d, J=11.1 Hz, 2H), 5.44 (d, J=13.5, 3.8 Hz, 1H), 5.22 (m, 1H), 5.06-4.94 (m, 3H), 4.85 (t, J=7.2 Hz, 1H), 4.77 (d, J=10.6 Hz, 1H), 4.64 (d, J=13.5 Hz, 1H), 4.43 (t, J=6.6 Hz, 1H), 3.77 (q, J=6.9 Hz, 1H), 3.42 (s, 3H), 3.26 (s, 3H), 3.24 (s, 3H), 3.20 (s, 3H), 3.11 (s, 3H), 2.88 (m, 2H), 2.68 (s, 3H), 2.67 (s, 3H), 2.42 (m, 1H), 2.22-2.10 (m, 5H), 2.01 (s, 3H), 1.92-0.62 (m, 60H); ESI MS m/z 1265 $[C_{63}H_{110}ClN_{11}O_{13}+H]^+$.

Example 14

Preparation of the cis-Isomer of Cyclosporin Vinyl Chloride

The acetate of the cis-isomer of cyclosporin vinyl chloride from Example 13 (13 mg, 0.01 mmol) was dissolved in 3 mL of methanol, and then K$_2$CO$_3$ (50 mg, 0.36 mmol) was added. The mixture was stirred at room temperature overnight, then diluted with 100 mL of EtOAc, washed with brine (3×10 mL), dried over Na$_2$SO$_4$. Solvents were removed in vacuo, and the residue was purified via semi-preparative HPLC to give the cis-isomer of cyclosporin chloride (9 mg, 71%) as a white solid: $^1$H NMR (CDCl$_3$, 500 MHz) δ 8.04 (d, J=9.7 Hz, 1H), 7.68 (d, J=7.3 Hz, 1H), 7.49 (d, J=8.5 Hz, 1H), 7.27 (d, J=9.8

Hz, 1H), 6.98 (s, 1H), 5.99 (d, J=7.1 Hz, 1H), 5.80 (q, J=7.6 Hz, 1H), 5.68 (dd, J=1.0, 4.2 Hz, 1H), 5.42 (d, J=7.4 Hz, 1H), 5.28(dd, J=11.4, 3.8 Hz, 1H), 5.10 (m, 2H), 5.06-4.94 (m, 3H), 4.82 (t, J=7.2 Hz, 1H), 4.70 (d, J=14.0 Hz, 1H), 4.66 (t, J=9.2 Hz, 1H), 4.50 (t, J=7.2 Hz, 1H), 3.95 (t, J=6.5 Hz, 1H), 3.51 (s, 3H), 3.40 (s, 3H), 3.25 (s, 3H), 3.20 (m, 2H), 3.12 (s, 3H), 3.11 (s, 3H), 2.70 (s, 3H), 2.69 (s, 3H), 2.42 (m, 2H), 2.22-0.62 (m, 63H); ESI MS m/z 1223 $[C_{61}H_{108}ClN_{11}O_{12}+H]^+$; HPLC 94.6% (AUC), $t_R$=15.8 min.

Example 15

Preparation of the Acetate of cis-Cyclosporin Vinyl Iodide

To a vigorously stirred suspension of (iodomethyl)triphenylphosphonium iodide (1.3 g, 2.4 mmol) in dry THF (18 mL) under nitrogen, was added sodium bis(trimethylsilyl) amide (2.4 mL, 1 M in THF, 2.4 mmol). After 10 min at room temperature, the mixture was cooled to 0° C. and acetyl cyclosporin aldehyde from Example 2 (300 mg, 0.240 mmol) in anhydrous THF (10 mL) was added dropwise. After 10 min at 0° C., the reaction was quenched with a saturated solution of ammonium chloride (10 mL), and then allowed to warm to room temperature. The resulting solid was filtered off through a plug of diatomaceous earth and washed with ethyl acetate (200 mL). The organic layer was washed with an aqueous solution of sodium hydrogensulfite (20%, 200 mL), then dried over anhydrous sodium sulfate and concentrated under vacuum to afford the crude product (540 mg). The material was purified by semi-preparative HPLC to afford the acetate of the cis-isomer of cyclosporin vinyl iodide (150 mg, 46%) as a pale-brown oil: $^1$H NMR (300 MHz, CDCl$_3$) δ 8.53 (d, J=9.8 Hz, 1H), 8.15 (d, J=6.5 Hz, 1H), 7.82 (d, J=9.0 Hz, 1H), 7.63 (d, J=8.2 Hz, 1H), 6.10 (d, J=7.4 Hz, 1H), 6.02-5.94 (m, 1H), 5.69 (dd, J=10.9, 3.8 Hz, 1H), 5.61-5.48 (m, 2H), 5.38-5.13 (m, 3H), 4.98 (d, J=10.9 Hz, 2H), 4.87 (t, J=7.4 Hz, 1H), 4.78 (t, J=9.6 Hz, 1H), 4.63 (d, J=14.2 Hz, 1H), 4.47 (t, J=7.0 Hz, 1H), 3.98 (s, 3H), 3.43 (s, 3H), 3.27 (s, 3H), 3.21 (s, 3H), 3.19 (s, 3H), 3.14 (s, 3H), 2.69 (s, 3H), 2.42-2.30 (m, 1H), 2.22-1.85 (m, 8H), 2.06 (s, 3H), 1.77-1.60 (m, 3H), 1.54-0.75 (m, 56H); ESI MS m/z 1357 $[C_{63}H_{110}IN_{11}O_{13}+H]^+$.

Example 16

Preparation of cis-Cyclosporin Vinyl Iodide

To a stirred solution of the acetate of the cis-isomer of cyclosporin vinyl iodide from Example 15 (70 mg, 0.052 mmol) in methanol (8 mL) was added potassium carbonate (180 mg, 1.30 mmol) at room temperature. After 12 h at room temperature, methanol was evaporated. Water (20 mL) was added and the mixture was extracted with ethyl acetate (3×70 mL). The organic layer was separated, dried over anhydrous sodium sulfate, and concentrated under vacuum to afford the crude product (47 mg). The material was purified by semi-preparative HPLC to afford cis-cyclosporin vinyl iodide (19 mg, 28%) as a white solid: $^1$H NMR (300 MHz, CDCl$_3$) δ 8.01 (d, J=9.8 Hz, 1H), 7.65 (d, J=7.2 Hz, 1H), 7.48 (d, J=8.4 Hz, 1H), 7.27 (d, J=7.8 Hz, 1H), 6.17 (s, 2H), 5.69 (dd, J=11.0, 4.0 Hz, 1H), 5.43 (d, J=7.3 Hz, 1H), 5.31 (dd, J=11.3, 3.7 Hz, 1H), 5.12-4.95 (m, 4H), 4.84 (t, J=7.5 Hz, 1H), 4.71 (d, J=13.7 Hz, 1H), 4.67 (t, J=9.5 Hz, 1H), 4.47 (t, J=7.0 Hz, 1H), 3.96 (t, J=6.7 Hz, 1H), 3.52 (s, 3H), 3.40 (s, 3H), 3.25 (s, 3H), 3.12 (s, 6H), 2.69 (s, 6H), 2.48-1.95 (m, 8H), 1.89-1.53 (m, 6H), 1.50-0.72 (m, 55H); ESI MS m/z 1315 $[C_{61}H_{108}IN_{11}O_{12}+H]^+$; HPLC 89.7% (AUC), $t_R$=24.46 min.

Example 17

Preparation of the Acetates of cis- and trans-Cyclosporin Vinyl Bromide

NaHMDS (1.0 M in THF, 0.8 mL, 0.8 mmol) was added to a mixture of (bromomethyl)triphenyl phosphonium bromide (348 mg, 0.8 mmol) and 8 mL of THF at −78° C. under nitrogen, the mixture was stirred at −78° C. for 1 h, followed by the addition of a solution of acetyl cyclosporin aldehyde from Example 2 (200 mg, 0.16 mmol) in 4 mL of THF. The resulted mixture was stirred −78° C. for 2 h, quenched with 8 mL of saturated aqueous NH$_4$Cl, extracted with ether (3×30 mL). Combined organic layers were washed with brine, dried over Na$_2$SO$_4$. After that, the solvent was removed in vacuo, and the residue was purified via semi-preparative HPLC to give the acetate of the trans-isomer of cyclosporin vinyl bromide (4 mg, 1.9%) as a white solid: $^1$H NMR (CDCl$_3$, 500 MHz) δ 8.50 (d, J=9.8 Hz, 1H), 7.98 (d, J=6.9 Hz, 1H), 7.48 (d, J=8.1 Hz, 1H), 7.41 (d, J=9.2 Hz, 1H), 6.18 (m, 1H), 5.86 (d, J=13.6 Hz, 1H), 5.68 (dd, J=11.2, 4.6 Hz, 1H), 5.52 (q, J=12.1 Hz, 2H), 5.40 (dd, J=11.6, 4.1 Hz, 1H), 5.28 (dd, J=14.3, 3.6 Hz, 1H), 5.14 (dd, J=13.8, 6.0 Hz, 1H), 4.96 (dd, J=16.5, 5.5 Hz, 2H), 4.84 (t, J=7.4 Hz, 1H), 4.77 (t,J=9.6 Hz, 1H), 4.64 (d, J=13.8 Hz, 1H), 4.41 (t, J=7.0 Hz, 1H), 3.43 (s, 3H), 3.27 (s, 3H), 3.26 (s, 3H), 3.23 (s, 3H), 3.15 (m, 2H), 3.10 (s, 3H), 2.67 (s, 3H), 2.65 (s, 3H), 2.42 (m, 1H), 2.22-0.62 (m, 68H); ESI MS m/z 1309 $[C_{63}H_{110}N_{11}O_{13}+H]^+$; and the acetate of the cis-isomer of cyclosporin vinyl bromide (13 mg, 6.1%) as a white solid: $^1$H NMR (CDCl$_3$, 300 MHz) δ 8.57 (d, J=9.6 Hz, 1H), 8.04 (d, J=6.6 Hz, 1H), 7.76 (d, J=9.1 Hz, 1H), 7.59 (d, J=7.8 Hz, 1H), 6.04 (m, 2H), 5.70 (dd, J=10.8, 3.6 Hz, 1H), 5.53 (t, J=11.7 Hz, 1H), 5.32-5.14 (m, 4H), 5.01 (d, J=8.1 Hz, 2H), 4.86 (t, J=7.2 Hz, 1H), 4.76 (t, J=9.6 Hz, 1H), 4.63 (d, J=14.1 Hz, 1H), 4.44 (t, J=6.6 Hz, 1H), 3.45 (s, 3H), 3.30 (s, 3H), 3.27 (s, 3H), 3.26 (s, 3H), 3.24 (m, 2H), 3.12 (s, 3H), 2.68 (s, 3H), 2.67 (s, 3H), 2.42 (m, 1H), 2.22-0.62 (m, 68H); ESI MS m/z 1309 $[C_{63}H_{110}N_{11}O_{13}+H]^+$.

Example 18

Preparation of cis-Cyclosporin Vinyl Bromide

The acetate of the cis-isomer of cyclosporin vinyl bromide from Example 17 (13 mg, 0.01 mmol) was dissolved in 3 mL of methanol, and then K$_2$CO$_3$ (50 mg, 0.36 mmol) was added. The mixture was stirred at room temperature overnight, then diluted with 100 mL of EtOAc, washed with brine (3×10 mL), dried over Na$_2$SO$_4$. Solvents were removed in vacuo, the residue was purified via semi-preparative HPLC to give the cis-cyclosporin vinyl bromide (5.1 mg, 40%) as a white solid: $^1$H NMR (CDCl$_3$, 500 MHz) δ 8.05 (d, J=9.8 Hz, 1H), 7.67 (d, J=7.2 Hz, 1H), 7.46 (d, J=8.3 Hz, 1H), 7.23 (d, J=9.2 Hz, 2H), 6.98 (s, 1H), 6.10 (m, 2H), 5.68 (dd, J=10.9, 4.3 Hz, 1H), 5.42 (d, J=7.5 Hz, 1H), 5.28 (dd, J=11.5, 4.0 Hz, 1H), 5.10-5.00 (m, 4H), 4.82 (t, J=6.8 Hz, 1H), 4.69 (d, J=13.9 Hz, 1H), 4.65 (t, J=9.4 Hz, 1H), 4.49 (t, J=7.2 Hz, 1H), 3.96 (t, J=6.1 Hz, 1H), 3.51 (s, 3H), 3.41 (s, 3H), 3.25 (s, 3H), 3.18 (m, 2H), 3.12 (s, 3H), 3.10 (s, 3H), 2.70 (s, 3H), 2.68 (s, 3H), 2.42 (m, 1H), 2.22-0.62 (m, 64H); ESI MS m/z 1267 $[C_{61}H_{108}N_{11}O_{12}+H]^+$; HPLC 98.3% (AUC), $t_R$=16.1 min.

Example 19

Preparation of trans-Cyclosporin Vinyl Bromide

The acetate of the trans-isomer of cyclosporin vinyl bromide from Example 17 (7 mg, 0.005 mmol) was dissolved in 3 mL of methanol, and then K$_2$CO$_3$ (50 mg, 0.36 mmol) was added. The mixture was stirred at room temperature overnight, then diluted with 100 mL of EtOAc, washed with brine (3×10 mL), dried over Na$_2$SO$_4$. Solvents were removed in vacuo, and the residue was purified by semi-preparative HPLC to give trans-cyclosporin vinyl bromide (4.0 mg, 55%) as a white solid: $^1$H NMR (CDCl$_3$, 500 MHz) δ 7.96 (d, J=8.5 Hz, 1H), 7.63 (d, J=7.0 Hz, 1H), 7.41 (d, J=8.6 Hz, 1H), 7.17 (d, J=8.2 Hz, 1H), 6.20 (ddd, J=22.4, 13.8, 8.9 Hz, 1H), 5.94 (d, J=13.3 Hz, 1H), 5.70 (dd, J=11.2, 4.2 Hz, 1H), 5.49 (d, J=6.5 Hz, 1H), 5.32 (dd, J=7.9, 4.0 Hz, 1H), 5.13-5.02 (m, 4H), 4.96 (dd, J=10.2, 5.6 Hz, 1H), 4.83 (t, J=7.2 Hz, 1H), 4.72 (d, J=13.6 Hz, 1H), 4.65 (dd, J=17.7, 9.0 Hz, 1H), 4.61 (t, J=7.2 Hz, 1H), 3.85 (t, J=6.1 Hz, 1H), 3.51 (s, 3H), 3.39 (s, 3H), 3.26 (s, 3H), 3.18 (d, J=14.2 Hz, 2H), 3.11 (s, 6H), 2.70 (s, 3H), 2.68 (s, 3H), 2.45-2.40 (m, 2H), 2.12-2.02 (m, 7H), 1.85-0.76 (m, 57H); ESI MS m/z 1267 [C$_{61}$H$_{108}$BrN$_{11}$O$_{12}$+H]$^+$; HPLC 98.9% (AUC), t$_R$=16.4 min.

Example 20

Preparation of the Acetate of Cyclosporin Vinyl Dichloride

To a mixture of acetyl cyclosporin aldehyde from Example 2 (150 mg, 0.120 mmol) and triphenylphosphine (630 mg, 2.40 mmol) in acetonitrile (2 mL) was added carbon tetrachloride (0.12 mL, 1.2 mmol) in one portion at 0° C. The mixture was allowed to warm to room temperature. After 2 h at room temperature, water (5 mL) was added into the solution and then the mixture was extracted with ethyl acetate (100 mL). The organic layer was washed with brine (20 mL), dried over anhydrous sodium sulfate, and concentrated. The crude product was purified by semi-preparative HPLC to afford the acetate of cyclosporin vinyl dichloride (50 mg, 32%) as a white solid: $^1$H NMR (300 MHz, CDCl$_3$) δ 8.49 (d, J=9.7 Hz, 1H), 8.01 (d, J=6.8 Hz, 1H), 7.60 (app t, J=7.2 Hz, 2H), 5.99 (dd, J=8.9, 5.6 Hz, 1 H), 5.68 (dd, J=11.0, 3.9 Hz, 1H), 5.60-5.45 (m, 2H), 5.41 (dd, J=12.0, 3.8 Hz, 1H), 5.30-4.75 (m, 6H), 4.63 (d, J=14.0 Hz, 1H), 4.43 (t, J=7.0 Hz, 1H), 3.43 (s, 3H), 3.28 (s, 3H), 3.26 (s, 3H), 3.20 (s, 3H), 3.11 (s, 3H), 2.68 (s, 3H), 2.67 (s, 3H), 2.45-2.35 (m, 1H), 2.28-1.85 (m, 8H), 2.03 (s, 3H), 1.75-1.60 (m, 3H), 1.45-0.75 (m, 56H); ESI MS m/z 1299 [C$_{63}$H$_{109}$Cl$_2$N$_{11}$O$_{13}$+H]$^+$.

Example 21

Preparation of Cyclosporin Vinyl Dichloride

To a stirred solution of the acetate of cyclosporin vinyl dichloride from Example 20 (45 mg, 0.040 mmol) in methanol (4 mL) was added potassium carbonate (121 mg, 0.870 mmol) at room temperature. After 12 h at room temperature, methanol was evaporated. Water (20 mL) was added and the mixture was extracted with ethyl acetate (3×70 mL). The organic layer was separated, dried over anhydrous sodium sulfate, and concentrated under vacuum to afford the crude product. The material was purified by semi-preparative HPLC to afford cyclosporin vinyl dichloride (25 mg, 57%) as an off-white solid: $^1$H NMR (300 MHz, CDCl$_3$) δ 7.98 (d, J=9.9 Hz, 1H), 7.69 (d, J=7.2 Hz, 1H), 7.42 (d, J=8.5 Hz, 1H), 7.28 (overlapped with CHCl$_3$, 1H), 6.02 (t, J=8.1 Hz, 1H), 5.69 (dd, J=7.0, 3.9 Hz, 1H), 5.43 (d, J=8.3 Hz, 1H), 5.34 (dd, J=11.7, 3.8 Hz, 1H), 5.15-4.95 (m, 4H), 4.83 (t, J=7.0 Hz, 1H), 4.74-4.63 (m, 2H), 4.49 (t, J=7.2 Hz, 1H), 3.92 (t, J=6.5 Hz, 1H), 3.50 (s, 3H), 3.39 (s, 3H), 3.26 (s, 3H), 3.13 (s, 3H), 3.11 (s, 3H), 2.70 (s, 3H), 2.68 (s, 3H), 2.48-2.34 (m, 2H), 2.20-1.92 (m, 6H), 1.80-1.53 (m, 6H), 1.50-0.75 (m, 55H); ESI MS m/z 1257 [C$_{61}$H$_{107}$Cl$_2$N$_{11}$O$_{12}$+H]$^+$; HPLC 97.3% (AUC), t$_R$=16.42 min.

Example 22

Preparation of the Acetates of cis- and trans-Cyclosporin Phenylvinyl Chloride

To a solution of diethyl benzylphosphonate (0.50 mL, 2.4 mmol) in THF (2 mL) at −78° C. was added n-butyllithium (1.1 mL, 2.5 M in hexane, 2.6 mmol) dropwise. After 15 min at −78° C., a solution of carbon tetrachloride (0.23 mL, 2.4 mmol) in THF (1 mL) was added. After 15 min at −78° C., a solution of acetyl cyclosporin aldehyde from Example 2 (150 mg, 0.120 mmol) in THF (1 mL) was added. After 15 min at −78° C., the reaction was allowed to warm to room temperature over 1 h. The reaction was quenched with water (2 mL), and then extracted with ethyl acetate (2×50 mL). The combined organics were dried over anhydrous sodium sulfate and concentrated. The crude product was purified by semi-preparative HPLC to afford the acetate of cyclosporin phenylvinyl chloride (118 mg, 73%) as a mixture of cis and trans-isomers and a pale-brown solid: $^1$H NMR (300 MHz, CDCl$_3$) δ 8.49 (d, J=9.0 Hz, 1H), 8.07 (d, J=6.5 Hz, 0.5H), 8.00 (d, J=6.5 Hz, 0.5H), 7.76 (d, J=8.9 Hz, 1H), 7.66 (d, J=8.1 Hz, 0.5H), 7.61 (d, J=8.1 Hz, 0.5H), 7.46-7.28 (m, 5H), 6.00 (t, J=5.7 Hz, 1H), 5.68-4.82 (m, 10H), 4.70-4.40 (m, 2H), 3.45 (s, 3H), 3.25 (s, 3H), 3.19 (s, 1.5H), 3.18 (s, 1.5H), 3.15 (s, 3H), 3.07 (s, 3H), 2.70 (s, 1.5H), 2.68 (s, 1.5H), 2.66 (s, 1.5H), 2.64 (s, 1.5H), 2.45-2.35 (m, 1H), 2.20-1.85 (m, 8H), 2.03 (s, 3H), 1.75-1.55 (m, 3H), 1.45-0.50 (m, 56H); ESI MS m/z 1341 [C$_{69}$H$_{114}$ClN$_{11}$O$_{13}$+H]$^+$.

Example 23

Preparation of cis- and trans-Cyclosporin Phenylvinyl Chloride

To a stirred solution of the acetate of cyclosporin phenylvinyl chloride from Example 22 (59 mg, 0.040 mmol) in methanol (5 mL) was added potassium carbonate (149 mg, 1.07 mmol) at room temperature. After 12 h at room temperature, methanol was evaporated. Water (20 mL) was added and the mixture was extracted with ethyl acetate (3×70 mL). The organic layer was separated, dried over anhydrous sodium sulfate, and concentrated under vacuum to afford the crude product. The material was purified by semi-preparative HPLC to afford cyclosporin phenylvinyl chloride (35 mg, 63%) as a mixture of cis- and trans-isomers and a white solid: $^1$H NMR (300 MHz, CDCl$_3$) δ 8.10-7.92 (m, 1H), 7.70 (br s, 1H), 7.54 (d, J=6.9 Hz, 2H), 7.38-7.28 (m, 5H), 6.18 (t, J=6.2 Hz, 0.5H), 6.05 (t, J=6.2 Hz, 0.5H), 5.69 (d, J=8.6 Hz, 1H), 5.55 (br s, 1H), 5.37 (dd, J=13.2, 3.8 Hz, 1H), 5.15-4.45 (m, 8H), 3.81 (br s, 1H), 3.53 (s, 1.5H), 3.49 (s, 1.5H), 3.40 (s, 1.5H), 3.38 (s, 1.5H), 3.26 (s, 3H), 3.11 (s, 6H), 2.72 (s, 3H), 2.69 (s, 3H), 2.48-1.53 (m, 14H), 1.50-0.75 (m, 55H); ESI MS m/z 1299 [C$_{67}$H$_{112}$ClN$_{11}$O$_{12}$+H]$^+$; HPLC>99% (AUC), t$_R$=16.65 min.

Example 24

Preparation of the Acetate of Cyclosporin α,β-Unsaturated Aldehyde

A mixture of acetyl-protected cyclosporin A from Example 1 (100 mg, 0.08 mmol), acrolein dimethyl acetal (0.018 mL, 0.16 mmol), Grubbs' catalyst 2$^{nd}$ generation (25 mg, 0.029 mmol) and methylene chloride (1 mL) was heated at 60° C. in a sealed tube for 12 h. The catalyst (25 mg) and acrolein dimethyl acetal (0.018 mL) were refilled, and the mixture was stirred at the same temperature for an additional 12 h, cooled to room temperature, and concentrated in vacuo. The residue was purified by semi-preparative HPLC to afford the acetate of cyclosporin α,β-unsaturated aldehyde (65 mg, 64%) as an off-white solid: $^{1}$H NMR (300 MHz, CDCl$_3$) δ 9.42 (d, J=7.9 Hz, 1H), 8.55 (d, J=9.6 Hz, 1H), 8.02 (d, J=6.8 Hz, 1H), 7.71 (d, J=8.8 Hz, 1H), 7.53 (d, J=7.5 Hz, 1H), 6.73 (ddd, J=15.5, 10.0, 4.5 Hz, 1H), 5.60 (dd, J=15.5, 7.9 Hz, 1H), 5.70-4.40 (m, 12H), 3.46 (s, 3H), 3.27 (s, 3H), 3.22 (s, 3H), 3.21 (s, 3H), 3.13 (s, 3H), 2.68 (s, 3H), 2.66 (s, 3H), 2.50-1.50 (m, 10H), 2.04 (s, 3H), 1.40-0.75 (m, 58H); ESI MS m/z 1259 [C$_{64}$H$_{111}$N$_{10}$O$_{14}$+H]$^{+}$.

Example 25

Preparation of the Acetate of Cyclosporin Vinyl Chloride

Chromium(II) chloride (235 mg, 1.92 mmol) was added to a solution of the acetate of cyclosporin (α,β-unsaturated aldehyde from Example 24 (80 mg, 0.64 mmol) and chloroform (0.05 mL, 0.064 mmol) in THF (3 mL) at room temperature. The mixture was stirred at 50° C. for 4 h and then cooled to room temperature, quenched with water, extracted with ethyl acetate. The combined organic layers were washed with brine, dried over sodium sulfate, filtered, and concentrated in vacuo. The residue was purified by semi-preparative HPLC to afford the acetate of cyclosporin vinyl chloride (25 mg, 30%) as a white solid: $^{1}$H NMR (300 MHz, CDCl$_3$) δ 8.55 (t, J=9.4 Hz, 1H), 8.05 (t, J=6.8 Hz, 1H), 7.76 (t, J=9.2 Hz, 1H), 7.55 (d, J=7.3 Hz, 1H), 6.42 (dd, J=13.1, 10.8 Hz, 1H), 6.06 (d, J=13.1 Hz, 1H), 5.82 (dd, J=15.0, 10.6 Hz, 1H), 5.70-4.35 (m, 13H), 3.44 (s, 3H), 3.25 (s, 3H), 3.23 (s, 3H), 3.20 (s, 3H), 3.11 (s, 3H), 2.68 (s, 3H), 2.66 (s, 3H), 2.50-1.50 (m, 10H), 2.02 (s, 3H), 1.40-0.82 (m, 58H); ESI MS m/z 1291 [C$_{65}$H$_{112}$ClN$_{11}$O$_{13}$+H]$^{+}$.

Example 26

Preparation of Cyclosporin Vinyl Chloride

A mixture of the acetate of cyclosporin vinyl chloride from Example 25 (25 mg, 0.019 mmol), potassium carbonate (50 mg, 0.36 mmol) and methanol (1 mL) was stirred at room temperature overnight, and then diluted with ethyl acetate, washed with water and brine, dried over sodium sulfate, filtered, and concentrated in vacuo. The residue was purified by semi-preparative HPLC to afford cyclosporin vinyl chloride (15 mg, 61%) as a white solid: $^{1}$H NMR (300 MHz, CDCl$_3$) δ 7.98 (d, J=9.2 Hz, 1H), 7.63 (d, J=7.4 Hz, 1H), 7.57 (t, J=7.7 Hz, 1H), 7.22 (d, J=7.8 Hz, 1H), 6.43 (dd, J=13.1, 10.8 Hz, 1H), 6.07 (d, J=13.1 Hz, 1H), 5.91 (dd, J=15.0, 10.8 Hz, 1H), 5.72-3.80 (m, 13H), 3.50 (s, 3H), 3.39 (s, 3H), 3.25 (s, 3H), 3.11 (s, 3H), 3.10 (s, 3H), 2.70 (s, 3H), 2.69 (s, 3H), 2.50-1.50 (m, 11H), 1.40-0.82 (m, 58H); ESI MS m/z 1249 [C$_{63}$H$_{110}$ClN$_{11}$O$_{12}$+H]$^{+}$; HPLC>99% (AUC), t$_R$=14.43 min.

Example 27

Preparation of the Acetate of Cyclosporin Vinyl Bromide

Chromium(II) chloride (235 mg, 1.92 mmol) was added to a solution of the acetate of cyclosporin α,β-unsaturated aldehyde from Example 24 (80 mg, 0.064 mmol) and bromoform (0.084 mL, 0.96 mmol) in THF (3 mL) at room temperature. The mixture was stirred under nitrogen for 4 h and then quenched with water, extracted with ethyl acetate. The combined organic layers were washed with brine, dried over sodium sulfate, filtered, and concentrated in vacuo. The residue was purified by semi-preparative HPLC to afford the acetate of cyclosporin vinyl bromide (13 mg, 15%) as a white solid: $^{1}$H NMR (300 MHz, CDCl$_3$) δ 8.55 (d, J=9.4 Hz, 1H), 8.05 (d, J=6.8 Hz, 1H), 7.71 (d, J=9.2 Hz, 1H), 7.51 (d, J=7.7 Hz, 1H), 6.70 (dd, J=13.4, 10.8 Hz, 1H), 6.16 (d, J=13.4 Hz, 1H), 5.81 (dd, J=15.5, 11.1 Hz, 1H), 5.70-4.35 (m, 13H), 3.44 (s, 3H), 3.25 (s, 3H), 3.23 (s, 3H), 3.20 (s, 3H), 3.11 (s, 3H), 2.68 (s, 3H), 2.66 (s, 3H), 2.50-1.50 (m, 10H), 2.02 (s, 3H), 1.40-0.82 (m, 58H); ESI MS m/z 1334 [C$_{65}$H$_{112}$BrN$_{11}$O$_{13}$+H]$^{+}$.

Example 28

Preparation of Cyclosporin Vinyl Bromide

A mixture of the acetate of cyclosporin vinyl bromide from Example 27 (13 mg, 0.01 mmol), potassium carbonate (30 mg, 0.22 mmol) and methanol (1 mL) was stirred at room temperature overnight, and then diluted with ethyl acetate, washed with water and brine, dried over sodium sulfate, filtered, and concentrated in vacuo. The residue was purified by semi-preparative HPLC to afford cyclosporin vinyl bromide (4 mg, 31%) as a white solid: $^{1}$H NMR (300 MHz, CDCl$_3$) δ 7.95 (d, J=9.8 Hz, 1H), 7.64 (d, J=7.4 Hz, 1H), 7.53 (t, J=8.1 Hz, 1H), 7.20 (d, J=7.4 Hz, 1H), 6.70 (dd, J=13.1, 10.7 Hz, 1H), 6.17 (d, J=13.4 Hz, 1H), 5.90 (dd, J=15.0, 10.7 Hz, 1H), 5.72-3.75 (m, 13H), 3.50 (s, 3H), 3.39 (s, 3H), 3.25 (s, 3H), 3.11 (s, 3H), 3.10 (s, 3H), 2.70 (s, 3H), 2.69 (s, 3H), 2.50-1.50 (m, 11H), 1.40-0.82 (m, 58H); ESI MS m/z 1292 [C$_{63}$H$_{110}$BrN$_{11}$O$_{12}$+H]$^{+}$; HPLC>99% (AUC), t$_R$=14.30 min.

Example 29

Preparation of the Acetate of Cyclosporin Vinyl Iodide

Chromium(II) chloride (340 mg, 2.76 mmol) was added to a solution of the acetate of cyclosporin α,β-unsaturated aldehyde from Example 24 (174 mg, 0.138 mmol) and iodoform (540 mg, 1.38 mmol) in THF (5 mL) at −40° C. The mixture was allowed to warm to 0° C. and stirred under nitrogen for 1 h. The mixture was poured into ice water, extracted with ethyl acetate. The combined organic layers were washed with brine, dried over sodium sulfate, filtered, and concentrated in vacuo. The residue was purified by semi-preparative HPLC to afford the acetate of cyclosporin vinyl iodide (125 mg, 65%) as a light yellow solid: $^{1}$H NMR (300 MHz, CDCl$_3$) δ 8.55 (d, J=9.4 Hz, 1H), 8.07 (d, J=6.8 Hz, 1H), 7.84 (d, J=9.2 Hz, 1H), 7.59 (d, J=7.3 Hz, 1H), 6.95 (dd, J=14.2, 10.6 Hz, 1H), 6.16 (d, J=14.4 Hz, 1H), 5.82 (dd, J=14.9, 10.6 Hz, 1H), 5.70-4.40 (m, 13H), 3.44 (s, 3H), 3.24 (s, 3H), 3.22 (s, 3H), 3.19 (s, 3H), 3.12 (s, 3H), 2.68 (s, 3H), 2.67 (s, 3H), 2.50-1.50 (m, 10H), 2.02 (s, 3H), 1.40-0.82 (m, 58H); ESI MS m/z 1383 [C$_{65}$H$_{112}$IN$_{13}$O$_{13}$+H]$^{+}$.

Example 30

Preparation of Cyclosporin Vinyl Iodide

A mixture of the acetate of cyclosporin vinyl iodide from Example 29 (27 mg, 0.02 mmol), potassium carbonate (40 mg, 0.29 mmol) and methanol (1 mL) was stirred at room temperature for 4 h, and then diluted with ethyl acetate, washed with water and brine, dried over sodium sulfate, filtered, and concentrated in vacuo. The residue was purified by semi-preparative HPLC to afford cyclosporin vinyl iodide (14 mg, 54%) as a white solid: $^1$H NMR (300 MHz, CDCl$_3$) δ 7.95 (d,J=9.7 Hz,1H), 7.64 (d, J=7.5 Hz, 2H), 7.28 (d, J=7.3 Hz, 1H), 6.99 (dd, J=14.6, 10.8 Hz, 1H), 6.20-3.80 (m, 1H), 3.50 (s, 3H), 3.39 (s, 3H), 3.25 (s, 3H), 3.12 (s, 3H), 3.10 (s, 3H), 2.70 (s, 3H), 2.69 (s, 3H), 2.50-1.50 (m, 11H), 1.40-0.82 (m, 58H); ESI MS m/z 1340 [C$_{63}$H$_{110}$IN$_{11}$O$_{12}$+H]$^+$; HPLC>99% (AUC), t$_R$=14.38 min.

Example 31

Preparation of Cyclosporin Fluoride

A 25 mL round bottom flask was charged with cyclosporin A (90 mg, 0.072 mmol), α,α,α-trifluorotoluene (5 mL), 3,3,3-trifluoropropene (200 mg, 2.08 mmol), and tricyclohexylphosphine[1,3-bis(2,4,6-trimethylphenyl)-4,5-dihydroimidazol-2-yl-ene][benzylidine]ruthenium(IV)dichloride (15 mg, 0.018 mmol). The atmosphere was maintained via a balloon filled with 3,3,3-trifluoropropene. The mixture was stirred at 50° C. for 72 h with 3,3,3-trifluoropropene refilled every 24 h. After cooling down to room temperature, solvent was removed in vacuo, the residue was pre-purified by column chromatography (silical gel, 6:1 EtOAc/CH$_3$CN) to give 40 mg of light brown solid. The obtained solid was purified via semi-preparative HPLC to give cyclosporin fluoride (12 mg, 12.7%) as a white solid: $^1$H NMR (CDCl$_3$, 500 MHz) δ 8.25 (d, J=9.8 Hz, 1H), 8.01 (d, J=7.4 Hz, 1H), 7.87 (d, J=7.7 Hz, 1H), 7.56 (d, J=7.3 Hz, 1H), 6.62 (m, 1H), 5.93-5.84 (m, 2H), 5,73 (d, J=6.0 Hz, 1H), 5.51-5.47 (m, 1H), 5.48-5.30 (m, 4H), 5.14 (dd, J=6.3, 3.1 Hz, 1H), 5.03 (t, J=7.5 Hz, 1H), 4.95 (d, J=14.6 Hz, 1H), 4.86 (t, J=8.4 Hz, 1H), 4.73 (t, J=8.5 Hz, 1H), 3.97 (t, J=6.7 Hz, 1H), 3.66 (s, 3H), 3.52 (s, 3H), 3.38.(s, 3H), 3.37 (m, 2H), 3.24 (s, 3H), 3.20 (m, 2H), 2.85 (s, 3H), 2.81 (s, 3H), 2.70 (m, 1H), 2.48 (m, 1H), 2.32-2.05 (m, 7H), 1.90-1.65 (m, 9H), 1.68-0.78 (m, 49H); $^{19}$F NMR (CDCl$_3$, 282 MHz) δ −64.1, −76.3; ESI MS m/z 1256 [C$_{62}$H$_{108}$F$_3$N$_{11}$O$_{12}$+H]$^+$; HPLC 95.2% (AUC), t$_R$=16.65 min.

Example 32

Preparation of Cyclosporin Fluoride

A 25 mL round bottom flask was charged with cyclosporin A (100 mg, 0.08 mmol), dichloromethane (5 mL), 1H,1H, 2H-heptafluoropent-1-ene (200 mg, 1.02 mmol), and tricyclohexylphosphine[1,3-bis(2,4,6-trimethylphenyl)-4,5-dihydroimidazol-2-yl-ene][benzylidine]ruthenium(IV) dichloride (16 mg, 0.019 mmol). The mixture was refluxed at 50° C. for 48 h. After cooling down to room temperature, solvent was removed in vacuo, the residue was pre-purified by column chromatography (silical gel, 6:1 EtOAc/CH$_3$CN) to give 40 mg light brown solid. The obtained solid was purified via semi-preparative HPLC to give cyclosporin fluoride (12 mg, 10.6%) as a white solid: $^1$H NMR (CDCl$_3$, 500 MHz) δ 8.02 (d, J=9.9 Hz, 1H), 7.69 (d, J=7.7 Hz, 1H), 7.49 (d, J=8.1 Hz, 1H), 7.16 (d, J=7.8 Hz, 1H), 6.40 (m, 1H), 5.69 (dd, J=10.1, 4.2 Hz, 1H), 5.53 (d, J=6.0 Hz, 1H), 5.26 (dd, J=16.2, 6.9 Hz, 1H), 5.04-4.99 (m, 2H), 4.92 (dd, J=9.8, 6.0 Hz, 1H), 4.82 (t, J=7.4 Hz, 1H), 4.72 (d, J=14.0 Hz, 1H), 4.62 (d, J=9.5 Hz, 1H), 4.53 (t, J=7.4 Hz, 1H), 3.78 (t, J=8.5 Hz, 1H), 3.52 (s, 3H), 3.38 (s, 3H), 3.25 (s, 3H), 3.12 (s, 3H), 3.11(s, 3H), 2.72 (s, 3H), 2.69 (s, 3H), 2.40 (m, 1H), 2.20-1.50 (m, 11H), 1.48-0.67 (m, 59H); $^{19}$F NMR (CDCl$_3$, 282 MHz): δ −76.3, −80.8, −112.6, −128.3; ESI MS m/z 1357 [C$_{64}$H$_{108}$F$_7$N$_{11}$O$_{12}$+H]$^+$; HPLC 97.7% (AUC), t$_R$=17.66 min.

Example 33

Preparation of Cyclosporin Fluoride

A 25 mL round bottom flask was charged with cyclosporin A (100 mg, 0.08 mmol), dichloromethane (4 mL), 1H,1H, 2H-Perfluoro-1-hexene (200 mg, 1.37 mmol), and tricyclohexylphosphine[1,3-bis(2,4,6-trimethylphenyl)-4,5-dihydroimidazol-2-yl-ene][benzylidine]ruthenium(IV) dichloride (15 mg, 0.018 mmol). The mixture was refluxed under nitrogen at 50° C. for 20 h. After cooling down to room temperature, solvent was removed in vacuo, the residue was pre-purified by column chromatography (silical gel, 6:1 EtOAc/CH$_3$CN) to give 90 mg light brown solid. The obtained solid was purified via semi-preparative HPLC to give the target cyclosporin fluoride (22mg, 18.8%) as white solid: $^1$H NMR (CDCl$_3$, 500 MHz) δ 8.00 (d, J=9.9 Hz, 1H), 7.67 (d, J=7.7 Hz, 1H), 7.47 (d,J=8.1 Hz, 1H), 7.14 (d, J=7.8 Hz, 1H), 6.38 (m, 1H), 5.67 (dd, J=10.1, 4.2 Hz, 1H), 5.51 (d, J=6.0 Hz, 1H), 5.24 (dd, J=16.2, 6.9 Hz, 1H), 5.04-4.99 (m, 2H), 4.90 (dd, J=9.8, 6.0 Hz, 1H), 4.80 (t, J=7.4 Hz, 1H), 4.70 (d, J=14.0 Hz, 1H), 4.60 (t, J=9.5 Hz, 1H), 4.51 (t, J=7.4 Hz, 1H), 3.78 (t, J=8.5Hz, 1H), 3.50 (s, 3H), 3.36 (s, 3H), 3.23 (s, 3H), 3.08 (s, 3H), 3.07 (s, 3H), 2.68 (s, 3H), 2.65 (s, 3H), 2.40 (m, 1H), 2.18-1.88 (m, 6H), 1.87-1.50 (m, 9H), 1.48-0.67 (m, 55H); $^{19}$F NMR (CDCl$_3$, 282 MHz) δ −76.3, −81.5, −112.0, −124.6, −126.2; ESI MS m/z 1406 [C$_{65}$H$_{108}$F$_9$N$_{11}$O$_{12}$+H]$^+$; HPLC>99.1% (AUC), t$_R$=30.84 min.

Example 34

Preparation of Cyclosporin Allylic Fluoride

A 25 mL round bottom flask was charged with cyclosporin A (100 mg, 0.083 mmol), allyl fluoride (50 mg, 0.83 mmol), and tricyclohexylphosphine[1,3-bis(2,4,6-trimethylphenyl)-4,5-dihydroimidazol-2-yl-ene][benzylidine]ruthenium(IV) dichloride (34 mg, 0.04 mmol) and 5 mL of CH$_2$Cl$_2$. The mixture was refluxed under nitrogen overnight. After cooling down to room temperature, solvent was removed in vacuo. The residue was pre-purified by column chromatography (silica gel, 1:1 hexane/acetone) then purified via semi-preparative HPLC to give cyclosporin allylic fluoride (52 mg, 51.2%) as a white solid: $^1$H NMR (CDCl$_3$, 300 MHz) δ 8.04 (d, J=9.6 Hz, 1H), 7.68 (d, J=7.3 Hz, 1H), 7.57 (d, J=8.2 Hz, 1H), 7.23 (d, J=7.8 Hz, 1H), 5.80-5.62 (m, 6H), 5.50 (d, J=6.2 Hz, 1H), 5.30 (dd, J=6.9, 3.5 Hz, 1H), 5.11-4.93 (m, 5H), 4.84 (d, J=5.6 Hz, 2H), 4.78 (d, J=15.6 Hz, 1H), 4.68 (d, J=7.1 Hz, 1H), 4.62 (d, J=8.9 Hz, 1H), 4.51 (t, J=7.3 Hz, 1H), 3.81 (t, J=6.4 Hz, 1H), 3.50 (s, 3H), 3.40 (s, 3H), 3.25 (s, 3H), 3.12 (s, 3H), 3.11 (s, 3H), 2.71 (s, 3H), 2.69 (s, 3H), 2.20-0.62 (m, 65H); ESI MS m/z 1221 [C$_{62}$H$_{110}$FN$_{11}$O$_{12}$+H]$^+$; HPLC 94.1% (AUC), t$_R$=15.0 min.

Example 35

Preparation of the Acetate of Cyclosporin Allylic Chloride

Acetyl-protected cyclosporine A (100 mg, 0.08 mmol) was dissolved in 5 mL of CH$_2$Cl$_2$, and then allyl chloride (61 mg, 0.8 mmol) and Grubbs' catalyst $3^{rd}$ generation (25 mg, 0.04 mmol) were added. The mixture was refluxed under $N_2$ for 48 h. After that, the solvent was removed in vacuo, and the residue was purified via silica gel column (EtOAc) to give the acetate of cyclosporin allylic chloride (97 mg, yield 94%) as a light yellow solid: $^1$H NMR (CDCl$_3$, 300 MHz) δ 8.54 (d, J=9.6 Hz, 1H), 8.04 (d, J=6.9 Hz, 1H), 7.70 (d, J=9.0 Hz, 1H), 7.51 (d, J=7.8 Hz, 1H), 5.68 (dd, J=11.1, 3.9 Hz, 1H), 5.53-5.47 (m, 6H), 5.17 (d, J=7.8 Hz, 2H), 4.97 (d, J=11.1 Hz, 3H), 4.84 (t, J=7.2 Hz, 1H), 4.75 (t, J=9.9 Hz, 1H), 4.64 (d, J=13.8 Hz, 1H), 4.43 (t, J=6.9 Hz, 1H), 3.98 (d, J=4.5 Hz, 2H), 3.45 (s, 3H), 3.25 (s, 3H), 3.24 (s, 3H), 3.20 (s, 3H), 3.16 (m, 2H), 3.11 (s, 3H), 2.67 (s, 3H), 2.66 (s, 3H), 2.41 (m, 1H), 2.22-0.78 (m, 66H); ESI MS m/z 1279 [C$_{64}$H$_{112}$ClN$_{11}$O$_{13}$+H]$^+$.

Example 36

Preparation of Cyclosporin Allylic Chloride

The acetate of cyclosporin allylic chloride from Example 35 (30 mg, 0.023 mmol) was dissolved in 2 mL of methanol, and then K$_2$CO$_3$ (190 mg, 1.127 mmol) was added. The mixture was stirred at room temperature for 1.5 h, and then diluted with 100 mL of EtOAc, washed with H$_2$O (10 mL), brine (10 mL), dried over Na$_2$SO$_4$, solvent was removed in vacuo, the residue was purified via semi-preparative HPLC to give cyclosporin allylic chloride (15 mg, 51%) as a white solid: $^1$H NMR (CDCl$_3$, 500 MHz) δ 8.05 (d, J=10.1 Hz, 1H), 7.65 (d, J=7.3 Hz, 1H), 7.49 (d, J=8.1 Hz, 1H), 7.16 (d, J=7.8 Hz, 1H), 5.70 (m, 2H), 5.57 (t, J=7.8 Hz, 1H), 5.49 (d, J=6.4 Hz, 1H), 5.28 (m, 1H), 5.12-4.94 (m, 4H), 4.82 (q, J=7.0 Hz, 1H), 4.72 (d, J=13.9 Hz, 1H), 4.65 (t, J=7.0 Hz, 1H), 4.53 (t, J=7.2 Hz, 1H), 4.02 (d, J=7.0 Hz, 1H), 3.82 (t, J=6.6 Hz, 1H), 3.51 (s, 3H), 3.40 (s, 3H), 3.26 (s, 3H), 3.11 (s, 6H), 2.70 (s, 3H), 2.68 (s, 3H), 2.48 (m, 2H), 2.22-0.62 (m, 68H); ESI MS m/z 1237 [C$_{62}$H$_{110}$ClN$_{11}$O$_{12}$+H]$^+$; HPLC 97.9% (AUC), t$_R$=15.5 min.

Example 37

Preparation of Cyclosporin Amine

The acetate of cyclosporin allylic chloride from Example 35 (35 mg, 0.027 mmol) was mixed with dimethyl amine in THF (1.0 M, 6.0 mL, 6.0 mmol). The mixture was stirred under nitrogen at room temperature overnight. After that, the solvent was removed in vacuo to give the crude acetyl cyclosporin amine (40 mg). The crude product (40 mg, 0.03 mmol) was dissolved in 3 mL of methanol, and then K$_2$CO$_3$ (215 mg, 1.55 mmol) was added. The mixture was stirred at room temperature for 4 h, then diluted with 100 mL of EtOAc, washed with brine (3×10 mL), dried over Na$_2$SO$_4$. Solvent was removed in vacuo, and the residue was purified via semi-preparative HPLC to give cyclosporin amine (10.1 mg, 26%) as a white solid: $^1$H NMR (CDCl$_3$, 300 MHz) δ 8.18 (d, J=9.6 Hz, 1H), 7.75 (d, J=7.5 Hz, 1H), 7.64 (d, J=8.1 Hz, 1H), 7.24 (d, J=8.2 Hz, 1H), 5.92 (m, 1H), 5.69 (dd, J=11.2, 3.7 Hz, 2H), 5.50 (m, 4H), 5.23 (dd, J=11.6, 3.3 Hz, 2H), 5.11-4.96 (m, 8H), 4.85 (t, J=7.2 Hz, 2H), 4.69 (d, J=13.6 Hz, 1H), 4.62 (t, J=8.8 Hz, 1H), 4.52 (t, J=7.4 Hz, 1H), 3.59 (t, J=6.4 Hz, 1H), 3.49 (s, 3H), 3.39 (s, 3H), 3.24 (s, 3H), 3.14 (s, 3H), 3.11 (s, 3H), 2.78 (dd, J=9.1, 3.1 Hz, 8H), 2.69 (s, 3H), 2.68 (s, 3H), 2.50-0.62 (m, 60H); ESI MS m/z 1246 [C$_{64}$H$_{116}$N$_{12}$O$_{12}$+H]$^+$; HPLC 97.3% (AUC), t$_R$=13.5 min.

Example 38

Preparation of Cyclosporin Pyrrolidine

The acetate of cyclosporin allylic chloride from Example 35 (13 mg, 0.01 mmol) and pyrrolidine (7 mg, 0.1 mmol) were dissolved in 2 mL of CH$_2$Cl$_2$, and the mixture was stirred at room temperature under nitrogen for 48 h. The solvent was removed in vacuo to give the crude acetyl pyrrolidine compound (13 mg). The crude product (13 mg, 0.01 mmol) was dissolved in 2 mL of methanol, and then K$_2$CO$_3$ (50 mg, 0.36 mmol) was added. The mixture was stirred at room temperature for 48 h, then diluted with 100 mL of EtOAc, washed with brine (3×10 mL), dried over Na$_2$SO$_4$. Solvent was removed in vacuo, and the residue was purified via semi-preparative HPLC to give cyclosporin pyrrolidine (3 mg, 23%) as a white solid: $^1$H NMR (CDCl$_3$, 500 MHz) δ 8.20 (d, J=9.6 Hz, 1H), 7.74 (d, J=7.2 Hz, 1H), 7.60 (d, J=8.2 Hz, 1H), 7.22 (d, J=7.7 Hz, 1H), 5.82 (m, 1H), 5.70 (dd, J=11.0, 3.9 Hz, 1H), 5.52 (m, 1H), 5.45 (d, J=6.3 Hz, 1H), 5.23 (dd, J=12.0, 4.8 Hz, 1H), 5.15-4.94 (m, 6H), 4.83 (t, J=7.3 Hz, 1H), 4.70 (d, J=13.8 Hz, 1H), 4.62 (t, J=8.8 Hz, 1H), 4.52 (t, J=7.4 Hz, 1H), 3.90 (m, 1H), 3.72 (m, 2H), 3.50 (s, 3H), 3.41 (s, 3H), 3.26 (s, 3H), 3.25 (m, 2H), 3.15 (s, 3H), 3.14 (s, 3H), 3.02-2.85 (m, 10H), 2.69 (s, 3H), 2.67 (s, 3H), 2.42 (m, 2H), 2.22-0.62 (m, 61H); ESI MS m/z 1272 [C$_{66}$H$_{118}$N$_{12}$O$_{12}$+H]$^+$; HPLC 96.6% (AUC), t$_R$=14.4 min.

Example 39

Preparation of Cyclosporin Acetamide

The acetate of cyclosporin allylic chloride from Example 35 (30 mg, 0.023 mmol) was mixed with methylamine in THF (2.0 M, 4.0 mL, 8.0 mmol). The mixture was stirred at room temperature under nitrogen overnight. After that, the solvent was removed in vacuo to give the crude acetyl cyclosporin methylamine (30 mg). The methylamine (30 mg, 0.024 mmol) was dissolved in 4 mL of CH$_2$Cl$_2$, and then Ac$_2$O (48 mg, 0.47 mmol), pyridine (37 mg, 0.47 mmol) and DMAP (3 mg, 0.024 mmol) were added. The mixture was stirred under nitrogen at room temperature overnight, then diluted with 100 mL of EtOAc, washed with brine (3×10 mL), and dried over Na$_2$SO$_4$. Solvents were removed in vacuo, and the residue was purified via semi-preparative HPLC to give cyclosporin acetamide (12 mg, 39%) as a white solid. $^1$H NMR (CDCl$_3$, 300 MHz) δ 8.49 (d, J=8.1 Hz, 1H), 8.04 (d, J=6.9 Hz, 1H), 7.82 (t, J=6.9 Hz, 1H), 7.55 (d, J=6.0 Hz, 1H), 5.68 (dd, J=12.2, 4.0 Hz, 1H), 5.28 (m, 3H), 5.17 (t, J=6.0 Hz, 2H), 4.96 (d, J=11.1 Hz, 3H), 4.84 (t, J=7.2 Hz, 2H), 4.68 (d, J=14.1 Hz, 3H), 4.44 (t, J=7.5 Hz, 1H), 3.88 (d, J=5.1 Hz, 1H), 3.48 (s, 3H), 3.25 (s, 3H), 3.22 (s, 3H), 3.20 (s, 3H), 3.10 (s, 3H), 2.93 (d, J=6.9 Hz, 4H), 2.68 (s, 3H), 2.67 (s, 3H), 2.24-2.18 (m, 7H), 2.01 (s, 3H), 2.12-0.62 (m, 63H); ESI MS m/z 1315 [C$_{67}$H$_{118}$N$_{12}$O$_{14}$+H]$^+$.

Example 40

Preparation of Cyclosporin Amide

Cyclosporin amide from Example 39 (12 mg, 0.009 mmol) was dissolved in 2 mL of methanol, and then K$_2$CO$_3$ (63 mg, 0.456 mmol) was added. The mixture was stirred at room temperature for 4 h, then diluted with 100 mL of EtOAc, washed with brine (3×10 mL), dried over $Na_2SO_4$. Solvents were removed in vacuo, and the residue was purified via semi-preparative HPLC to give cyclosporin amide (4.5 mg, 38%) as a white solid: $^1$H NMR ($CD_2Cl_2$, 500 MHz) δ 8.00 (d, J=10.5 Hz, 1H), 7.59 (d, J=4.5 Hz, 2H), 7.25 (s, 1H), 5.69 (dd, J=10.5, 4.0 Hz, 1H), 5.63 (m, 1H), 5.47 (d, J=4.5 Hz, 2H), 5.28 (m, 1H), 5.07 (d, J=6.5 Hz, 3H), 5.00 (t, J=7.0 Hz, 2H), 4.81 (t, J=7.0 Hz, 2H), 4.70 (d, J=14.0 Hz, 1H), 4.62 (t, J=9.0 Hz, 1H), 4.47 (t, J=7.5 Hz, 1H), 4.00-3.87 (m, 3H), 3.80 (t, J=6.5 Hz, 1H), 3.45 (s, 3H), 3.36 (s, 3H), 3.22 (s, 3H), 3.10 (s, 6H), 2.93 (d, J=9.0 Hz, 6H), 2.70 (s, 3H), 2.66 (s, 3H), 2.45 (m, 2H), 2.17 (s, 3H), 2.12-0.62 (m, 61H); ESI MS m/z 1274 $[C_{65}H_{116}N_{12}O_{13}+H]^+$; HPLC 93.7% (AUC), $t_R$=14.3 min.

Example 41

Preparation of Cyclosporin Piperidine

A solution of the acetate of cyclosporin allylic chloride from Example 35 (50 mg, 0.04 mmol) and piperidine (33 mg, 0.4 mmol) in methylene chloride (3 mL) was stirred overnight at room temperature under $N_2$ atmosphere. Mixture was diluted with ether and extracted with 1 N HCl. Aqueous layer was neutralized with saturated sodium bicarbonate solution, extracted with ethyl acetate, washed with brine, dried over sodium sulfate, and concentrated in vacuo to afford the crude cyclosporin acetate (12 mg) as an off-white solid. A solution of the crude acetate (12 mg, 0.009 mmol) and potassium carbonate (13 mg, 0.099 mmol) in methanol (1 mL) was stirred overnight at room temperature under $N_2$ atmosphere. Mixture was diluted with ethyl acetate, washed with saturated sodium bicarbonate solution and brine, dried over sodium sulfate, and concentrated in vacuo. The crude product was purified by semi-preparative HPLC to afford cyclosporin piperidine (8.3 mg, 17%) as an off-white solid: $^1$H NMR (300 MHz, $CD_2Cl_2$) δ 8.15 (d, J=9.7 Hz, 1H), 7.70 (d, J=7.3 Hz, 1H), 7.61 (d, J=8.3 Hz, 1H), 7.25 (d, J=7.8 Hz, 1H), 5.71 (d, J=6.8 Hz, 1H), 5.44 (d, J=7.5 Hz, 1H), 5.40-4.90 (m, 6H), 4.84 (t, J=4.38 Hz, 2H), 4.79 (s, 1H), 4.69 (dd, J=17.4, 14.0 Hz, 2H), 4.47 (t, J=14.3 Hz, 2H), 4.16 (d, J=10.7 Hz, 2H), 3.47 (s, 3H), 3.41 (s, 3H), 3.39 (s, 3H), 3.26 (s, 3H), 3.15 (s, 3H), 2.71 (s, 3H), 2.69 (s, 3H), 1.51 (d, J=7.3 Hz, 2H), 1.40-1.20 (m, 22H), 1.40-0.80 (m, 54H); ESI MS m/z 1286 $[C_{67}H_{120}N_{12}O_{12}+H]^+$; HPLC 96.4% (AUC), $t_R$=14.69 min.

Example 42

Preparation of Cyclosporin Morpholine

A solution of the acetate of cyclosporin allylic chloride from Example 35 (75 mg, 0.058 mmol) and morpholine (51 mg, 0.58 mmol) in methylene chloride (3 mL) was stirred overnight at room temperature under $N_2$ atmosphere. The mixture was concentrated in vacuo. The residue and potassium carbonate (114 mg, 0.83 mmol) were dissolved in methanol (3 mL) and allowed to stir overnight at room temperature under $N_2$ atmosphere. The mixture was diluted with ethyl acetate, washed with saturated sodium bicarbonate solution and brine, dried over sodium sulfate, and concentrated in vacuo. The crude product was purified by semi-preparative HPLC to afford cyclosporin morpholine (28.2 mg, 29%) as a pale yellow solid: $^1$H NMR (300 MHz, $CD_2Cl_2$) δ 7.97 (d, J=9.6 Hz, 1H), 7.57 (d, J=6.9 Hz, 1H), 7.44 (d, J=7.4 Hz, 1H), 7.15 (d, J=7.6 Hz, 1H), 5.67 (d, J=6.8 Hz, 1H), 5.44 (d, J=6.2 Hz, 1H), 5.10-4.90 (m, 11H), 4.79 (t, J=14.5 Hz, 2H), 4.72 (s, 1H), 4.63 (dd, J=14.7, 6.4 Hz, 2H), 4.42 (t, J=14.2 Hz, 2H), 3.45 (s, 3H), 3.36 (s, 3H), 3.21 (s, 3H), 3.09 (s, 3H), 3.08 (s, 3H), 2.68 (s, 3H), 2.56 (s, 3H), 2.50-1.40 (m, 19H), 1.27-0.70 (m, 54H); ESI MS m/z 1288 $[C_{66}H_{118}N_{12}O_{13}+H]^+$; HPLC>99% (AUC), $t_R$=15.16 min.

Example 43

Preparation of Cyclosporin Thiomorpholine

A solution of the acetate of cyclosporin allylic chloride from Example 35 (60 mg, 0.047 mmol) and thiomorpholine (48 mg, 0.47 mmol) in methylene chloride (3 mL) was stirred overnight at room temperature under $N_2$ atmosphere. The mixture was concentrated in vacuo. The residue and potassium carbonate (102 mg, 0.740 mmol) were dissolved in methanol (3 mL) and allowed to stir overnight at room temperature under $N_2$ atmosphere. The mixture was diluted with ethyl acetate, washed with saturated sodium bicarbonate solution and brine, dried over sodium sulfate, and concentrated in vacuo. The crude product was purified by semi-preparative HPLC to afford cyclosporine thiomorpholine (28.8 mg, 33%) as a white solid: $^1$H NMR (300 MHz, $CD_2Cl_2$) δ 7.96 (d, J=9.7 Hz, 1H), 7.59 (d, J=7.2 Hz, 1H), 7.44 (d, J=7.4 Hz, 1H), 7.15 (d, J=7.7 Hz, 1H), 5.67 (dd, J=10.9, 4.1 Hz, 1H), 5.05-5.48 (m, 9H), 5.43 (d, J=6.6 Hz, 2H), 5.28 (d, J=3.8 Hz, 1H), 5.24 (d, J=3.8 Hz, 1H), 5.15-4.89 (m, 5H), 4.79 (t, J=14.5 Hz, 2H), 4.72 (s, 1H), 4.64 (dd, J=14.8, 5.8 Hz, 2H), 4.23 (t, J=14.5 Hz, 2H), 3.44 (s, 3H), 3.35 (s, 3H), 3.21 (s, 3H), 3.09 (s, 3H), 3.08 (s, 3H), 2.68 (s, 3H), 2.65 (s, 3H), 2.50-1.40 (m, 15H), 1.27-0.70 (m, 54H): ESI MS m/z 1304 $[C_{66}H_{118}N_{12}O_{12}S+H]^+$; HPLC>99% (AUC), $t_R$=13.00 min.

Example 44

Preparation of Cyclosporin Methylpiperazine

A solution of the acetate of cyclosporin allylic chloride from Example 35 (75 mg, 0.058 mmol) and methylpiperazine (58 mg, 0.58 mmol) in methylene chloride (3 mL) was stirred overnight at room temperature under $N_2$ atmosphere. The mixture was concentrated in vacuo. The residue and potassium carbonate (102 mg, 0.740 mmol) were dissolved in methanol (3 mL) and allowed to stir overnight at room temperature under $N_2$ atmosphere. The mixture was diluted with ethyl acetate, washed with saturated sodium bicarbonate solution and brine, dried over sodium sulfate, and concentrated in vacuo. The crude product was purified by semi-preparative HPLC to afford cyclosporin methylpiperazine (36.2 mg, 42%) as an off-white solid: $^1$H NMR (300 MHz, $CD_2Cl_2$) δ 7.95 (d, J=9.6 Hz, 1H), 7.58 (d, J=7.1 Hz, 1H), 7.42 (d, J=8.2 Hz, 1H), 7.15 (d, J=7.5 Hz, 1H), 5.67 (d, J=7.1 Hz, 1H), 5.43 (d, J=6.3 Hz, 1H), 5.15-4.90 (m, 10H), 4.79 (t, J=14.6 Hz, 2H), 4.72 (s, 1H), 4.64 (dd, J=14.3, 5.3 Hz, 2H), 4.42 (t, J=14.4 Hz, 2H), 3.45 (s, 3H), 3.36 (s, 3H), 3.21 (s, 3H), 3.09 (s, 3H), 3.07 (s, 3H), 2.69 (s, 3H), 2.65 (s, 3H), 2.28 (s, 3H), 2.15-1.40 (m, 19H), 1.27-0.70 (m, 55H); ESI MS m/z 1301 $[C_{67}H_{121}N_{13}O_{12}+H]^+$; HPLC>99% (AUC), $t_R$=15.89 min.

Example 45

Preparation of the Acetate of Cyclosporin ene-ene-yne

Zinc chloride (1.0 M in ether, 0.62 mL, 0.62 mmol) was added to a solution of 1-propynylmagnesium bromide (0.5 M in THF, 1.24 mL, 0.62 mmol) in THF (1 mL) at 0° C. and the mixture was stirred under nitrogen for 10 min. The ice bath was removed and the mixture was warmed to room temperature. The acetate of cyclosporin vinyl iodide from Example 29 (85 mg, 0.062 mmol) in THF (2 mL) was added, followed by addition of bis(triphenylphosphine)dichloropalladium(II) (4.3 mg, 0.0062 mmol). The mixture was stirred at room temperature for 1 h, quenched with saturated aqueous ammonium chloride, extracted with ethyl acetate. The combined organic layers were washed with brine, dried over sodium sulfate, filtered and concentrated in vacuo. The residue was purified by semi-preparative HPLC to afford the acetate of cyclosporin ene-ene-yne (17 mg, 22%) as a yellow oil: $^1$H NMR (300 MHz, CDCl$_3$) δ 8.56 (d, J=9.7 Hz, 1H), 8.05 (d, J=6.8 Hz, 1H), 7.64 (d, J=9.2 Hz, 1H), 7.50 (d, J=7.6 Hz, 1H), 6.45 (dd, J=15.5, 10.8 Hz, 1H), 5.90 (dd, J=15.3, 10.8 Hz, 1H), 5.70-4.40 (m, 14H), 3.44 (s, 3H), 3.25 (s, 3H), 3.20 (s, 6H), 3.10 (s, 3H), 2.68 (s, 3H), 2.66 (s, 3H), 2.50-1.50 (m, 10H), 2.01 (s, 3H), 1.96 (d, J=2.0 Hz, 3H), 1.40-0.82 (m, 58H); ESI MS m/z 1295 $[C_{68}H_{115}N_{11}O_{13}+H]^+$.

Example 46

Preparation of Cyclosporin ene-ene-yne

A mixture of the acetate of cyclosporin ene-ene-yne from Example 45 (17 mg, 0.013 mmol), potassium carbonate (30 mg, 0.22 mmol) and methanol (1 mL) was stirred at room temperature overnight, and then diluted with ethyl acetate, washed with water and brine, dried over sodium sulfate, filtered, and concentrated in vacuo. The residue was purified by semi-preparative HPLC to afford cyclosporin ene-ene-yne (6 mg, 36%) as a white solid: $^1$H NMR (300 MHz, CDCl$_3$) δ 7.98 (d, J=9.4 Hz, 1H), 7.65 (d, J=7.4 Hz, 1H), 7.52 (d, J=8.2 Hz, 1H), 7.19 (d, J=7.8 Hz, 1H), 6.47 (dd, J=15.5, 10.8 Hz, 1H), 5.99 (dd, J=15.1, 10.8 Hz, 1H), 5.78-3.75 (m, 14H), 3.51 (s, 3H), 3.39 (s, 3H), 3.25 (s, 3H), 3.11 (s, 3H), 3.10 (s, 3H), 2.71 (s, 3H), 2.69 (s, 3H), 2.50-1.50 (m, 11H), 1.96 (d, J=2.0 Hz, 3H), 1.40-0.82 (m, 58H); ESI MS m/z 1252 $[C_{66}H_{113}N_{11}O_{12}+H]^+$; HPLC>99% (AUC), $t_R$=14.09 min.

Example 47

Preparation of the Acetate of Cyclosporin ene-ene-yne

A mixture of the acetate of cyclosporin vinyl iodide from Example 29 (250 mg, 0.180 mmol), 3-butyn-2-ol (0.13 mL, 1.8 mmol), bis(triphenylphosphine)dichloropalladium(II) (13 mg, 0.018 mmol), copper(I) iodide (7 mg, 0.036 mmol) and triethylamine (2 mL) was stirred under nitrogen at room temperature for 4 h. The mixture was diluted with ethyl acetate, filtered through a pad of silica gel, washed with ethyl acetate. The filtrate was concentrated in vacuo and the residue was purified by semi-preparative HPLC to afford the acetate of cyclosporin ene-ene-yne (166 mg, 70%) as a white solid: $^1$H NMR (300 MHz, CDCl$_3$) δ 8.53 (d, J=9.5 Hz, 1H), 8.05 (d, J=7.0 Hz, 1H), 7.72 (d, J=9.0 Hz, 1H), 7.53 (d, J=7.6 Hz, 1H), 6.50 (dd, J=15.5, 10.8 Hz, 1H), 5.93 (dd, J=15.0, 10.8 Hz, 1H), 5.75-4.40 (m, 15H), 3.44 (s, 3H), 3.25 (s, 3H), 3.22 (s, 3H), 3.20 (s, 3H), 3.10 (s, 3H), 2.68 (s, 3H), 2.67 (s, 3H), 2.50-1.50 (m, 10H), 2.02 (s, 3H), 1.40-0.82 (m, 62H); ESI MS m/z 1324 $[C_{69}H_{117}N_{11}O_{14}+H]^+$.

Example 48

Preparation of Cyclosporin ene-ene-yne

A mixture of the acetate of cyclosporin ene-ene-yne from Example 47 (11 mg, 0.008 mmol), potassium carbonate (30 mg, 0.22 mmol) and methanol (1 mL) was stirred at room temperature overnight, and then diluted with ethyl acetate, washed with water and brine, dried over sodium sulfate, filtered, and concentrated in vacuo. The residue was purified by semi-preparative HPLC to afford cyclosporin ene-ene-yne (5 mg, 45%) as a white solid: $^1$H NMR (300 MHz, CDCl$_3$) δ 7.79 (t, J=9.5 Hz, 1H), 7.56 (d, J=8.0 Hz, 1H), 7.48 (d, J=9.0 Hz, 1H), 7.18 (d, J=7.6 Hz, 1H), 6.50 (dd, J=15.5, 10.8 Hz, 1H), 6.02 (dd, J=15.2, 10.8 Hz, 1H), 5.75-3.75 (m, 15H), 3.51 (s, 3H), 3.38 (s, 3H), 3.24 (s, 3H), 3.11 (s, 3H), 3.09 (s, 3H), 2.70 (s, 3H), 2.69 (s, 3H), 2.50-1.50 (m, 11H), 1.40-0.82 (m, 62H); ESI MS m/z 1282 $[C_{67}H_{115}N_{11}O_{13}+H]^+$; HPLC>99% (AUC), $t_R$=13.42 min.

Example 49

Preparation of the Acetate of Cyclosporin ene-ene-yne-ene

A mixture of the crude acetate of cyclosporin ene-ene-yne from Example 47 (136 mg, 0.10 mmol), Burgess reagent (119 mg, 0.50 mmol) and benzene (2 mL) was heated at 70° C. for 5 h, and then cooled to room temperature, diluted with ether, washed with water and brine, dried over sodium sulfate, filtered, and concentrated in vacuo. The residue was purified by semi-preparative HPLC to afford the desired acetate of cyclosporin ene-ene-yne-ene (10 mg, 7%) as a white solid: $^1$H NMR (300 MHz, CDCl$_3$) δ 8.53 (d, J=9.8 Hz, 1H), 8.05 (d, J=6.8 Hz, 1H), 7.76 (d, J=9.0 Hz, 1H), 7.56 (d, J=7.6 Hz, 1H), 6.57 (dd, J=14.5, 11.0 Hz, 1H), 5.93 (dd, J=14.3, 10.8 Hz, 1H), 5.76-4.40 (m, 17H), 3.44 (s, 3H), 3.26 (s, 3H), 3.23 (s, 3H), 3.20 (s, 3H), 3.11 (s, 3H), 2.67 (s, 3H), 2.66 (s, 3H), 2.50-1.50 (m, 10H), 2.02 (s, 3H), 1.40-0.82 (m, 58H); ESI MS m/z 1307 $[C_{69}H_{115}N_{11}O_{13}+H]^+$.

Example 50

Preparation of Cyclosporin ene-ene-yne-ene

A mixture of the acetate of cyclosporin ene-ene-yne-ene from Example 49 (10 mg, 0.008 mmol), potassium carbonate (30 mg, 0.22 mmol) and methanol (1 mL) was stirred at room temperature for 8 h, and then diluted with ethyl acetate, washed with water and brine, dried over sodium sulfate, filtered, and concentrated in vacuo. The residue was purified by semi-preparative HPLC to afford cyclosporin ene-ene-yne-ene (3 mg, 30%) as a white solid: $^1$H NMR (300 MHz, CDCl$_3$) δ 8.01 (d, J=10.0 Hz, 1H), 7.63 (d, J=7.0 Hz, 1H), 7.48 (d, J=9.0 Hz, 1H), 7.16 (d, J=8.5 Hz, 1H), 6.57 (dd, J=15.5, 10.5 Hz, 1H), 6.03 (dd, J=14.5, 10.5 Hz, 1H), 5.93 (ddd, J=17.5, 11.0, 2.0 Hz, 1H), 5.72-3.75 (m, 16H), 3.51 (s, 3H), 3.39 (s, 3H), 3.26 (s, 3H), 3.11 (s, 6H), 2.70 (s, 3H), 2.68 (s, 3H), 2.50-1.50 (m, 11H), 1.40-0.82 (m, 58H); ESI MS m/z 1265 $[C_{67}H_{113}N_{11}O_{12}+H]^+$; HPLC 90.8% (AUC), $t_R$=14.55 min.

Example 51

Preparation of the Acetate of Cyclosporin ene-ene-yne

A mixture of the acetate of cyclosporin vinyl iodide from Example 29 (56 mg, 0.041 mmol), (trimethylsilyl)acetylene (0.056 mL, 0.41 mmol), bis(triphenylphosphine)dichloropalladium(II) (5.7 mg, 0.0082 mmol), copper(I) iodide (3.1 mg, 0.016 mmol), and triethylamine (1 mL) was stirred under nitrogen at room temperature for 1 h, and then diluted with ethyl acetate, washed with brine, dried over sodium sulfate, filtered, and concentrated in vacuo. The residue was purified by semi-preparative HPLC to afford the acetate of cyclosporin ene-ene-yne (34 mg, 64%) as a light yellow solid: $^1$H NMR (300 MHz, CDCl$_3$) δ 8.55 (d, J=9.2 Hz, 1H), 8.04 (d, J=6.8 Hz, 1H), 7.68 (d, J=9.0 Hz, 1H), 7.53 (d, J=7.2 Hz, 1H), 6.55 (dd, J=15.5, 10.8 Hz, 1H), 5.90 (dd, J=14.8, 10.8 Hz, 1H), 5.70-4.40 (m, 14H), 3.43 (s, 3H), 3.24 (s, 3H), 3.22 (s, 3H), 3.19 (s, 3H), 3.10 (s, 3H), 2.67 (s, 3H), 2.65 (s, 3H), 2.50-1.50 (m, 10H), 2.00 (s, 3H), 1.40-0.82 (m, 58H), 0.17 (s, 9H); ESI MS m/z 1353 [C$_{70}$H$_{121}$N$_{11}$O$_{13}$Si+H]$^+$.

Example 52

Preparation of Cyclosporin ene-ene-yne

A mixture of the acetate of cyclosporin ene-ene-yne from Example 51 (34 mg, 0.025 mmol), potassium carbonate (30 mg, 0.22 mmol) and methanol (1 mL) was stirred at room temperature overnight, and then diluted with ethyl acetate, washed with water and brine, dried over sodium sulfate, filtered, and concentrated in vacuo. The residue was purified by semi-preparative HPLC to afford cyclosporin ene-ene-yne (15 mg, 48%) as a white solid: $^1$H NMR (300 MHz, CDCl$_3$) δ 7.98 (d, J=9.2 Hz, 1H), 7.65 (d, J=6.8 Hz, 1H), 7.61 (d, J=9.0 Hz, 1H), 7.25 (d, J=7.2 Hz, 1H), 6.64 (dd, J=15.6, 10.7 Hz, 1H), 6.02 (dd, J=14.9, 10.7 Hz, 1H), 5.80-3.75 (m, 14H), 3.50 (s, 3H), 3.39 (s, 3H), 3.25 (s, 3H), 3.12 (s, 3H), 3.10 (s, 3H), 2.98 (d, J=2.2 Hz, 1H), 2.70 (s, 3H), 2.69 (s, 3H), 2.50-1.50 (m, 11H), 1.40-0.82 (m, 58H); ESI MS m/z 1239 [C$_{65}$H$_{111}$N$_{11}$O$_{12}$+H]$^+$; HPLC>99% (AUC), t$_R$=19.40 min.

Example 53

Preparation of the Acetate of cis-Cyclosporin Vinyl Iodide

Ethyl triphenylphosphonium iodide (203 mg, 0.49 mmol) was dissolved in THF (3 mL) and treated with n-BuLi (0.4 mL, 2.5 M in hexanes, 0.98 mmol) at room temperature under N$_2$ atmosphere. Reaction mixture was cooled to −78° C. and treated with a solution of I$_2$ (109 mg, 0.43 mmol) in THF (2 mL). Mixture was stirred for 5 min and then warmed to −15° C. for 5 min. Next, the reaction was treated with sodium bis(trimethylsilyl)amide (0.4 mL, 1 M in THF, 0.41 mmol) and stirred for an additional 5 min. Acetyl cyclosporin aldehyde from Example 2 (500 mg, 0.4 mmol) was added to the reaction, stirred at −15° C. for 10 min, and then allowed to warm to room temperature. Reaction was poured into a saturated solution of NH$_4$Cl and extracted with ether. Organic layer was washed with brine, dried over sodium sulfate, and concentrated in vacuo. The crude product was purified by semi-preparative HPLC to afford the acetate of the cis-cyclosporin vinyl iodide (13 mg, 2%) as an off-white solid: $^1$H NMR (300 MHz, CDCl$_3$) δ 8.56 (d, J=9.6 Hz, 1H), 8.04 (d, J=6.8 Hz, 1H), 7.65 (d, J=9.1 Hz, 1H), 7.49 (d, J=7.7 Hz, 1H), 5.68 (dd, J=10.9, 3.8 Hz, 1H), 5.57 (s, 1H), 5.52 (d, J=6.1 Hz, 2H), 5.38 (dd, J=11.8, 3.5 Hz, 1H), 5.28-5.13 (m, 8H), 5.02 (d, J=10.5 Hz, 3H), 4.84 (t, J=7.3 Hz, 2H), 4.77 (t, J=9.5 Hz, 2H), 4.64 (d, J=13.8 Hz, 2H), 4.42 (t, J=7.0 Hz, 2H), 3.44 (s, 3H), 3.27 (s, 3H), 3.24 (s, 3H), 3.20 (s, 3H), 3.11 (s, 3H), 2.67 (s, 3H), 2.66 (s, 3H), 2.46 (s, 3H), 2.05 (s, 2H), 1.32 (d, J=7.1 Hz, 4H), 1.27 (d, J=7.1 Hz, 4H), 1.02-0.79 (m, 52H); ESI MS m/z 1371 [C$_{64}$H$_{112}$IN$_{11}$O$_{13}$+H]$^+$.

Example 54

Preparation of cis-Cyclosporin Vinyl Iodide

A solution of the acetate of cis-cyclosporin vinyl iodide from Example 53 (13 mg, 0.009 mmol) in methanol (1 mL) was stirred at room temperature. Reaction mixture was treated with potassium carbonate (15 mg, 0.11 mmol) and was allowed to keep stirring under N$_2$ atmosphere overnight. Mixture was diluted with ethyl acetate, washed with saturated sodium bicarbonate solution and brine, dried over sodium sulfate, and concentrated in vacuo. The crude product was purified by semi-preparative HPLC to afford cis-cyclosporin vinyl iodide (6 mg, 47%) as a white solid: $^1$H NMR (300 MHz, CDCl$_3$) δ 7.93 (d, J=9.8 Hz, 1H), 7.61 (d, J=7.2 Hz, 1H), 7.44 (d, J=8.3 Hz, 1H), 7.22 (d, J=8.0 Hz, 1H), 5.68 (dd, J=11.0, 4.2 Hz, 1H), 5.45 (d, J=6.7 Hz, 2H), 5.39-5.33 (m, 4H), 5.13-4.96 (m, 11H), 4.81 (t, J=7.5 Hz, 2H), 4.74-4.63 (m, 6H), 4.50 (t, J=7.2 Hz, 2H), 3.51 (s, 3H), 3.39 (s, 3H), 3.24 (s, 3H), 3.11 (s, 6H), 2.69 (s, 6H), 2.48 (s, 2H), 1.35 (d, J=7.2 Hz, 2H), 1.27-1.24 (m, 4H), 1.08-0.83 (m, 48H), 0.79 (d, J=6.6 Hz, 1H); ESI MS m/z 1329 [C$_{62}$H$_{110}$IN$_{11}$O$_{12}$+H]$^+$; HPLC>99% (AUC), t$_R$=21.02 min.

Example 55

Preparation of the Acetate of Cyclosporin Oxime

Methoxyamine hydrochloride (4.3 mg, 0.052 mmol) was added to a solution of the acetate of cyclosporin α,β-unsaturated aldehyde from Example 24 (65 mg, 0.052 mmol) in pyridine (1 mL) at room temperature. The mixture was stirred under nitrogen for 1 h and then diluted with ether, washed with 0.2 N HCl and brine, dried over sodium sulfate, filtered, and concentrated in vacuo. The residue was purified by semi-preparative HPLC to afford the desired acetate of cyclosporin oxime (31 mg, 47%) as a white solid and a mixture of two isomers: $^1$H NMR (300 MHz, CDCl$_3$) δ 8.54 (d, J=9.5 Hz, 1H), 8.04 (d, J=6.8 Hz, 1H), 7.70 (d, J=9.8 Hz, 2H), 7.51 (d, J=7.5 Hz, 1H), 6.51 (dd, J=15.5, 9.0 Hz, 1H), 6.00 (dd, J=15.5, 9.5 Hz, 1H), 5.70-4.41 (m, 12H), 3.86 (s, 3H), 3.45 (s, 3H), 3.25 (s, 3H), 3.22 (s, 3H), 3.20 (s, 3H), 3.11 (s, 3H), 2.68 (s, 3H), 2.66 (s, 3H), 2.50-1.50 (m, 10H), 2.02 (s, 3H), 1.40-0.82 (m, 58H); ESI MS m/z 1288 [C$_{65}$H$_{114}$N$_{12}$O$_{14}$+H]$^+$.

Example 56

Preparation of Cyclosporin Oxime

A mixture of the acetate of cyclosporin oxime from Example 55 (24 mg, 0.019 mmol), potassium carbonate (30 mg, 0.22 mmol) and methanol (1 mL) was stirred at room temperature overnight, and then diluted with ethyl acetate, washed with water and brine, dried over sodium sulfate, filtered, and concentrated in vacuo. The residue was dissolved in methylene chloride and filtered through a microfilter (0.2 μm), and the filtrate was concentrated and dried under vacuum to afford cyclosporin oxime (21 mg, 90%) as a white solid: $^1$H NMR (300 MHz, CDCl$_3$) δ 8.04 (d, J=9.5 Hz, 1H), 7.71 (d, J=9.5 Hz, 1H), 7.65 (d, J=7.5 Hz, 1H), 7.49 (d, J=8.5 Hz, 1H), 7.16 (d, J=7.8 Hz, 1H), 6.07 (dd, J=15.5, 9.5 Hz, 1H), 5.93 (ddd, J=15.4, 8.0, 6.0 Hz, 1H), 5.72-3.82 (m, 12H), 3.85 (s, 3H), 3.51 (s, 3H), 3.40 (s, 3H), 3.26 (s, 3H), 3.12 (s, 3H), 3.11 (s, 3H), 2.69 (s, 3H), 2.68 (s, 3H), 2.50-1.50 (m, 11H), 1.40-0.82 (m, 58H); ESI MS m/z 1246 $[C_{63}H_{112}N_{12}O_{13}+H]^+$; HPLC>99% (AUC), $t_R$=13.31 min.

Example 57

Preparation of the Acetate of Cyclosporin Oxime

O-Ethylhydroxylamine hydrochloride (3.1 mg, 0.032 mmol) was added to a solution of the acetate of cyclosporin α,β-unsaturated aldehyde from Example 24 (40 mg, 0.032 mmol) in pyridine (0.5 mL) at room temperature. The mixture was stirred under nitrogen for 1 h and then diluted with ethyl acetate, washed with 1 N HCl and brine, dried over sodium sulfate, filtered, and concentrated in vacuo. The residue was purified by semi-preparative HPLC to afford the acetate of the desired cyclosporin oxime (8 mg, 20%) as a white solid and a mixture of two isomers: $^1$H NMR (300 MHz, CDCl$_3$) δ 8.53 (d, J=9.5 Hz, 1H), 8.05 (d, J=6.8 Hz, 1H), 7.72 (d, J=9.8 Hz, 1H), 7.69 (d, J=9.8 Hz, 1H), 7.58 (d, J=7.5 Hz, 1H), 6.53 (dd, J=15.5, 9.0 Hz, 1H), 6.04 (dd, J=15.5, 9.1 Hz, 1H), 5.75-4.10 (m, 14H), 3.44 (s, 3H), 3.25 (s, 3H), 3.21 (s, 3H), 3.20 (s, 3H), 3.12 (s, 3H), 2.68 (s, 3H), 2.67 (s, 3H), 2.50-1.50 (m, 10H), 2.02 (s, 3H), 1.40-0.82 (m, 611H); ESI MS m/z 1302 $[C_{66}H_{116}N_{12}O_{14}+H]^+$.

Example 58

Preparation of Cyclosporin Oxime

A mixture of the acetate of cyclosporin oxime from Example 57 (8 mg, 0.006 mmol), potassium carbonate (30 mg, 0.22 mmol) and methanol (1 mL) was stirred at room temperature for 4 h, and then diluted with ethyl acetate, washed with water and brine, dried over sodium sulfate, filtered, and concentrated in vacuo. The residue was dissolved in methylene chloride and filtered through a microfilter (0.2 μm), and the filtrate was concentrated and dried under vacuum to afford cyclosporin oxime (7 mg, 88%) as a white solid: $^1$H NMR (500 MHz, CDCl$_3$) δ 8.04 (d, J=9.5 Hz, 1H), 7.72 (d, J=9.5 Hz, 1H), 7.63 (d, J=7.5 Hz, 1H), 7.49 (d, J=8.5 Hz, 1H), 7.16 (d, J=8.0 Hz, 1H), 6.07 (dd, J=15.5, 9.5 Hz, 1H), 5.92 (ddd, J=15.5, 8.5, 6.5 Hz, 1H), 5.71-3.82 (m, 14H), 3.51 (s, 3H), 3.40 (s, 3H), 3.26 (s, 3H), 3.11 (s, 3H), 3.11 (s, 3H), 2.69 (s, 3H), 2.68 (s, 3H), 2.50-1.50 (m, 11H), 1.40-0.82 (m, 61H); ESI MS m/z 1260 $[C_{64}H_{114}N_{12}O_{13}+H]^+$; HPLC 95.0% (AUC), $t_R$=16.91 min.

Example 59

Preparation of the Acetate of Cyclosporin Oxime

O-Benzylhydroxylamine hydrochloride (5.1 mg, 0.032 mmol) was added to a solution of the acetate of cyclosporin α,β-unsaturated aldehyde from Example 24 (40 mg, 0.032 mmol) in pyridine (0.5 mL) at room temperature. The mixture was stirred under nitrogen for 1 h and then diluted with ethyl acetate, washed with 1 N HCl and brine, dried over sodium sulfate, filtered, and concentrated in vacuo. The residue was purified by semi-preparative HPLC to afford the desired acetate of cyclosporin oxime (7 mg, 16%) as a white solid and a mixture of two isomers: $^1$H NMR (300 MHz, CDCl$_3$) δ 8.53 (d, J=9.5 Hz, 1H), 8.05 (d, J=6.8 Hz, 1H), 7.81 (d, J=9.3 Hz, 1H), 7.76 (d, J=9.9 Hz, 1H), 7.70-7.28 (m, 6H), 6.56 (dd, J=15.7, 9.4 Hz, 1H), 6.02 (dd, J=15.5, 10.2 Hz, 1H), 5.75-4.41 (m, 14H), 3.44 (s, 3H), 3.24 (s, 3H), 3.19 (s, 6H), 3.11 (s, 3H), 2.68 (s, 3H), 2.67 (s, 3H), 2.50-1.50 (m, 10H), 2.02 (s, 3H), 1.40-0.82 (m, 58H); ESI MS m/z 1364 $[C_{71}H_{118}N_{12}O_{14}+H]^+$.

Example 60

Preparation of Cyclosporin Oxime

A mixture of the acetate of cyclosporin oxime from Example 59 (7 mg, 0.005 mmol), potassium carbonate (30 mg, 0.22 mmol) and methanol (1 mL) was stirred at room temperature for 4 h, and then diluted with ethyl acetate, washed with water and brine, dried over sodium sulfate, filtered and concentrated in vacuo. The residue was dissolved in methylene chloride and filtered through a microfilter (0.2 μm), and the filtrate was concentrated and dried under vacuum to afford cyclosporin oxime (6 mg, 86%) as a white solid: $^1$H NMR (500 MHz, CDCl$_3$) δ 8.03 (d, J=9.5 Hz, 1H), 7.79 (d, J=10.0 Hz, 1H), 7.63 (d, J=7.5 Hz, 1H), 7.48 (d, J=8.0 Hz, 1H), 7.38-7.28 (m, 5H), 7.16 (d, J=8.0 Hz, 1H), 6.07 (dd, J=15.5, 10.0 Hz, 1H), 5.94 (ddd, J=15.5, 8.5, 6.5 Hz, 1H), 5.71-3.85 (m, 14H), 3.51 (s, 3H), 3.40 (s, 3H), 3.25 (s, 3H), 3.11 (s, 6H), 2.69 (s, 3H), 2.68 (s, 3H), 2.50-1.50 (m, 11H), 1.40-0.82 (m, 58H); ESI MS m/z 1322 $[C_{69}H_{116}N_{12}O_{13}+H]^+$; HPLC 97.5% (AUC), $t_R$=20.40 min.

Example 61

Preparation of the Acetate of Cyclosporin Hydrazone 1,1-Dimethylhydrazine (2.4 μL, 0.032 mmol) was added to a solution of the acetate of cyclosporin α,β-unsaturated aldehyde from Example 24 (40 mg, 0.032 mmol) in methanol (1 mL) at room temperature. The mixture was stirred under nitrogen for 2 h and then diluted with ethyl acetate, washed with brine, dried over sodium sulfate, filtered and concentrated in vacuo. The residue was purified by semi-preparative HPLC to afford the desired acetate of cyclosporin hydrazone (15 mg, 36%) as a white solid and a mixture of two isomers: $^1$H NMR (500 MHz, CDCl$_3$) δ 8.42 (d, J=9.5 Hz, 1H), 8.20 (d, J=9.5 Hz, 1H), 8.03 (d, J=7.0 Hz, 1H), 7.78 (d, J=9.0 Hz, 1H), 7.45 (d, J=7.5 Hz, 1H), 6.35 (dt, J=15.5, 8.0 Hz, 1H), 6.11 (dd, J=15.5, 9.5 Hz, 1H), 5.71-4.41 (m, 12H), 3.46 (s, 3H), 3.25 (s, 3H), 3.21 (s, 3H), 3.20 (s, 3H), 3.11 (s, 9H), 2.68 (s, 3H), 2.66 (s, 3H), 2.50-1.50 (m, 10H), 2.02 (s, 3H), 1.40-0.82 (m, 58H); ESI MS m/z 1301 $[C_{66}H_{117}N_{13}O_{13}+H]^+$.

Example 62

Preparation of Cyclosporin Hydrazone

A mixture of the acetate of cyclosporin hydrazone from Example 61 (15 mg, 0.011 mmol), potassium carbonate (40 mg, 0.29 mmol) and methanol (1 mL) was stirred at room temperature for 6 h, and then diluted with ethyl acetate, washed with water and brine, dried over sodium sulfate, filtered and concentrated in vacuo. The residue was dissolved in methylene chloride and filtered through a microfilter (0.2 μm), and the filtrate was concentrated and dried under vacuum to afford cyclosporin hydrazone (12 mg, 82%) as a white solid: $^1$H NMR (300 MHz, CDCl$_3$) δ 8.03 (d, J=9.8 Hz, 1H), 7.61 (d, J=7.4 Hz, 1H), 7.51 (d, J=8.3 Hz, 1H), 7.15 (d, J=7.9 Hz, 1H), 7.05 (d, J=8.9 Hz, 1H), 6.15 (dd, J=15.7, 8.9 Hz, 1H), 5.71-3.75 (m, 13H), 3.51 (s, 3H), 3.41 (s, 3H), 3.24 (s, 3H), 3.11 (s, 3H), 3.10 (s, 3H), 2.85 (s, 6H), 2.70 (s, 3H), 2.69 (s, 3H), 2.50-1.50 (m, 11H), 1.40-0.82 (m, 58H); ESI MS m/z 1259 $[C_{64}H_{115}N_{13}O_{12}+H]^+$.

Example 63

Preparation of Cyclosporin Diol

To a mechanically stirred solution of diisopropylamine (2.6 mL, 18 mmol) in THF (50 mL) at −78° C. was added dropwise n-butyllithium (6.6 mL, 2.5 M in hexane, 17 mmol), then the mixture was stirred for 0.5 h. A solution of cyclosporin A (1.0 g, 0.83 mmol) in THF (8 mL) was added, and then the mixture was stirred for 2 h at −78° C. Paraformaldehyde (8.0 g) was heated to 170° C. and the resulting formaldehyde gas was transferred into the reaction via a glass tube which was wrapped with cotton and aluminum foil over 2 h. After stirred another 1 h at −78° C., the reaction mixture was quenched with water (10 mL). The mixture was allowed to warm to room temperature, diluted with ethyl acetate (150 mL) and washed with water (2×50 mL). The organic layer was separated, dried over anhydrous sodium sulfate and concentrated under vacuum. The crude material was purified by semi-preparative HPLC to afford cyclosporin diol (0.45 g, 44%) as a white solid: $^1$H NMR (300 MHz, CDCl$_3$) δ 8.09 (d, J=9.9 Hz, 1H), 7.70 (d, J=7.4 Hz, 1H), 7.57 (d, J=8.2 Hz, 1H), 7.15 (overlapped with CHCl$_3$, 1H), 5.70 (dd, J=11.0, 4.0 Hz, 1H), 5.49 (d, J=6.4 Hz, 1H), 5.38-5.30 (m, 3H), 5.16-4.93 (m, 5H), 4.83 (t, J=7.2 Hz, 1H), 4.65 (t, J=9.5 Hz, 1H), 4.54 (t, J=7.2 Hz, 1H), 4.05 (d, J=6.8 Hz, 2H), 3.73 (t, J=6.3 Hz, 1H), 3.49 (s, 3H), 3.30 (s, 3H), 3.25 (s, 3H), 3.15 (s, 3H), 3.11 (s, 3H), 2.70 (s, 3H), 2.69 (s, 3H), 2.50-2.38 (m, 2H), 2.20-1.92 (m, 6H), 1.75-0.65 (m, 64H); ESI MS m/z 1233 $[C_{63}H_{113}N_{11}O_{13}+H]^+$.

Example 64

Preparation of Cyclosporin Diacetate

To a solution of cyclosporin diol from Example 63 (0.43 g, 0.35 mmol) in methylene chloride (5 mL) was added pyridine (0.57 mL, 7.0 mmol) followed by 4-(dimethylamino)pyridine (86 mg, 0.70 mmol) and acetic anhydride (1.0 mL, 10.5 mmol). The reaction mixture was stirred for 2 days at room temperature. The reaction was diluted with ethyl ether (150 mL), washed with a saturated solution of sodium bicarbonate (30 mL), 1N HCl solution (30 mL) and brine (30 mL). The organic layer was separated, dried over anhydrous sodium sulfate and concentrated under vacuum. The crude material was purified by semi-preparative HPLC to afford cyclosporin diacetate (0.23 g, 50%) as a white solid: $^1$H NMR (300 MHz, CDCl$_3$) δ 8.60 (d, J=9.8 Hz, 1H), 8.05 (d, J=6.6 Hz, 1H), 7.55 (d, J=7.8 Hz, 1H), 7.49 (d, J=9.3 Hz, 1H), 5.68 (dd, J=11.0, 4.0 Hz, 1H), 5.49 (s, 2H), 5.40-4.95 (m, 8H), 4.85 (t, J=7.5 Hz, 1H), 4.76 (t, J=9.3 Hz, 1H), 4.58-4.34 (m, 3H), 3.37 (s, 3H), 3.27 (s, 3H), 3.23 (s, 3H), 3.20 (s, 3H), 3.14 (s, 3H), 2.67 (s, 3H), 2.66 (s, 3H), 2.48-2.35 (m, 1H), 2.10 (s, 3H), 2.01 (s, 3H), 1.98-1.85 (m, 2H), 1.75-0.65 (m, 67H); ESI MS m/z 1317 $[C_{67}H_{117}N_{11}O_{15}+H]^+$.

Example 65

Preparation of Cyclosporin Aldehyde

Ozone was bubbled into a solution of cyclosporin diacetate from Example 64 (0.22 g, 0.17 mmol) in methylene chloride (10 mL) at −78° C. until a blue color was developed. The mixture was degassed with nitrogen for a few min and dimethylsulfide (0.4 mL) was added at −78° C. The reaction mixture was allowed to warm to room temperature and stirred for 3 h. The reaction mixture was concentrated in vacuo and the residue was dissolved in ethyl acetate (120 mL), washed with water (2×20 mL) and brine (30 mL), dried over sodium sulfate, filtered, and concentrated in vacuo to afford cyclosporin aldehyde (0.19 g, 86%) as a white solid. The crude was carried to the next step without further purification: $^1$H NMR (300 MHz, CDCl$_3$) δ 9.55 (d, J=3.4 Hz, 1 H), 8.60 (d, J=9.9 Hz, 1H), 7.96 (d, J=7.1 Hz, 1H), 7.53 (d, J=7.7 Hz, 1H), 7.33 (d, J=9.1 Hz, 1H), 5.68 (dd, J=11.0, 4.0 Hz, 1H), 5.53 (d, J=11.2 Hz, 1H), 5.47 (d, J=11.2 Hz, 1H), 5.30 (dd, J=12.3, 3.6 Hz, 1H), 5.18-4.92 (m, 5H), 4.84 (t, J=6.9 Hz, 1H), 4.72 (t, J=9.6 Hz, 1H), 4.55-4.35 (m, 3H), 3.39 (s, 3H), 3.30 (s, 3H), 3.29 (s, 3H), 3.21 (s, 3H), 3.12 (s, 3H), 2.66 (s, 3H), 2.65 (s, 3H), 2.48-2.30 (m, 3H), 2.10 (s, 3H), 1.99 (s, 3H), 1.80-0.75 (m, 64H); ESI MS m/z 1305 $[C_{65}H_{113}N_{11}O_{16}+H]^+$.

Example 66

Preparation of the Diacetate of trans-Cyclosporin Diene

To a suspension of bis(cyclopentadienyl)zirconiumchloride hydride (199 mg, 0.77 mmol) in methylene chloride (2 mL) was added propargyltrimethylsilane (0.12 mL, 0.81 mmol), and then the mixture was stirred at room temperature for 10 min. To this solution was sequentially added a solution of cyclosporin aldehyde from Example 65 (100 mg, 0.077 mmol) in methylene chloride (1 mL) and then silver perchlorate (3 mg, 0.015 mmol). The resulting mixture was stirred at room temperature for 12 h, and then poured into a saturated solution of sodium bicarbonate (10 mL). The organic layer was separated and the aqueous layer was extracted with methylene chloride (2×20 mL). The combined organics were dried over anhydrous sodium sulfate and concentrated under vacuum to afford the crude product. The material was purified by semi-preparative HPLC to afford the diacetate of trans-cyclosporin diene (47 mg, 46%) as a white solid: $^1$H NMR (300 MHz, CDCl$_3$) δ 8.61 (d, J=9.5 Hz, 1H), 8.06 (d, J=6.8 Hz, 1H), 7.62 (d, J=9.2 Hz, 1H), 7.49 (d, J=7.7 Hz, 1H), 6.22 (dt, J=16.9, 10.2 Hz, 1H), 5.88 (dd, J=15.0, 10.5 Hz, 1H), 5.68 (dd, J=11.0, 4.0 Hz, 1H), 5.50 (s, 2H), 5.40-4.95 (m, 8H), 4.85 (t, J=7.5 Hz, 1H), 4.77 (t, J=9.3 Hz, 1H), 4.58-4.34 (m, 3H), 3.37 (s, 3H), 3.26 (s, 3H), 3.21 (s, 3H), 3.19 (s, 3H), 3.14 (s, 3H), 2.68 (s, 6H), 2.48-2.35 (m, 1H), 2.10 (s, 3H), 2.02 (s, 3H), 1.80-1.65 (m, 5H), 1.50-0.80 (m, 62H); ESI MS m/z 1329 $[C_{68}H_{117}N_{11}O_{15}+H]^+$.

Example 67

Preparation of trans-Cyclosporin Diene

To a stirred solution of the diacetate of trans-cyclosporin diene from Example 66 (45 mg, 0.034 mmol) in methanol (2 mL) was added potassium carbonate (140 mg, 1.02 mmol) at room temperature. After 12 h at room temperature, the reaction mixture was diluted with ethyl acetate (100 mL) and washed with water (20 mL). The aqueous layer was separated and extracted with ethyl acetate (30 mL). The combined organics were dried over anhydrous sodium sulfate, and concentrated under vacuum to afford the crude product. The material was purified by semi-preparative HPLC to afford trans-cyclosporin diene (11 mg, 26%) as a white solid: $^1$H NMR (300 MHz, CDCl$_3$) δ 8.07 (d, J=9.8 Hz, 1H), 7.66 (d, J=7.5 Hz, 1H), 7.52 (d, J=8.2 Hz, 1H), 7.18 (d, J=7.8 Hz, 1H), 6.29 (dt, J=16.9, 10.3 Hz, 1H), 5.98 (dd, J=15.0, 10.5 Hz, 1H), 5.69 (dd, J=11.0, 4.0 Hz, 1H), 5.65-5.55 (m, 1H), 5.51 (d, J=6.2 Hz, 1H), 5.30 (dd, J=11.6, 3.7 Hz, 1H), 5.15-4.93 (m 7H), 4.82 (t, J=7.5 Hz, 1H), 4.64 (t, J=9.4 Hz, 1H), 4.54 (t, J=7.4 Hz, 1H), 4.04 (d, J=6.7 Hz, 2H), 3.74 (t, J=6.9 Hz, 1H), 3.51 (s, 3H), 3.30 (s, 3H), 3.26 (s, 3H), 3.15 (s, 3H), 3.11 (s, 3H), 2.70 (s, 3H), 2.69 (s, 3H), 2.55-2.38 (m, 2H), 2.20-1.95 (m, 5H), 1.80-1.60 (m, 5H), 1.50-0.70 (m, 57H); ESI MS m/z 1245 $[C_{64}H_{113}N_{11}O_{13}+H]^+$; HPLC>99% (AUC), $t_R$=14.05 min.

Example 68

Preparation of the Acetate of trans-Cyclosporin Diene-$d_2$

To a suspension of bis(cyclopentadienyl)zirconiumchloride hydride (199 mg, 0.77 mmol) in methylene chloride (2 mL) was added $d_2$-propargyltrimethylsilane (92 mg, 0.81 mmol), and then the mixture was stirred at room temperature for 10 min. To this solution was sequentially added a solution of cyclosporin aldehyde from Example 65 (100 mg, 0.077 mmol) in methylene chloride (1 mL) and then silver perchlorate (3 mg, 0.015 mmol). The resulting mixture was stirred at room temperature for 12 h, and then poured into a saturated solution of sodium bicarbonate (10 mL). The organic layer was separated and the aqueous layer was extracted with methylene chloride (2×20 mL). The combined organics were dried over anhydrous sodium sulfate and concentrated under vacuum to afford the crude product. The material was purified by semi-preparative HPLC to afford the acetate of deuterated trans-cyclosporin diene (20 mg, 20%) as a white solid: $^1$H NMR (300 MHz, CDCl$_3$) δ 8.61 (d, J=9.5 Hz, 1H), 8.05 (d, J=6.8 Hz, 1H), 7.65-7.58 (m, 2H), 6.20 (d, J=10.5 Hz, 1H), 5.88 (dd, J=15.0, 10.5 Hz, 1H), 5.69 (d, J=7.5 Hz, 1H), 5.50 (s, 2H), 5.40-4.70 (m, 10H), 4.55-4.35 (m, 4H), 3.37 (s, 3H), 3.26 (s, 3H), 3.21 (s, 3H), 3.19 (s, 3H), 3.14 (s, 3H), 2.68 (s, 6H), 2.48-2.35 (m, 1H), 2.10 (s, 3H), 2.02 (s, 3H), 1.80-1.65 (m, 5H), 1.50-0.80 (m, 59H); ESI MS m/z 1331 $[C_{68}H_{115}D_2N_{11}O_{15}+H]^+$.

Example 69

Preparation of trans-Cyclosporin Diene-$d_2$

To a stirred solution of the acetate of deuterated trans-cyclosporin diene from Example 68 (17 mg, 0.013 mmol) in methanol (3 mL) was added potassium carbonate (54 mg, 0.39 mmol) at room temperature. After 12 h at room temperature, the reaction mixture was diluted with ethyl acetate (100 mL) and washed with water (20 mL). The aqueous layer was separated and extracted with ethyl acetate (30 mL). The combined organics were dried over anhydrous sodium sulfate, and concentrated under vacuum to afford crude product. The material was purified by semi-preparative HPLC to afford trans-cyclosporin diene-$d_2$ (5 mg, 31%) as a white solid: $^1$H NMR (300 MHz, CDCl$_3$) δ 8.06 (d, J=9.7 Hz, 1H), 7.66 (d, J=7.4 Hz, 1H), 7.48 (d, J=8.3 Hz, 1H), 7.16 (d, J=7.9 Hz, 1H), 6.29 (d, J=10.3 Hz, 1H), 5.98 (dd, J=15.0, 10.5 Hz, 1H), 5.69 (dd, J=11.0, 4.0 Hz, 1H), 5.65-5.55 (m, 1H), 5.51 (d, J=6.2 Hz, 1H), 5.30 (dd, J=11.6, 3.7 Hz, 1H), 5.15-4.75 (m, 8H), 4.65 (t, J=9.4 Hz, 1H), 4.53 (t, J=7.4 Hz, 1H), 4.04 (d, J=6.7 Hz, 2H), 3.75 (t, J=6.9 Hz, 1H), 3.51 (s, 3H), 3.31 (s, 3H), 3.26 (s, 3H), 3.15 (s, 3H), 3.11 (s, 3H), 2.70 (s, 3H), 2.68 (s, 3H), 2.55-2.30 (m, 2H), 2.20-1.60 (m, 10H), 1.50-0.70 (m, 55H); ESI MS m/z 1247 $[C_{64}H_{111}D_2N_{11}O_{13}+H]^+$; HPLC 96.7% (AUC), $t_R$=13.76 min.

Example 70

Preparation of the Acetate of Cyclosporin Vinyl Chloride

Anhydrous CrCl$_2$ (119 mg, 0.97 mmol) was added to a solution of cyclosporin aldehyde from Example 65 (126 mg, 0.097 mmol) and CHCl$_3$ (30 mg, 0.25 mmol) in THF (4 mL) under argon atmosphere. The mixture was stirred at 40° C. under argon for 24 h, and then cooled down to room temperature, and filtered through a short silica gel column (EtOAc). The combined filtration was washed with water (3×10 mL) and brine (3×10 mL), dried over Na$_2$SO$_4$, and concentrated to dryness. The residue was purified by semi-preparative HPLC to give the acetate of cyclosporin vinyl chloride (71 mg, 55%) as a white solid: $^1$H NMR (CDCl$_3$, 300 MHz) δ 8.57 (d, J=9.7 Hz, 1H), 8.00 (d, J=6.6 Hz, 1H), 7.71 (d, J=7.5 Hz, 1H), 7.63 (d, J=9.0 Hz, 1H), 5.82-5.71 (m, 2H), 5.68 (dd, J=11.0, 4.2 Hz, 1H), 5.48 (d, J=6.8 Hz, 1H), 5.43 (dd, J=11.7, 3.8 Hz, 1H), 5.27 (dd, J=12.0, 3.9 Hz, 1H), 5.17 (t, J=7.5 Hz, 1H), 5.08-4.95 (m, 5H), 4.85 (t, J=7.2 Hz, 1H), 4.78 (t, J=9.6 Hz, 1H), 4.55-4.35 (m, 3H), 3.25 (s, 3H), 3.27 (s, 3H), 3.24 (s, 3H), 3.19 (s, 3H), 3.15 (s, 3H), 2.68 (s, 6H), 2.41-2.37 (m, 2H), 2.14-1.99 (m, 12H), 1.72-0.75 (m, 58H); ESI MS m/z 1337 $[C_{66}H_{114}ClN_{11}O_{15}+H]^+$.

Example 71

Preparation of Cyclosporin Vinyl Chloride

The acetate of cyclosporin vinyl chloride from Example 70 (71 mg, 0.053 mmol) was dissolved in MeOH (7 mL), and then K$_2$CO$_3$ (200 mg, 1.449 mmol) was added. The mixture was stirred at room temperature under N$_2$ for 6 h, and then diluted with EtOAc (200 mL), washed with brine (3×10 mL), dried over Na$_2$SO$_4$, and concentrated to dryness. The residue was purified by semi-preparative HPLC to give cyclosporin vinyl chloride (35 mg, 53%) as a white solid: $^1$H NMR (CDCl$_3$, 500 MHz) δ 8.08 (d, J=9.9 Hz, 1H), 7.69 (d, J=7.3 Hz, 1H), 7.50 (d, J=8.3 Hz, 1H), 7.26 (d, J=8.9 Hz, 1H), 5.92-5.84 (m, 2H), 5.70 (dd, J=11.0, 4.2 Hz, 1H), 5.48 (d, J=6.8 Hz, 1H), 5.33 (dd, J=11.7, 3.8 Hz, 1H), 5.10-4.95 (m, 5H), 4.83 (t, J=7.3 Hz, 1H), 4.65 (t, J=9.0 Hz, 1H), 4.50 (t, J=7.3 Hz, 1H), 4.04 (d, J=6.7 Hz, 2H), 3.80 (t, J=6.5 Hz, 1H), 3.50 (s, 3H), 3.31 (s, 3H), 3.27 (s, 3H), 3.15 (s, 3H), 3.12 (s, 3H), 2.69 (s, 3H), 2.68 (s, 3H), 2.41-2.37 (m, 2H), 2.14-1.99 (m, 6H), 1.78-1.64 (m, 7H), 1.34-0.80 (m, 54H); ESI MS m/z 1253 $[C_{62}H_{110}ClN_{11}O_{13}+H]^+$; HPLC>99% (AUC), $t_R$=14.0 min.

Example 72

Preparation of Cyclosporin Vinyl Iodide

To an ice-cooled solution of cyclosporin aldehyde from Example 65 (200 mg, 0.15 mmol) in THF (5 mL) was added anhydrous CrCl$_2$ (184 mg, 1.5 mmol) and CHI$_3$ (206 mg, 0.6 mmol), and then the mixture was stirred at 0° C. under N$_2$ for 24 h. The reaction mixture was diluted with EtOAc (200 mL), washed with water (4×10 mL), dried over MgSO$_4$, and concentrated to dryness. The residue was purified by semi-preparative HPLC to give the diacetate of cyclosporin vinyl iodide (57 mg, 26%) as a pale yellow oil: ESI MS m/z 1429 $[C_{66}H_{114}IN_{11}O_{15}+H]^+$.

The above diacetate of cyclosporine vinyl iodide (57 mg, 0.04 mmol) was dissolved in MeOH (10 mL), and then K$_2$CO$_3$ (200 mg, 1.45 mmol) was added. The mixture was stirred at room temperature under $N_2$ overnight, and then diluted with EtOAc (200 mL), washed with brine (3×10 mL), dried over $Na_2SO_4$, and concentrated to dryness. The residue was purified by semi-preparative HPLC to give cyclosporin vinyl iodide (19 mg, 35%) as a white solid: $^1$H NMR (CDCl$_3$, 500 MHz) δ 8.05 (d, J=9.8 Hz, 1H), 7.68 (d, J=7.4 Hz, 1H), 7.48 (d, J=9.1 Hz, 1H), 7.22 (d, J=7.8 Hz, 1H), 6.49 (ddd, J=14.5, 8.5, 6.3 Hz, 1H), 5.91 (d, J=14.3 Hz, 1H), 5.70 (dd, J=10.9, 4.0 Hz, 1H), 5.49 (d, J=6.6 Hz, 1H), 5.31 (dd, J=12.7, 3.8 Hz, 1H), 5.09-5.04 (m, 4H), 4.98-4.94 (m, 2H), 4.84 (t, J=7.2 Hz, 1H), 4.65 (dd, J=9.6, 8.5 Hz, 1H), 4.53 (t, J=7.3 Hz, 1H), 4.04 (d, J=6.7 Hz, 1H), 3.76 (t, J=6.5 Hz, 1H), 3.50 (s, 3H), 3.30 (s, 3H), 3.27 (s, 3H), 3.15 (s, 3H), 3.11 (s, 3H), 2.69 (s, 3H), 2.68 (s, 3H), 2.45-2.40 (m, 2H), 1.78-1.64 (m, 7H), 1.43-0.76 (m, 60H); ESI MS m/z 1344 [$C_{62}H_{110}IN_{11}O_{13}$+H]$^+$; HPLC 95.6% (AUC), $t_R$=14.1 min.

Example 73

Preparation of the Acetates of cis- and trans-Cyclosporin Vinyl Bromide

To a suspension of (bromomethyl)triphenylphosphonium bromide (700 mg, 1.6 mmol) in THF (5 mL) at −78° C. was added dropwise sodium bis(trimethylsilyl)amide (1.6 mL, 1 M in THF, 1.6 mmol), then the mixture was stirred for 1 h. A solution of cyclosporin aldehyde from Example 65 (0.21 g, 0.16 mmol) in THF (5 mL) was added, and then the mixture was stirred for 2 h at −78° C. The reaction mixture was quenched with a saturated solution of ammonium chloride. After warmed to room temperature, the mixture was diluted with ethyl ether (100 mL), washed with brine (30 mL), dried over anhydrous sodium sulfate and concentrated under vacuum. The crude material was purified by semi-preparative HPLC to afford the acetate of cis-cyclosporin vinyl bromide (50 mg, 23%): $^1$H NMR (CDCl$_3$, 300 MHz) δ 8.62 (d, J=9.7 Hz, 1H), 8.01 (d, J=6.6 Hz, 1H), 7.60 (d, J=7.8 Hz, 1H), 7.54 (d, J=9.0 Hz, 1H), 6.04 (d, J=7.7 Hz, 1H), 6.02-5.92 (m, 1H), 5.69 (dd, J=10.8, 3.9 Hz, 1H), 5.50 (dd, J=16.5, 11.5 Hz, 2H), 5.24 (dd, J=12.2, 3.7 Hz, 2H), 5.15 (dd, J=7.5, 6.0 Hz, 1H), 5.10-4.93 (m, 3H), 4.95 (t, J=7.5 Hz, 1H), 4.73 (t, J=9.6 Hz, 1H), 4.55-4.38 (m, 4H), 3.37 (s, 3H), 3.29 (s, 3H), 3.23 (s, 3H), 3.19 (s, 3H), 3.14 (s, 3H), 2.67 (s, 3H), 2.66 (s, 3H), 2.45-2.35 (m, 1H), 2.20-2.15 (m, 2H), 2.10 (s, 3H), 2.04 (s, 3H), 2.00-1.82 (m, 3H), 1.80-1.60 (m, 3H), 1.48-0.82 (m, 57H); ESI MS m/z 1381 [$C_{66}H_{114}BrN_{11}O_{15}$+H]$^+$; and the acetate of trans-cyclosporin vinyl bromide (8 mg, 4%): $^1$H NMR (CDCl$_3$, 300 MHz) δ 8.54 (d, J=9.9 Hz, 1H), 7.99 (d, J=6.9 Hz, 1H), 7.56 (d, J=7.8 Hz, 1H), 7.38 (d, J=9.2 Hz, 1H), 6.15-5.92 (m, 1H), 5.85 (d, J=13.8 Hz, 1H), 5.72-5.65 (m, 1H), 5.54-5.43 (m, 2H), 5.38 (dd, J=11.7, 3.9 Hz, 1H), 5.78-5.69 (m, 1H), 5.15 (t, J=5.7 Hz, 1H), 5.04-4.70 (m, 5H), 4.54-4.30 (m, 2H), 4.04 (t, J=4.0 Hz, 1H), 3.35 (s, 3H), 3.28 (s, 3H), 3.26 (s, 3H), 3.20 (s, 3H), 3.14 (s, 3H), 2.67 (s, 3H), 2.66 (s, 3H), 2.42-2.33 (m, 1H), 2.25-2.12 (m, 2H), 2.10 (s, 3H), 2.02 (s, 3H), 1.90-1.62 (m, 6H), 1.45-0.85 (m, 58H); ESI MS m/z 1381 [$C_{66}H_{114}BrN_{11}O_{15}$+H]$^+$.

Example 74

Preparation of cis-Cyclosporin Vinyl Bromide

To a stirred solution of the acetate of cis-cyclosporin vinyl bromide from Example 73 (24 mg, 0.017 mmol) in methanol (3 mL) was added potassium carbonate (120 mg, 0.86 mmol) at room temperature. After 12 h at room temperature, the reaction mixture was quenched with a saturated solution of ammonium chloride (20 mL), and then extracted with ethyl acetate (3×30 mL). The combined organics were dried over anhydrous sodium sulfate and concentrated under vacuum to afford the crude product. The material was purified by semi-preparative HPLC to afford cis-cyclosporin vinyl bromide (8 mg, 36%) as a white solid: $^1$H NMR (300 MHz, CDCl$_3$) δ 8.15 (d, J=9.9 Hz, 1H), 7.74 (d, J=7.2 Hz, 1H), 7.62 (d, J=8.1 Hz, 1H), 7.39 (d, J=8.0 Hz, 1H), 6.14-6.02 (m, 2H), 5.69 (dd, J=11.1, 3.9 Hz, 1H), 5.43 (d, J=7.2 Hz, 1H), 5.30 (dd, J=11.4, 3.6 Hz, 1H), 5.15-5.38 (m, 6H), 4.83 (t, J=6.9 Hz, 1H), 4.66 (t, J=9.0 Hz, 1H), 4.52 (t, J=7.2 Hz, 1H), 4.05 (d, J=6.6 Hz, 2H), 3.90 (t, J=6.6 Hz, 1H), 3.50 (s, 3H), 3.31 (s, 3H), 3.25 (s, 3H), 3.15 (s, 3H), 3.12 (s, 3H), 2.70 (s, 3H), 2.69 (s, 3H), 2.43-1.90 (m, 8H), 1.80-1.57 (m, 5H), 1.45-0.75 (m, 55H); ESI MS m/z 1297 [$C_{62}H_{110}BrN_{11}O_{13}$+H]$^+$; HPLC 97.0% (AUC), $t_R$=13.95 min.

Example 75

Preparation of trans-Cyclosporin Vinyl Bromide

To a stirred solution of the acetate of trans-cyclosporin vinyl bromide from Example 73 (10 mg, 0.007 mmol) in methanol (2 mL) was added potassium carbonate (50 mg, 0.36 mmol) at room temperature. After 12 h at room temperature, the reaction mixture was quenched with a saturated solution of ammonium chloride (15 mL), and then extracted with ethyl acetate (3×30 mL). The combined organics were dried over anhydrous sodium sulfate and concentrated under vacuum to afford the crude product. The material was purified by semi-preparative HPLC to afford trans-cyclosporin vinyl bromide (4 mg, 44%) as a white solid: $^1$H NMR (300 MHz, CDCl$_3$) δ 8.08 (d, J=9.9 Hz, 1H), 7.71 (d, J=7.2 Hz, 1H), 7.56 (d, J=8.1 Hz, 1H), 7.31 (d, J=8.0 Hz, 1H), 6.20-6.05 (m, 1H), 5.94 (d, J=13.4 Hz, 1H), 5.70 (dd, J=10.8, 3.6 Hz, 1H), 5.49 (d, J=6.6 Hz, 1H), 5.34 (dd, J=11.4, 3.6 Hz, 1H), 5.12-4.95 (m, 6H), 4.83 (t, J=6.9 Hz, 1H), 4.66 (t, J=9.0 Hz, 1H), 4.51 (t, J=7.2 Hz, 1H), 4.05 (d, J=6.6 Hz, 2H), 3.78 (t, J=6.0 Hz, 1H), 3.50 (s, 3H), 3.30 (s, 3H), 3.26 (s, 3H), 3.15 (s, 3H), 3.11 (s, 3H), 2.70 (s, 3H), 2.69 (s, 3H), 2.42-2.33 (m, 2H), 2.20-1.89 (m, 6H), 1.80-1.60 (m, 5H), 1.45-0.75 (m, 55H); ESI MS m/z 1297 [$C_{62}H_{110}BrN_{11}O_{13}$+H]$^+$; HPLC 97.0% (AUC), $t_R$=13.74 min.

Example 76

Preparation of Arylated Cyclosporin Diol

To a stirred solution of cyclosporin diol from Example 63 (57 mg, 0.040 mmol) in methylene chloride was added styrene (42 mg, 0.400 mmol) and Grubbs' catalyst $2^{nd}$ generation (2.5 mg, 0.004 mmol). The resulting mixture was stirred overnight while refluxing at 50° C. in a nitrogen atmosphere. The reaction was then cooled to 25° C. and concentrated to dryness. The crude mixture was purified by semi-preparative HPLC twice to afford the desired product (8.8 mg, 17%) as a white solid: $^1$H NMR (300 MHz, CDCl$_3$); δ 8.09 (d, J=9.9 Hz, 1H), 7.70 (d, J=7.7 Hz, 1H), 7.60-7.08 (m, 6H), 6.98-6.90 (m, 1H), 6.33 (d, J=15.7 Hz, 1H), 6.20-6.12 (m, 1H), 5.69 (dd, J=10.8, 4.0 Hz, 1H), 5.58 (d, J=5.6 Hz, 1H), 5.32 (dd, J=11.6, 3.6 Hz, 1H), 5.14-4.91 (m, 5H), 4.82 (t, J=7.1 Hz, 1H), 4.68-4.50 (m, 2H), 4.04 (d, J=6.8 Hz, 2H), 3.72 (t, J=6.0 Hz, 1H), 3.53 (s, 3H), 3.31 (s, 3H), 3.27 (s, 3H), 3.16 (s, 3H), 3.10 (s, 3H), 2.71 (s, 3H), 2.68 (s, 3H), 2.45-2.35 (m, 1H), 2.15-1.90 (m, 5H), 1.78-1.52 (m, 7H), 1.48-0.65 (m, 56H); ESI MS m/z 1295 [$C_{68}H_{115}N_{11}O_{13}$+H]$^+$; HPLC 93.8% (AUC), $t_R$=14.26 min.

Example 77

Preparation of Cyclosporin Fluoride

A flask charged with a solution of cyclosporin diol from Example 63 (50 mg, 0.410 mmol) in methylene chloride (2 mL) was cooled to −78° C. Allyl Fluoride (1.5 g, 90.11 mmol) was bubbled through the solution. The reaction was allowed to warm to room temperature and Grubbs' catalyst $2^{nd}$ generation (18 mg, 0.021 mmol) was added. The resulting mixture was stirred overnight while refluxing at 50° C. in an atmosphere of allyl fluoride (via attached balloon). After 16 h, the reaction was concentrated to dryness under reduced pressure. Purification by semi-preparative HPLC yielded 11.3 mg (22%) of the cyclosporin fluoride as an off-white solid: $^1$H NMR (500 MHz, CDCl$_3$) 8.11 (d, J=9.5 Hz, 1H), 7.69 (d, J=7.5 Hz, 1H), 7.59 (d, J=8.0 Hz, 1H), 7.25 (overlapped with CHCl$_3$, 1H), 5.79-5.57 (m, 3H), 5.51 (d, J=6.5 Hz, 1H), 5.29 (dd, J=12.0, 4.0 Hz, 1H), 5.12-4.94 (m, 5H), 4.87-4.79 (m, 2H), 4.72 (d, J=6.0 Hz, 1H), 4.64 (t, J=8.5 Hz, 1H), 4.55 (t, J=7.5 Hz, 1H), 4.04 (d, J=6.5 Hz, 2H), 3.75 (t, J=7.0 Hz, 1H), 3.50 (s, 3H), 3.23 (s, 3H), 3.26 (s, 3H), 3.15 (s, 3H), 3.11 (s, 3H), 2.70 (s, 3H), 2.69 (s, 3H), 2.53-2.37 (m, 2H), 2.18-1.9 (m, 6H), 1.82-1.60 (m, 7H), 1.52-0.70 (m, 54H); ESI MS m/z 1291 $[C_{63}H_{112}FN_{11}O_{13}+H]^+$; HPLC 98.3% (AUC), $t_R$=13.42 min.

Example 78

Preparation of Cyclosporin Trifluoride

To a dried 25 mL flask charged with a solution of cyclosporin diol from Example 63 (50 mg, 0.041 mmol) in methylene chloride (2 mL) was added 3,3,3-trifluoropropene gas (39 mg, 0.41 mmol). The solution was treated with Grubbs' catalyst $2^{nd}$ generation (18 mg, 0.021 mmol) and the resulting mixture was allowed to stir while refluxing overnight at 50° C. in an atmosphere of 3,3,3-trifluoropropene gas (via attached balloon). After 17 h, Grubbs' catalyst $2^{nd}$ generation (18 mg, 0.021 mmol) was added and the reaction was left to reflux overnight at 50° C. in an atmosphere of 3,3,3-trifluoropropene gas. The reaction was concentrated to dryness under reduced pressure. Purification by semi-preparative HPLC yielded the desired product (2 mg, 4%) as a pink solid: $^1$H NMR (300 MHz, CDCl$_3$) δ 8.06 (d, J=10.0 Hz, 1H), 7.68 (d, J=8.0 Hz, 1H), 7.52 (d, J=8.5 Hz, 1H), 7.20 (d, J=8.5 Hz, 1H), 6.42-6.33 (m, 1H), 5.70 (dd, J=11.0, 8.5 Hz, 1H), 5.62-5.53 (m, 2H), 5.26 (dd, J=12.0, 4.0 Hz, 1H), 5.11-5.03 (m, 4H), 5.01-4.92 (m, 2H), 4.83 (t, J=7.0 Hz, 1H), 4.63 (t, J=9.5 Hz, 1H), 4.55 (t, J=7.0 Hz, 1H), 4.04 (d, J=6.0 Hz, 2H), 3.76 (t, J=7.0 Hz, 1H), 3.52 (s, 3H), 3.30 (s, 3H), 3.27 (s, 3H), 3.16 (s, 3H), 3.11 (s, 3H), 2.70 (s, 3H), 2.68 (s, 3H), 2.63-2.52 (m, 1H), 2.47-2.31 (m, 2H), 2.19-0.71 (m, 65H); ESI MS m/z 1287 $[C_{63}H_{110}F_3N_{11}O_{13}+H]^+$; HPLC 94.3% (AUC), $t_R$=13.17 min.

Example 79

Preparation of the Acetate of Cyclosporin α,β-Unsaturated Aldehyde

A mixture of cyclosporin diacetate from Example 64 (100 mg, 0.076 mmol), acrolein dimethyl acetal (0.087 mL, 0.76 mmol), Grubbs' catalyst $2^{nd}$ generation (12.7 mg, 0.015 mmol) and toluene (2 mL) was heated at 55° C. in a 25 mL flask overnight. The catalyst (12.7 mg) and acrolein dimethyl acetal (0.087 mL) were refilled and the mixture was stirred at the same temperature for an additional 24 h. The catalyst (12.7 mg) was again refilled and the reaction was allowed to stir at 55° C. for 6 h. An additional 20 mg of catalyst was added and the reaction was allowed to stir at 55° C. overnight. The catalyst (32.3 mg) was refilled again and an additional 1 mL of acrolein dimethyl acetal was added. After 2 days at 55° C., 20 mg of Grubbs' catalyst was added as well as 0.017 mL of acrolein dimethyl acetal. After 24 h, the reaction was cooled to room temperature and concentrated in vacuo. The residue was purified by semi-preparative HPLC to afford the acetate of cyclosporin α,β-unsaturated aldehyde (40 mg, 40%): $^1$H NMR (300 MHz, CDCl$_3$) δ 9.41 (d, J=7.9 Hz, 1H), 8.60 (d, J=9.7 Hz, 1H), 8.01 (d, J=6.8 Hz, 1H), 7.60 (d, J=8.0 Hz, 2H), 6.82-6.67 (m, 1H), 5.99 (dd, J=15.4, 7.8 Hz, 1H), 5.68 (dd, J=11.0, 3.9 Hz, 1H), 5.54 (s, 2H), 5.33-5.12 (m, 3H), 5.09-4.92 (m, 3H), 4.84 (t, J=7.2 Hz, 1H), 4.68 (t, J=9.4 Hz, 1H), 4.56-4.32 (m, 3H) 3.38 (s, 3H), 3.28 (s, 3H), 3.22 (s, 3H), 3.20 (s, 3H), 3.16 (s, 3H), 2.68 (s, 3H), 2.67 (s, 3H), 2.51-2.13 (m, 3H), 2.11 (s, 3H), 2.04 (s, 3H), 1.99-1.58 (m, 7H), 1.51-0.79 (m, 57H); ESI MS m/z 1331 $[C_{67}H_{115}N_{11}O_{16}+H]^+$.

Example 80

Preparation of the Acetate of Cyclosporin Dienyl Chloride

To a dried 25 mL flask charged with a solution of the acetate of cyclosporin α,β-unsaturated aldehyde from Example 79 (71 mg, 0.053 mmol) and chloroform (63 mg, 0.53 mmol) in THF (3 mL) was added chromium chloride (195 mg, 1.59 mmol). The resulting mixture was heated to 50° C. and stirred under N$_2$ for 2 h. The reaction was then cooled to room temperature and poured into 200 mL of ice-water with vigorously stirring. The aqueous layer was then extracted with ethyl acetate (3×200 mL). The combined organics were washed with brine (80 mL) and dried over anhydrous sodium sulfate, and then concentrated under vacuum. The crude material was purified by semi-preparative HPLC to yield the acetate of cyclosporin dienyl chloride (44 mg, 63%) as a white solid: $^1$H NMR (300 MHz, CDCl$_3$) δ 8.64 (d, J=9.9 Hz, 1H), 8.05 (d, J=13.3 Hz, 1H), 7.69 (d, J=9.0 Hz, 1H), 7.64 (d, J=7.8 Hz, 1H), 6.39 (dd, J=13.2, 10.7 Hz, 1H), 6.06 (d, J=13.3 Hz, 1H), 5.92-5.67 (m, 1H), 5.50 (s, 2H) 5.41-5.25 (m, 2H), 5.23-5.13 (m, 1H), 5.09-4.93 (m, 3H), 4.85 (t, J=7.1 Hz, 1H), 4.77 (t, J=9.4 Hz, 1H), 4.57-4.34 (m, 2H), 3.67 (s, 3H), 3.26 (s, 3H), 3.23 (s, 3H), 3.19 (s, 3H), 3.14 (s, 3H), 2.68 (s, 6H), 2.48-2.31 (m, 1H), 2.11 (s, 3H), 2.02 (s, 3H), 1.82-1.63 (m, 4H), 1.48-0.68 (m, 65H); ESI MS m/z 1364 $[C_{68}H_{116}ClN_{11}O_{15}+H]^+$.

Example 81

Preparation of Cyclosporin Dienyl Chloride

A solution of the acetate of cyclosporin dienyl chloride from Example 80 (44 mg, 0.03 mmol) in MeOH (1 mL) was treated with potassium carbonate (83 mg, 0.60 mmol). This was allowed to stir at room temperature overnight. The reaction was then diluted with ethyl acetate (30 mL), washed with a saturated solution of sodium bicarbonate (20 mL), washed with brine (20 mL) and then dried over anhydrous sodium sulfate. It was then concentrated under reduced pressure. The crude material was purified by semi-preparative HPLC to yield cyclosporin dienyl chloride (6 mg, 16%): $^1$H NMR (300 MHz, CDCl$_3$) δ 8.10 (d, J=9.9 Hz, 1H), 7.68 (d, J=7.5 Hz, 1H), 7.62 (d, J=8.8 Hz, 1H), 7.27 (d, J=6.4 Hz, 1H), 6.42 (dd, J=13.0, 10.8 Hz, 1H), 6.07 (d, J=13.1 Hz, 1H), 5.91 (dd, J=15.2, 10.9 Hz, 1H), 5.69 (dd, J=10.5, 3.6 Hz, 1H), 5.47-5.52 (m, 1H), 5.50 (d, J=6.3 Hz, 1H), 5.29 (dd, J=11.6, 3.9 Hz, 1H), 5.12-4.92 (m, 3H), 4.83 (t, J=7.3 Hz, 1H), 4.68-4.60 (m, 1H), 4.54 (t, J=7.2 Hz, 1H), 3.49 (s, 3H), 3.30 (s, 3H), 3.26 (s, 3H), 3.16 (s, 3H), 3.11 (s, 3H), 2.70 (s, 3H), 2.69 (s, 3H), 2.57-2.32 (m, 1H), 2.21-1.91 (m, 4H), 1.61-0.69 (m, 69H); ESI MS m/z 1280 $[C_{64}H_{112}ClN_{11}O_{13}+H]^+$; HPLC 96.9% (AUC), $t_R$=13.98 min.

Example 82

Preparation of the Acetate of Cyclosporin Dienyl Iodide

A 25 mL flask charged with a solution of the acetate of cyclosporin α,β-unsaturated aldehyde from Example 79 (36 mg, 0.027 mmol) in THF (2 mL) was treated with iodoform (108 mg, 0.027 mmol). It was then cooled to −78° C. and chromium chloride (99 mg, 0.81 mmol) was added to the solution. The mixture was stirred at −78° C. for 10 min and then warmed to 0° C., at which it was stirred for 1.5 h. The reaction was then poured into 70 mL of vigorously stirring ice water. The material was extracted with 100 mL of ethyl acetate. The organic layer was rinsed with 15 mL of brine, dried over anhydrous sodium sulfate, and concentrated under reduced pressure. The crude material was purified by semi-preparative HPLC to yield the acetate of cyclosporin dienyl iodide (14 mg, 35%): $^1$H NMR (300 MHz, CDCl$_3$) δ 8.64 (d, J=9.8 Hz, 1H), 8.05 (d, J=6.9 Hz, 1H), 7.71 (d, J=8.9 Hz, 1H), 7.66 (d, J=7.7 Hz, 1H), 6.95 (dd, J=14.2, 10.6 Hz, 1H), 6.15 (d, J=14.4 Hz, 1H), 5.81 (dd, J=14.8, 10.6 Hz, 1H), 5.69 (dd, J=10.8, 3.9 Hz, 1H), 5.50 (s, 2H), 5.43-5.27 (m, 3H), 5.22-5.13 (m, 1H), 5.09-4.95 (m, 3H), 4.85 (t, J=7.1 Hz, 1H), 4.78 (t, J=9.2 Hz, 1H), 4.58-4.32 (m, 3H), 3.37 (s, 3H), 3.25 (s, 3H), 3.19 (s, 3H), 3.14 (s, 3H), 2.68 (s, 6H), 2.49-2.32 (m, 1H), 2.11 (s, 3H), 2.02 (s, 3H), 1.97-1.57 (m, 4H), 1.48-0.71 (m, 65H); ESI MS m/z 1455 $[C_{68}H_{116}IN_{11}O_{15}+H]^+$.

Example 83

Preparation of Cyclosporin Dienyl Iodide

A solution of the acetate of cyclosporin dienyl iodide from Example 82 (13.7 mg, 0.003 mmol) in MeOH (1 mL) was treated with potassium carbonate (26 mg, 0.19 mmol). This was allowed to stir at room temperature overnight. The reaction was then diluted with 30 mL of ethyl acetate, washed with a saturated solution of sodium bicarbonate (20 mL), washed with 20 mL of brine and then dried over anhydrous sodium sulfate. It was then concentrated under reduced pressure. The crude material was purified by semi-preparative HPLC to yield cyclosporin dienyl iodide (7.3 mg, 59%) as a white solid and a mixture of cis and trans-isomers: $^1$H NMR (300 MHz, CDCl$_3$) δ 8.08 (d, J=10.1 Hz, 1H), 7.66 (d, J=7.3 Hz, 1H), 7.54-7.47 (m, 1H), 7.19 (d, J=7.8 Hz, 1H), 7.01 (dd, J=14.2, 10.8 Hz, 0.8H), 6.69 (dd, J=9.7, 7.4 Hz, 0.2H), 6.22-6.07 (m, 1H), 5.96-5.83 (m, 1H), 5.73-5.53 (m, 1H), 5.49 (t, J=6.9 Hz, 1H), 5.33-5.24 (m, 1H), 5.13-4.92 (m, 6H), 4.83 (t, J=7.3 Hz, 1H), 4.65 (t, J=8.6 Hz, 1H), 4.58-4.46 (m, 1H), 4.04 (d, J=6.7 Hz, 1H), 3.51 (s, 0.6H), 3.50 (s, 2.4H), 3.31(s, 3H), 3.27 (s, 2.4H), 3.26 (s, 0.6H), 3.15 (s, 3H), 3.12 (s, 3H), 2.69 (s, 1.2H), 2.68 (s, 4.8H) 2.52-2.43 (m, 1H), 2.32-0.72 (m, 70H); ESI MS m/z 1371 $[C_{64}H_{112}IN_{11}O_{13}+H]^+$; HPLC 94.0% (AUC), $t_R$=14.22 min.

Example 84

Preparation of Cyclosporin Dienyl Bromide

A 25 mL flask charged with a solution of the acetate of cyclosporin α,β-unsaturated aldehyde from Example 79 (49 mg, 0.04 mmol) in THF (2 mL) was cooled to 0° C. and treated with bromoform (0.04 mL, 0.40 mmol). Chromium (II) chloride (147 mg, 1.20 mmol) was added to the solution. The mixture was stirred at 0° C. for 1.5 h and then the ice bath was removed. The mixture was left to stir at room temperature overnight. The reaction was then poured into 70 mL of vigorously stirring ice water. The material was extracted with 150 mL of ethyl acetate. The organic layer was rinsed with 25 mL of brine, dried over anhydrous sodium sulfate, and concentrated under reduced pressure. The crude material was purified by semi-preparative HPLC to yield the acetate of cyclosporin dienyl bromide (5.2 mg, 9%): ESI MS m/z 1408 $[C_{68}H_{115}BrN_{11}O_{15}+H]^+$.

A solution of the above acetate of cyclosporin dienyl bromide (5.2 mg, 0.004 mmol) in MeOH (1 mL) was treated with potassium carbonate (21 mg, 0.15 mmol). This was allowed to stir at room temperature for 7 h. The reaction was then diluted with 60 mL of ethyl acetate, washed with a saturated solution of sodium bicarbonate (10 mL), washed with 10 mL of brine and then dried over anhydrous sodium sulfate. It was then concentrated under reduced pressure. The crude material was purified using semi-preparative HPLC to yield cyclosporin dienyl bromide (2.1 mg, 40%): $^1$H NMR (300 MHz, CDCl$_3$) δ 8.10 (d, J=9.9 Hz, 1H), 7.73-7.62 (m, 1H), 7.58-7.58 (m, 1H), 7.18 (d, J=7.5 Hz, 1H), 6.70 (dd, J=13.4, 10.7 Hz, 1H), 6.16 (d, J=13.4 Hz, 1H), 5.88 (dd, J=15.0, 10.8 Hz, 1H), 5.73-5.57 (m, 1H), 5.48 (d, J=6.5 Hz, 1H), 5.38-5.23 (m, 2H), 5.12-4.92 (m, 6H), 4.83 (t, J=7.4 Hz, 1H), 4.65 (t, J=8.5 Hz, 1H), 4.52 (t, J=7.4 Hz, 1H), 4.22 (dd, J=5.7, 3.6 Hz, 1H), 4.04 (d, J=6.5 Hz, 1H), 3.50 (s, 3H), 3.31 (s, 3H), 3.27 (s, 3H), 3.15 (s, 3H), 3.12 (s, 3H), 2.69 (s, 3H), 2.68 (s, 3H), 2.49-2.26 (m, 1H), 2.22-0.67 (m, 68H); ESI MS m/z 1323 $[C_{64}H_{112}BrN_{11}O_{13}+H]^+$; HPLC>99% (AUC), $t_R$=13.93 min.

Example 85

Concanavalin A-Stimulated Splenocyte Assay

Male BALB/c mice, at 5 to 7 weeks of age, were sacrificed by CO$_2$ inhalation. Spleens were removed and dissociated by pushing through a nylon cell strainer. The splenocytes were washed in RPMI 1640/5% fetal calf serum (FCS) and pelleted at 400×g. Red blood cells were then lysed by resuspending the cell pellet in ACK lysis buffer (150 mM NH$_4$Cl, 1 mM KHCO$_3$, 0.1 mM EDTA, 3 mL per spleen) for 10 min at room temperature. After pelleting at 400×g, the cells were washed by resuspending in RPMI 1640/5% FCS and repelleting. The cell pellet was resuspended in RPMI 1640/5% FCS and again passed through a cell strainer to remove cell aggregates. The cells were then counted and adjusted to 2×10$^6$ cells/ml in RPMI 1640/10% FCS/50 µM 2-mercaptoethanol. Cell viability was assessed by Trypan blue staining. Cyclosporin A or the test compound and two micrograms of concanavalin A were added to the wells of a 96 well plate, prior to the addition of 2×10$^5$ splenocytes. The cells were cultured in a 37° C. CO$_2$ incubator for 2 days and then pulsed with 1 µCi of [$^3$H] thymidine for 6 hours. Cells were harvested onto filtermats with a TomTec 96 well plate harvester and lysed with H$_2$O. The filtermat and scintillation fluid were sealed in a plastic sleeve. [$^3$H]thymidine incorporation was measured with a Wallac Trilux plate counter. Initial screens were done at a fixed value of 100 ng/ml test compound. IC$_{50}$s were calculated from 7 point concentration-response curves using GraphPad software.

Example 86

Murine Ex Vivo Pharmacodynamic Assay

In vivo immunosuppressive activity can be determined for cyclosporin A and the disclosed cyclosporin analogs, as described below. The concanavalin A-stimulated splenocyte activity can be assessed in vivo using a method previously described by Peterson et al. (Peterson et al., "A Tacrolimus-Related Immunosuppressant with Biochemical Properties Distinct from Those of Tacrolimus," *Transplantation*, 65:10-18 (1998), which is hereby incorporated by reference in its entirety) or a slightly modified version thereof.

Optimal doses of cyclosporin A or an immunosuppressive compound of the present invention (four different doses of test drug plus a control set of animals with no drug) was administered orally or intravenously to male BALB/c or female C57BL mice. Three mice were tested at each dose. Concanavalin A was injected into the tail vein of the mouse at 4 hours after the administration of cyclosporin A or the immunosuppressive compound. One hour after the concanavalin A injection, the mice were euthanized, the spleens were removed under sterile conditions, and the extent of splenocyte proliferation was measured in a similar manner as described in Example 85. The percent inhibition relative to control was plotted graphically versus the dose of the immunosuppressive compound and an ED$_{50}$ value was determined. Each dose-response assay for the compound of the present invention was accompanied by a cyclosporin control at a single dose equal to the ED$_{50}$.

Although the invention has been described in detail for the purpose of illustration, it is understood that such detail is solely for that purpose, and variations can be made therein by those skilled in the art without departing from the spirit and scope of the invention which is defined by the following claims.

What is claimed:

1. A compound of Formula Ia:

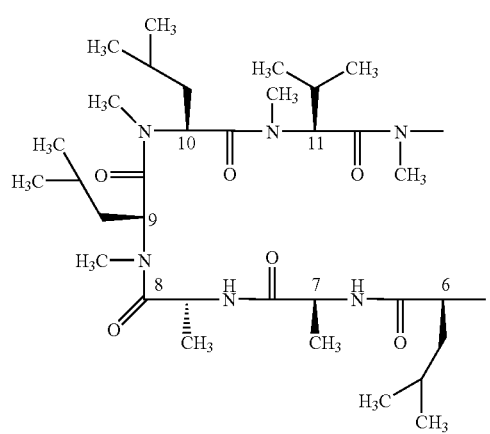

Formula Ia

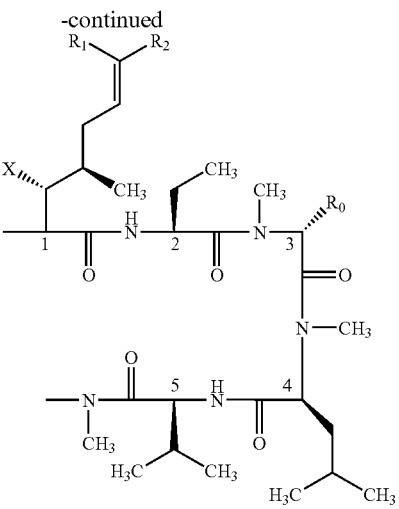

-continued wherein:
X is OH or OAc;
R$_0$ is H or CH$_2$OR$_3$;
R$_1$ is H or D;
R$_2$ is selected from the group consisting of:
  halogen,
  C$_3$-C$_6$ unsubstituted cycloalkyl,
  —CH=N—OR$_4$, and
  —CH=N—NR$_4$R$_5$;
R$_3$ is selected from the group consisting of:
  hydrogen,
  alkanoyl,
  alkenoyl,
  alkynoyl,
  aryloyl,
  arylalkanoyl,
  alkylaminocarbonyl,
  arylaminocarbonyl,
  arylalkylaminocarbonyl,
  alkyloxycarbonyl,
  aryloxycarbonyl, and
  arylalkyloxycarbonyl;
R$_4$ and R$_5$ are the same or different and independently selected from the group consisting of:
  hydrogen,
  C$_1$-C$_6$ saturated straight or branched carbon chain,
  C$_3$-C$_6$ unsaturated straight or branched carbon chain,
  C$_3$-C$_6$-substituted and unsubstituted cycloalkyl,
  C$_1$-C$_4$ carbon chain containing an aryl or heteroaryl,
  substituted and unsubstituted aryl,
  substituted and unsubstituted heteroaryl,
  alkanoyl,
  alkenoyl,
  alkynoyl,
  aryloyl,
  arylalkanoyl,
  alkylaminocarbonyl,
  arylaminocarbonyl,
  arylalkylaminocarbonyl,
  alkyloxycarbonyl,
  aryloxycarbonyl,
  arylalkyloxycarbonyl,
  alkylsulfonyl, and
  arylsulfonyl; and
R$_4$ together with R$_5$ results in the formation of a cyclic moiety of C$_2$-C$_6$ optionally containing heteroatom or heteroatoms, wherein the compound is a cis geometric isomer, a trans geometric isomer, or a mixture of the cis and the trans geometric isomers or a pharmaceutically acceptable salt thereof.

2. The compound according to claim 1, wherein X is OH or OAc, $R_0$ is H, $CH_2OH$ or $CH_2OAc$, $R_1$ is H or D.

3. The compound according to claim 2, wherein $R_2$ is selected from the group consisting of F, Cl, Br, and I.

4. A compound of Formula Ia:

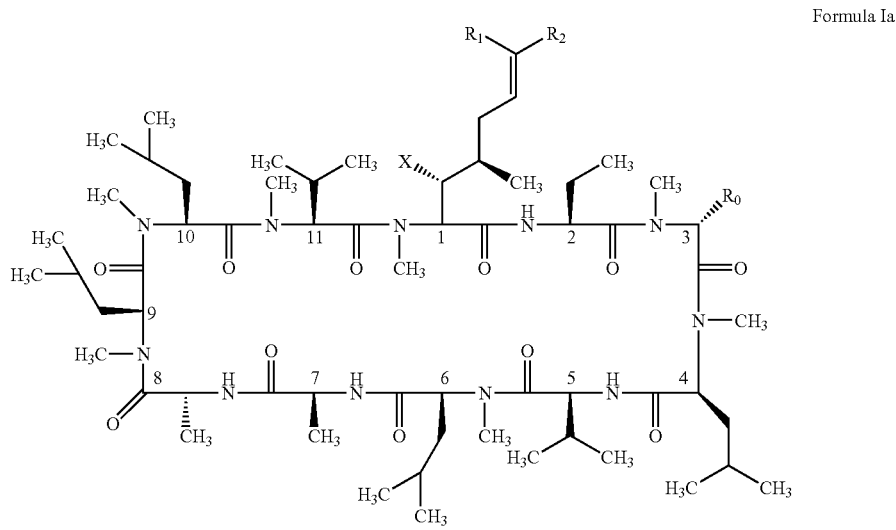

Formula Ia wherein:

X is OH or OAc;
$R_0$ is H, $CH_2OH$, or $CH_2OAc$;
$R_1$ is H or D;

$R_2$ is selected from the group consisting of —CH=CHF, —CH=CHCl, —CH=CHBr, and —CH=CHI, wherein the compound is a cis geometric isomer, a trans geometric isomer, or a mixture of the cis and the trans geometric isomers or a pharmaceutically acceptable salt thereof.

5. The compound according to claim 2, wherein $R_2$ is cyclopropyl.

6. The compound according to claim 2, wherein $R_2$ is selected from the group consisting of —CH=N—OH, —CH=N—OCH$_3$, —CH=N—OCH$_2$CH$_3$, —CH=N—NHCH$_3$, and —CH=N—N(CH$_3$)$_2$.

7. A compound of Formula Ib:

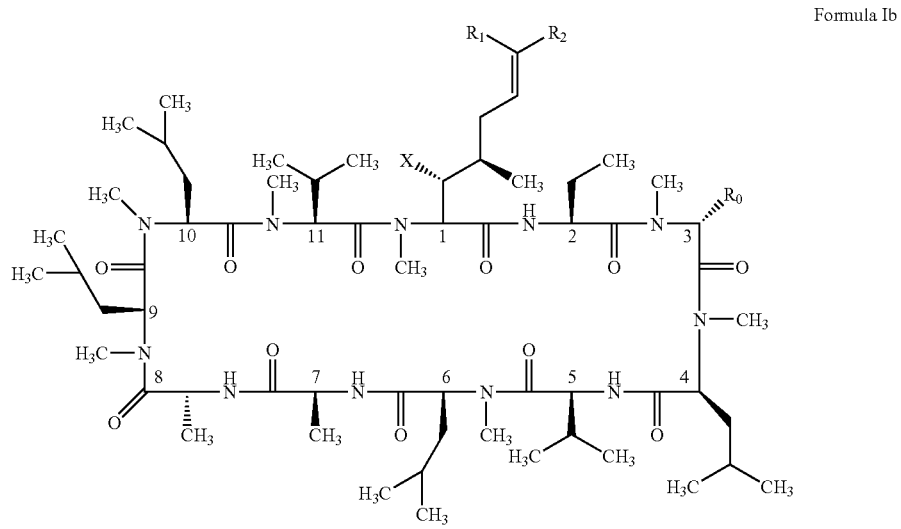

Formula Ib wherein:
X is OH or OAc;
$R_0$ is H or $CH_2OR_3$;
$R_1$ is halogen;
$R_2$ is selected from the group consisting of:
hydrogen,
deuterium,
halogen,
$C_2$-$C_6$ unsaturated straight or branched carbon chain, optionally containing halogen,
$C_3$-$C_6$ substituted and unsubstituted cycloalkyl,
substituted and unsubstituted aryl, and
substituted and unsubstituted heteroaryl; and
$R_3$ is selected from the group consisting of:
hydrogen,
alkanoyl,
alkenoyl,
alkynoyl,
aryloyl,
arylalkanoyl,
alkylaminocarbonyl,
arylaminocarbonyl,
arylalkylaminocarbonyl,
alkyloxycarbonyl,
aryloxycarbonyl, and
arylalkyloxycarbonyl,
wherein the compound is a cis geometric isomer, a trans geometric isomer, or a mixture of the cis and the trans geometric isomers or a pharmaceutically acceptable salt thereof.

8. A pharmaceutical composition comprising a pharmaceutically acceptable carder and a therapeutically effective amount of the compound of claim 1.

9. A pharmaceutical composition comprising a pharmaceutically acceptable carder and a therapeutically effective amount of the compound of claim 7.

* * * * *